United States Patent
Brown et al.

(10) Patent No.: US 10,144,738 B2
(45) Date of Patent: Dec. 4, 2018

(54) PYRAZOLO[1,5-A]PYRAZIN-4-YL DERIVATIVES

(71) Applicant: Pfizer Inc., New York, NY (US)

(72) Inventors: Matthew Frank Brown, Stonington, CT (US); Alpay Dermenci, East Lyme, CT (US); Andrew Fensome, Harvard, MA (US); Brian Stephen Gerstenberger, Brookline, MA (US); Matthew Merrill Hayward, Old Lyme, CT (US); Dafydd Rhys Owen, Concord, MA (US); Stephen Wayne Wright, Old Lyme, CT (US); Li Huang Xing, Lexington, MA (US); Xiaojing Yang, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/437,618

(22) Filed: Feb. 21, 2017

(65) Prior Publication Data
US 2017/0240552 A1    Aug. 24, 2017

Related U.S. Application Data

(60) Provisional application No. 62/299,130, filed on Feb. 24, 2016.

(51) Int. Cl.
*C07D 487/04*    (2006.01)
*A61K 31/4985*    (2006.01)

(52) U.S. Cl.
CPC .................... *C07D 487/04* (2013.01)

(58) Field of Classification Search
CPC ...................................... C07D 487/04
See application file for complete search history.

(56) References Cited

FOREIGN PATENT DOCUMENTS

WO    2011/130146 A1    10/2011
WO    2016/090285 A1    6/2016

OTHER PUBLICATIONS

Kisseleva et al, "Signaling through the JAK/STAT pathway, recent advances and future challenges", Gene 285:1-24 (2002).

Liang et al, "Therapeutic potential of tyrosine kinase 2 in autoimmunity", Expert Opin. Ther. Targets 18(5):571-580 (2014).
Murray, "The JAK-STAT Signaling Pathway: Input and Output Integration", The Journal of Immunology 178:2623-2629 (2007).
Neubauer et al, "Jak2 Deficiency Defines an Essential Developmental Checkpoint in Definitive Hematopoiesis", Cell 93:397-409 (1998).
O'Shea et al, "JAK and STAT Signaling Molecules in Immunoregulation and Immune-Mediated Disease", Immunity 36:542-550 (2012).
Parganas et al, "Jak2 Is Essential for Signaling through a Variety of Cytokine Receptors", Cell 93:385-395 (1998).
Yamaoka et al, "The Janus kinases (Jaks)", Genome Biology 5:253 (2004).
PCT International Search Report and Written Opinion for International Patent Application No. PCT/IB2017/050748 dated Apr. 3, 2017.

*Primary Examiner* — Brian E McDowell
(74) *Attorney, Agent, or Firm* — A. David Joran

(57) ABSTRACT

A compound having the structure:

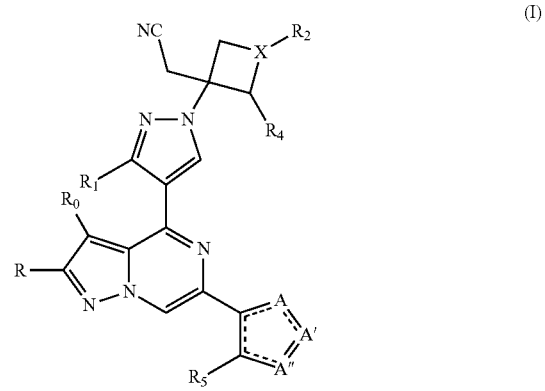

or a pharmaceutically acceptable salt thereof, wherein A, A' and A" are independently O, C=O, etc.; $R_0$ and R are independently H, Br, Cl, F, or $C_1$-$C_6$ alkyl; $R_1$ is H, $C_1$-$C_6$ alkyl, or hydroxy($C_1$-$C_6$ alkyl); $R_2$ is selected from the group consisting of H, $C_1$-$C_6$ alkyl, $C_1$-$C_6$ alkoxy, etc.; $R_6$, $R_7$ and $R_8$ are each independently H, $C_1$-$C_6$ alkyl, $C_1$-$C_4$ alkoxy($C_1$-$C_6$ alkyl), etc.; and, n is 0, 1, 2 or 3. Also provided are methods of treatment as Janus Kinase inhibitors and pharmaceutical compositions containing the compounds of the invention and combinations thereof with other therapeutic agents.

24 Claims, No Drawings

PYRAZOLO[1,5-A]PYRAZIN-4-YL DERIVATIVES

This application claims the benefit under 35 U.S.C. § 119(e) of Ser. No. 62/299,130, filed Feb. 24, 2016.

FIELD OF THE INVENTION

The present invention provides pharmaceutically active pyrazolo[1,5-a]pyrazin-4-yl TYK2 ligands and analogues. Such compounds are useful for inhibiting Janus Kinases (JAKs). This invention also is directed to compositions comprising methods for making such compounds, and methods for treating and preventing conditions mediated by JAK.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, cell function, survival, apoptosis, and cell mobility implicated in the aforementioned and related diseases.

Thus, protein kinases have emerged as an important class of enzymes as targets for therapeutic intervention. In particular, the JAK family of cellular protein tyrosine kinases (JAK1, JAK2, JAK3, and Tyk2) play a central role in cytokine signaling (Kisseleva et al., Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the interferon (IFN) family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23), gamma C family (IL-2, IL-7, TSLP, IL-9, IL-15, IL-21, IL-4, IL-13), IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

There remains a need for new compounds that effectively and selectively inhibit specific JAK enzymes: TYK2 in particular. TYK2 is a JAK kinase family member, and is important in the signaling of the type I interferons (including IFNalpha, INFbeta), IL-6, IL-10, IL-12 and IL-23 (Liang, Y. et al., Expert Opinion on Therapeutic Targets, 18, 5, 571-580 (2014)). As such, TYK2 signals with other members of the JAK kinase family in the following combinations: TYK2/JAK1, TYK2/JAK2, TYK2/JAK1/JAK2. TYK2 has been shown to be important in the differentiation and function of multiple cell types important in inflammatory disease and autoimmune disease including natural killer cells, B cells, and T helper cell types. Aberrant TYK2 expression is associated with multiple autoimmune or inflammatory conditions. Modulation of immune activity through inhibition of TYK2 kinase activity can prove useful in the treatment of various immune disorders (O'Shea J J, Plenge R, Immunity, 36, 542-50 (2012); Murray, P. J., J. Immunol., 178, 2623-2629 (2007); Kisseleva, T., et al., Gene, 285, 1-24 (2002)) while avoiding JAK2 dependent erythropoietin (EPO) and thrombopoietin (TPO) signaling (Neubauer H., et al., Cell, 93(3), 397-409 (1998); Parganas E., et al., Cell, 93(3), 385-95 (1998)).

SUMMARY OF THE INVENTION

The present invention provides a compound of formula I having the structure:

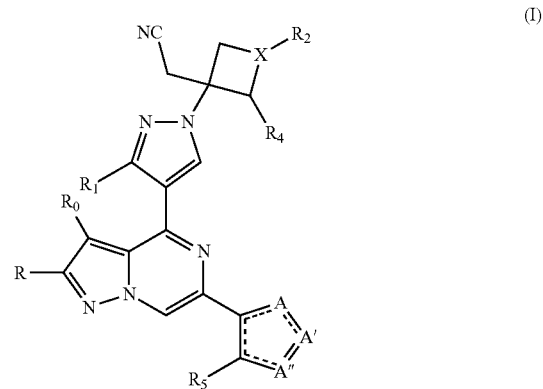

(I)

or a pharmaceutically acceptable salt thereof, or a pharmaceutically acceptable solvate of said compound or pharmaceutically acceptable salt, wherein: A, A' and A" are independently 0, C=O, C—R' or N—R", where R' and R" may independently be H, amino, —NR$_7$COR$_6$, COR$^6$, —CONR$_7$R$_8$, C$_1$-C$_6$ alkyl, or hydroxy(C$_1$-C$_6$ alkyl), and R" may be present or absent, and is present where the rules of valency permit, and where not more than one of A, A' and A" is O or C=O; R$_0$ and R are independently H, Br, Cl, F, or C$_1$-C$_6$ alkyl; R$_1$ is H, C$_1$-C$_6$ alkyl, or hydroxy(C$_1$-C$_6$ alkyl); R$_2$ is selected from the group consisting of H, C$_1$-C$_6$ alkyl, C$_1$-C$_6$ alkoxy, hydroxy(C$_1$-C$_6$ alkyl), phenyl(C$_1$-C$_6$ alkyl), formyl, heteroaryl, heterocyclic, —COR$_6$, —OCOR$_6$, —COOR$_6$, —NR$_7$COR$_6$, —CONR$_7$R$_8$, and —(CH$_2$)$_n$—W, where W is cyano, hydroxy, C$_3$-C$_8$ cycloalkyl, —SO$_2$NR$_7$R$_8$, and —SO$_2$—R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl; X is C—R$_3$ or N, where R$_3$ may be H or C$_1$-C$_6$ alkyl; R$_4$ and R$_5$ are independently H, amino, C$_1$-C$_6$ alkyl, or hydroxy(C$_1$-C$_6$ alkyl); R$_6$, R$_7$ and R$_8$ are each independently H, C$_1$-C$_6$ alkyl, C$_1$-C$_4$ alkoxy(C$_1$-C$_6$ alkyl), or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl; and, n is 0, 1, 2 or 3.

In other aspects, the present invention also provides:
pharmaceutical compositions which comprise a pharmaceutically acceptable carrier and a compound of formula I;
methods for treating conditions or disorders including inflammation, autoimmune disease, systemic lupus erythematous, lupus nephritis, discoid lupus, cutaneous lupus, central nervous system lupus, rheumatoid arthritis, psoriatic arthritis, inflammatory bowel disease, Crohn's disease, ulcerative colitis, asthma, allergic asthma, Type I diabetes, polymyositis, dermatomyositis, type I interferonopathies including AicardiGoutieres syndrome and other mendelian diseases of overexpression of type I interferon, multiple sclerosis, primary progressive multiple sclerosis, relapsing remitting multiple sclerosis, primary biliary cirrhosis also known as primary biliary cholangitis, primary sclerosing cholangitis, autoimmune hepatitis, non-alcoholic fatty liver disease, non-alcoholic steatohepatitis, psoriasis, dermatomyositis, scleroderma, atopic dermatitis, vitiligo, alopecia areata, spondylopathy, ankylosing spondylitis, Alzheimer's disease, neuro-inflammation myositis, vasculitis, pemphigus, Crohn's disease, lupus, nephritis, psoriasis, multiple sclerosis, major depression disorder, allergy, asthma, Sjogren's disease, dry eye syndrome, transplant rejection, cancer, inflammatory bowel disease, septic shock, cardiopulmonary dysfunction, vitiligo, alopecia, acute respiratory disease, ankylosing spondylitis, autoimmune hepatitis, primary sclerosing cholangitis, primary biliary cirrhosis, Alzheimer's disease, or cachexia by administering to a subject in need a therapeutically effective amount of a compound of formula I or a pharmaceutically acceptable salt thereof;

Methods for treating conditions or disorders including atopic dermatitis, eczema, psoriasis, scleroderma, lupus, pruritus, fatigue, other pruritic conditions, allergic reactions including allergic dermatitis in mammal, horse allergic diseases including bite hypersensitivity, summer eczema, sweet itch in horses, heaves, inflammatory airway disease, recurrent airway obstruction, airway hyper-responsiveness, and chronic obstruction pulmonary disease by administering to a mammal in need a therapeutically effective amount of a compound of formula I, or a pharmaceutically acceptable salt thereof; and, methods for the preparation of compounds of the present invention.

The present invention will be further understood from the following description given by way of example only. The present invention is directed to a class of pyrazolo[1,5-a]pyrazin-4-yl derivatives. In particular, the present invention is directed to pyrazolo[1,5-a]pyrazin-4-yl compounds useful as inhibitors of JAKs, and particularly TYK2. While the present invention is not so limited, an appreciation of various aspects of the invention will be gained through the following discussion and the examples.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms. The carbon atom content of alkyl and various other hydrocarbon-containing moieties is indicated by a prefix designating a lower and upper number of carbon atoms in the moiety, that is, the prefix $C_i$-$C_j$, indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH group. The term "heterocyclic" refers to a saturated or partially saturated (i.e., non aromatic) heterocycle which contains three to ten ring atoms where one or more, preferably, one, two or three ring atoms, are heteroatom(s) selected from N, O and S, the remaining being carbon, and which may be attached via a ring nitrogen atom or a ring carbon atom. Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

The term "aryl" refers to an aromatic monocyclic or bicyclic hydrocarbon containing six to ten ring carbon atoms which may be attached via one of the ring carbon atoms. Equally, when substituted, the substituent may be located on a ring carbon atom. Specific examples include, but are not limited to, phenyl, tolyl, xylyl, trimethylphenyl, and naphthyl. Examples of aryl substituents include, but are not limited to, alkyl, hydroxyl, halo, nitrile, alkoxy, trifluoromethyl, carboxamido, $SO_2Me$, benzyl, and substituted benzyl.

The term "heteroaryl" refers to a monovalent aromatic monocyclic or bicyclic heterocycle of five to ten ring atoms where one or more, preferably, one, two or three ring atoms, are heteroatom(s) selected from N, O, and S, the remaining being carbon, and which may be attached via a ring carbon atom or a ring nitrogen atom with an appropriate valency. Equally, when substituted, the substituent may be located on a ring carbon atom or a ring nitrogen atom with an appropriate valency. Specific examples include, but are not limited to, thienyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl. The term "cycloalkyl" means a monocyclic, saturated hydrocarbon group of the formula $C_nH_{2n-1}$. Examples include, but are not limited to, cyclopropyl, cyclobutyl, cyclopentyl, cyclohexyl, and cycloheptyl. Unless otherwise specified, a cycloalkyl group comprises from 3 to 8 carbon atoms.

The terms "halo" and "halogen" refer to fluoride (F), chloride (Cl), bromide (Br) or iodide (I).

The term "mammal" refers to human, livestock or companion animals.

The term "companion animal" or "companion animals" refers to animals kept as pets or household animal. Examples of companion animals include dogs, cats, and rodents including hamsters, guinea pigs, gerbils and the like, rabbits, ferrets and birds.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits, as well as birds, such as chickens, ducks and turkeys.

The term "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present invention in combination with other therapies.

The term "therapeutically-effective" indicates the capability of an agent to prevent, or improve the severity of, the disorder. The phrase "therapeutically-effective" is to be understood to be equivalent to the phrase "effective for the treatment, prevention, or amelioration", and both are intended to qualify the amount of an agent—which will achieve the goal of improvement in the severity of cancer, cardiovascular disease, or pain and inflammation and the frequency of incidence over treatment of each agent by itself.

"Pharmaceutically acceptable" means suitable for use in mammals, companion animals or livestock animals.

If substituents are described as being "independently selected" from a group, each substituent is selected independent of the other. Each substituent therefore may be identical to or different from the other substituent(s).

DETAILED DESCRIPTION OF THE INVENTION

The present invention is related to novel compounds which are TYK2 modulators useful for the treatment of diseases and conditions associated with dysregulation of TYK2. The present invention further provides pharmaceutical compositions comprising such JAK enzyme modulators as well as methods of treating and/or preventing such diseases and conditions. Accordingly, the present invention provides a compound of formula I as represented above having the structure (I):

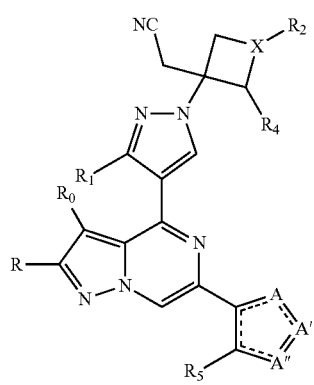

The invention also provides a compound having the structure (Ia):

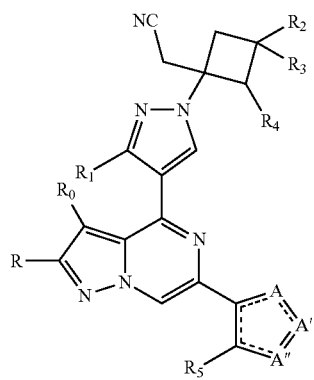

or a pharmaceutically acceptable salt thereof, or a pharmaceutically acceptable solvate of said compound or pharmaceutically acceptable salt, wherein: A, A' and A" are independently O, C=O, C—R' or N—R", where R' and R" may independently be H, amino, —NR$_7$COR$_6$, COR$^6$, —CONR$_7$R$_8$, C$_1$-C$_6$ alkyl-, or hydroxy(C$_1$-C$_6$ alkyl)-, and R" may be present or absent, and is present where the rules of valency permit, and where not more than one of A, A' and A" is O or C=O; R$_0$ and R are independently H, Br, Cl, F, or C$_1$-C$_6$ alkyl; R$_1$ is H, C$_1$-C$_6$ alkyl, or hydroxy(C$_1$-C$_6$ alkyl)-; R$_2$ is selected from the group consisting of H, C$_1$-C$_6$ alkyl, C$_1$-C$_6$ alkoxy-, hydroxy(C$_1$-C$_6$ alkyl)-, phenyl(C$_1$-C$_6$ alkyl)-, formyl, heteroaryl, heterocyclic, —COR$_6$, —OCOR$_6$, —COOR$_6$, —NR$_7$COR$_6$, —CONR$_7$R$_8$, and —(CH$_2$)$_n$—W, where W is cyano, hydroxy, C$_3$-C$_8$ cycloalkyl, —SO$_2$NR$_7$R$_8$, and —SO$_2$—R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl; R$_3$ may be H or C$_1$-C$_6$ alkyl; R$_4$ and R$_5$ are independently H, amino, C$_1$-C$_6$ alkyl, or hydroxy(C$_1$-C$_6$ alkyl); R$_6$, R$_7$ and R$_8$ are each independently H, C$_1$-C$_6$ alkyl, C$_1$-C$_4$ alkoxy(C$_1$-C$_6$ alkyl), or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl; and, n is 0, 1, 2 or 3.

The invention further provides a compound having the structure (Ib):

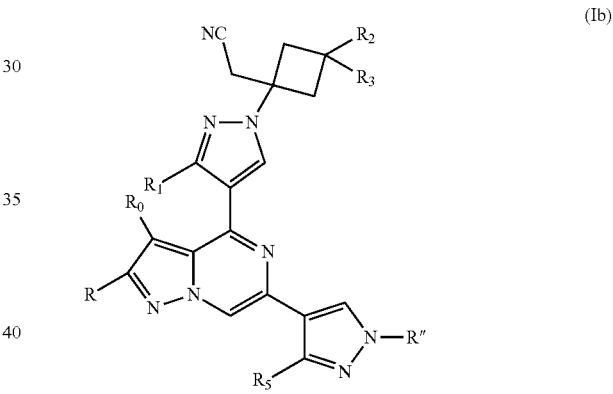

or a pharmaceutically acceptable salt thereof, or a pharmaceutically acceptable solvate of said compound or pharmaceutically acceptable salt, wherein: R" is H, —COR$_6$, —CONR$_7$R$_8$, C$_1$-C$_6$ alkyl-, or hydroxy(C$_1$-C$_6$ alkyl)-; R$_0$ and R are independently H, Br, Cl, F, or C$_1$-C$_6$ alkyl; R$_1$ is H, C$_1$-C$_6$ alkyl, or hydroxy(C$_1$-C$_6$ alkyl); R$_2$ is selected from the group consisting of H, C$_1$-C$_6$ alkyl, C$_1$-C$_6$ alkoxy, hydroxy(C$_1$-C$_6$ alkyl), phenyl(C$_1$-C$_6$ alkyl), formyl, heteroaryl, heterocyclic, —COR$_6$, —OCOR$_6$, —COOR$_6$, —NR$_7$COR$_6$, —CONR$_7$R$_8$, and —(CH$_2$)$_n$—W, where W is cyano, hydroxy, C$_3$-C$_8$ cycloalkyl, —SO$_2$NR$_7$R$_8$, and —SO$_2$—R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl; R$_3$ may be H or C$_1$-C$_6$ alkyl; R$_5$ is H, amino, C$_1$-C$_6$ alkyl, or hydroxy(C$_1$-C$_6$ alkyl); R$_6$, R$_7$ and R$_8$ are each independently H, C$_1$-C$_6$ alkyl, C$_1$-C$_4$ alkoxy(C$_1$-C$_6$ alkyl), or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl; and, n is 0, 1, 2 or 3.

The invention also provides a compound having the structure (Ic):

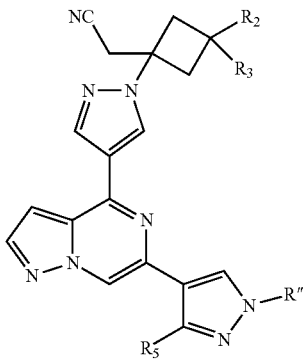

or a pharmaceutically acceptable salt thereof, or a pharmaceutically acceptable solvate of said compound or pharmaceutically acceptable salt, wherein: R" is H, —COR$_6$, —CONR$_7$R$_8$, C$_1$-C$_6$ alkyl, or hydroxy(C$_1$-C$_6$ alkyl); R$_2$ is selected from the group consisting of H, C$_1$-C$_6$ alkyl-, C$_1$-C$_6$ alkoxy-, hydroxy(C$_1$-C$_6$ alkyl)-, phenyl(C$_1$-C$_6$ alkyl)-, formyl, heteroaryl, heterocyclic, —COR$_6$, —OCOR$_6$, —COOR$_6$, —NR$_7$COR$_6$, —CONR$_7$R$_8$, and —(CH$_2$)$_n$—W, where W is cyano, hydroxy, C$_3$-C$_8$ cycloalkyl, —SO$_2$NR$_7$R$_8$, and —SO$_2$—R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl; R$_3$ is H or C$_1$-C$_6$ alkyl; R$_5$ is H, amino, C$_1$-C$_6$ alkyl-, or hydroxy(C$_1$-C$_6$ alkyl)-; R$_6$, R$_7$ and R$_8$ are each are each independently H, C$_1$-C$_6$ alkyl-, C$_1$-C$_4$ alkoxy(C$_1$-C$_6$ alkyl)-, or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl; and, n is 1, 2 or 3. In a particular embodiment, the invention provides said compound wherein R" is C$_1$-C$_6$ alkyl and R$_5$ is H.

The invention also provides a compound having the structure (Id):

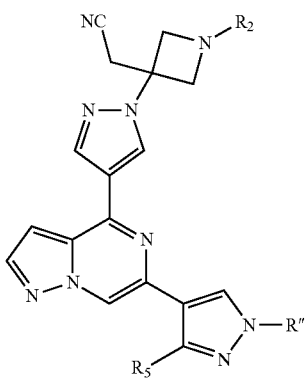

or a pharmaceutically acceptable salt thereof, or a pharmaceutically acceptable solvate of said compound or pharmaceutically acceptable salt, wherein: R" is H, —COR$_6$, —CONR$_7$R$_8$, C$_1$-C$_6$ alkyl, or hydroxy(C$_1$-C$_6$ alkyl); R$_2$ is selected from the group consisting of H, 1-C$_6$ alkyl, 1-C$_6$ alkoxy, hydroxy(C$_1$-C$_6$ alkyl), phenyl(C$_1$-C$_6$ alkyl), formyl, heteroaryl, heterocyclic, —COR$_6$, —OCOR$_6$, —COOR$_6$, —NR$_7$COR$_6$, —CONR$_7$R$_8$, and —(CH$_2$)$_n$—W, where W is cyano, hydroxy, C$_3$-C$_8$ cycloalkyl, —SO$_2$NR$_7$R$_8$, and —SO$_2$—R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl; R$_5$ is H, amino, C$_1$-C$_6$ alkyl-, or hydroxy(C$_1$-C$_6$ alkyl)-; R$_6$, R$_7$ and R$_8$ are each independently H, C$_1$-C$_6$ alkyl, C$_1$-C$_4$ alkoxy (C$_1$-C$_6$ alkyl), or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl; and, n is 1, 2 or 3. In a particular embodiment, the invention provides said compound wherein R" is C$_1$-C$_6$ alkyl and R$_5$ is H.

The invention also provides a compound having the structure (Ie):

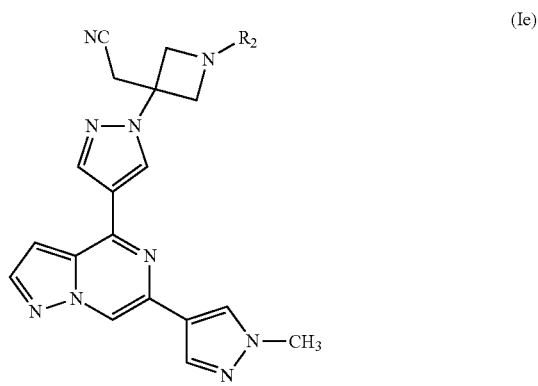

or a pharmaceutically acceptable salt thereof, or a pharmaceutically acceptable solvate of said compound or pharmaceutically acceptable salt, wherein: R$_2$ is selected from the group consisting of H, C$_1$-C$_6$ alkyl-, C$_1$-C$_6$ alkoxy-, hydroxy (C$_1$-C$_6$ alkyl)-, phenyl(C$_1$-C$_6$ alkyl)-, formyl, heteroaryl, heterocyclic, —COR$^8$, —OCOR$^6$, —COOR$^6$, —CONR$^7$R$^8$, and —(CH$_2$)$_n$—W, where W is cyano, hydroxy, C$_3$-C$_8$ cycloalkyl, —SO$_2$NR$^7$R$^8$, and —SO$_2$—R', where R' is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl; R$_6$, R$_7$ and R$_8$ are each are each independently H, C$_1$-C$_6$ alkyl-, C$_1$-C$_4$ alkoxy(C$_1$-C$_6$ alkyl)- or C$_3$-C$_8$ cycloalkyl said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl; and, n is 1, 2 or 3. In a particular embodiment, the invention provides said compound wherein R$_2$ is —(CH$_2$)$_n$—W, where W is cyano and n is 1, 2 or 3.

The invention also provides a compound having the structure (If):

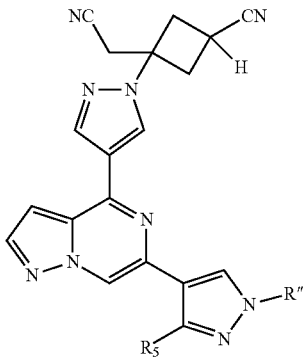

(If)

or a pharmaceutically acceptable salt thereof, or a pharmaceutically acceptable solvate of said compound or pharmaceutically acceptable salt, wherein: R" is H, —$COR_6$, —$CONR_7R_8$, $C_1$-$C_6$ alkyl-, or hydroxy($C_1$-$C_6$ alkyl)-; $R_5$ is H, amino, $C_1$-$C_6$ alkyl-, or hydroxy($C_1$-$C_6$ alkyl)-; $R_6$, $R_7$ and $R_8$ are each are each independently H, $C_1$-$C_6$ alkyl-, $C_1$-$C_4$ alkoxy($C_1$-$C_6$ alkyl)-, or $C_3$-$C_8$ cycloalkyl, said $C_1$-$C_6$ alkyl is optionally substituted by halo, CN or hydroxy; or, $R_7$ and $R_8$ together with the atom bonded thereto form a 5- or 6-membered ring, said ring being optionally substituted by halo, hydroxy, CN, or $C_1$-$C_6$ alkyl; and, n is 0, 1, 2 or 3. In a particular embodiment, the invention provides said compound wherein R" is $C_1$-$C_6$ alkyl. In another particular embodiment, the invention provides said compound wherein R" is methyl.

In certain preferred embodiments, the invention provides a compound selected from the group consisting of:
(1r,3r)-3-(4-(6-(3-amino-1-methyl-1H-pyrazol-4-yl)pyrazolo[1,5-a]pyrazin-4-yl)-1H-pyrazol-1-yl)-3-(cyanomethyl)cyclobutane-1-carbonitrile;
2,2'-(3-(4-(6-(1-methyl-1H-pyrazol-4-yl)pyrazolo[1,5-a]pyrazin-4-yl)-1H-pyrazol-1-yl)azetidine-1,3-diyl)diacetonitrile;
2-((1s,3r)-1-(4-(6-(5-(hydroxymethyl)-1H-pyrazol-3-yl)pyrazolo[1,5-a]pyrazin-4-yl)-1H-pyrazol-1-yl)-3-methoxycyclobutyl)acetonitrile;
5-(4-(1-((1s,3r)-1-(cyanomethyl)-3-methoxycyclobutyl)-1H-pyrazol-4-yl)pyrazolo[1,5-a]pyrazin-6-yl)-1H-pyrazole-3-carboxamide;
(1s,3s)-3-(cyanomethyl)-3-(4-(6-(5-(hydroxymethyl)isoxazol-3-yl)pyrazolo[1,5-a]pyrazin-4-yl)-1H-pyrazol-1-yl)cyclobutane-1-carbonitrile;
(1r,3s)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile;
(1s,3s)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile;
(1r,3r)-3-(cyanomethyl)-3-(4-(3-methyl-6-(1-methyl-1H-pyrazol-4-yl)pyrazolo[1,5-a]pyrazin-4-yl)-1H-pyrazol-1-yl)cyclobutane-1-carbonitrile;
2-((1r,3s)-1-(4-(6-(3-amino-1H-pyrazol-5-yl)pyrazolo[1,5-a]pyrazin-4-yl)-1H-pyrazol-1-yl)-3-methoxycyclobutyl)acetonitrile;
(1r,3r)-3-(cyanomethyl)-3-(4-(6-(1-(hydroxymethyl)-1H-pyrazol-4-yl)pyrazolo[1,5-a]pyrazin-4-yl)-1H-pyrazol-1-yl)cyclobutane-1-carbonitrile; and,
2-(1-ethyl-3-(4-(6-(5-(hydroxymethyl)-1H-pyrazol-3-yl)pyrazolo[1,5-a]pyrazin-4-yl)-1H-pyrazol-1-yl)azetidin-3-yl)acetonitrile, or, a pharmaceutically acceptable salt thereof.

In a certain embodiment, the invention provides a compound which is (1r,3r)-3-(4-(6-(3-amino-1-methyl-1H-pyrazol-4-yl)pyrazolo[1,5-a]pyrazin-4-yl)-1H-pyrazol-1-yl)-3-(cyanomethyl)cyclo-butane-1-carbonitrile, or a pharmaceutically acceptable salt thereof.

In a certain embodiment, the invention provides a compound which is 2,2'-(3-(4-(6-(1-methyl-1H-pyrazol-4-yl)pyrazolo[1,5-a]pyrazin-4-yl)-1H-pyrazol-1-yl)azetidine-1,3-diyl)diacetonitrile, or a pharmaceutically acceptable salt thereof.

In a certain embodiment, the invention provides a compound which is 2-((1s,3r)-1-(4-(6-(5-(hydroxymethyl)-1H-pyrazol-3-yl)pyrazolo[1,5-a]pyrazin-4-yl)-1H-pyrazol-1-yl)-3-methoxycyclo-butyl)acetonitrile, or a pharmaceutically acceptable salt thereof.

In a certain embodiment, the invention provides a compound which is 5-(4-(1-((1s,3r)-1-(cyanomethyl)-3-methoxycyclobutyl)-1H-pyrazol-4-yl)pyrazolo[1,5-a]pyrazin-6-yl)-1H-pyrazole-3-carboxamide, or a pharmaceutically acceptable salt thereof.

In a certain embodiment, the invention provides a compound which is (1s,3s)-3-(cyanomethyl)-3-(4-(6-(5-(hydroxymethyl)isoxazol-3-yl)pyrazolo[1,5-a]pyrazin-4-yl)-1H-pyrazol-1-yl)cyclobutane-1-carbonitrile, or a pharmaceutically acceptable salt thereof.

In a certain embodiment, the invention provides a compound which is (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, or a pharmaceutically acceptable salt thereof.

In another certain embodiment, the invention provides a compound which is (1s,3s)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, or a pharmaceutically acceptable salt thereof.

In yet another embodiment, the invention provides a compound which is (1r,3r)-3-(cyanomethyl)-3-(4-(3-methyl-6-(1-methyl-1H-pyrazol-4-yl)pyrazolo[1,5-a]pyrazin-4-yl)-1H-pyrazol-1-yl)cyclobutane-1-carbonitrile, or a pharmaceutically acceptable salt thereof.

In a certain other embodiment, the invention provides a compound which is 2-((1r,3s)-1-(4-(6-(3-amino-1H-pyrazol-5-yl)pyrazolo[1,5-a]pyrazin-4-yl)-1H-pyrazol-1-yl)-3-methoxycyclobutyl)acetonitrile, or a pharmaceutically acceptable salt thereof.

In another certain embodiment, the invention provides a compound which is 2-(1-ethyl-3-(4-(6-(5-(hydroxymethyl)-1H-pyrazol-3-yl)pyrazolo[1,5-a]pyrazin-4-yl)-1H-pyrazol-1-yl)azetidin-3-yl)acetonitrile, or, a pharmaceutically acceptable salt thereof.

The invention further provides a pharmaceutical or a veterinary composition comprising a compound of formula I and Ia-f or a pharmaceutically acceptable salt thereof, and a pharmaceutically acceptable carrier.

The invention also provides a method of treating a disease or condition for which a Tyk2 inhibitor is indicated, in a subject in need of such treatment, comprising administering to the subject a therapeutically effective amount of a compound of formula I or Ia-f, or a pharmaceutically acceptable salt thereof, or a pharmaceutically acceptable solvate of said compound or salt.

The invention also provides a method for treating or preventing a disorder or condition selected from allergic rhinitis, nasal congestion, rhinorrhea, perennial rhinitis, nasal inflammation, asthma of all types, chronic obstructive pulmonary disease, chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, pulmonary vascular disease, pulmonary arterial hypertension, acute lung injury, bronchiectasis, sinusitis, allergic conjunctivitis, idiopathic pulmonary fibrosis or atopic dermatitis, comprising administering to the subject a therapeutically effective amount of a compound of formula I and Ia-f, or a pharmaceutically acceptable salt thereof, or a pharmaceutically acceptable solvate of said compound or salt.

The invention also provides a method of treating primary biliary cirrhosis comprising administering to the subject a therapeutically effective amount of a compound of formula I or Ia-f, or a pharmaceutically acceptable salt thereof, or a pharmaceutically acceptable solvate of said compound or salt.

The invention also provides a method of treating a disease or condition selected from inflammation, inflammation, autoimmune disease, systemic lupus erythematous, lupus nephritis, discoid lupus, cutaneous lupus, central nervous system lupus, rheumatoid arthritis, psoriatic arthritis, inflammatory bowel disease, Crohn's disease, ulcerative colitis, asthma, allergic asthma, Type I diabetes, polymyositis, dermatomyositis, type I interferonopathies including Aicardi-Goutières syndrome and other mendelian diseases of overexpression of type I interferon, multiple sclerosis, primary progressive multiple sclerosis, relapsing remitting multiple sclerosis, primary biliary cirrhosis also known as primary biliary cholangitis, primary sclerosing cholangitis, autoimmune hepatitis, non-alcoholic fatty liver disease, non-alcoholic steatohepatitis, psoriasis, dermatomyositis, scleroderma, atopic dermatitis, vitiligo, alopecia areata, spondylopathy, ankylosing spondylitis, Alzheimer's disease, neuro-inflammation comprising administering to the subject a therapeutically effective amount of a compound of formula I or Ia-f, or a pharmaceutically acceptable salt thereof, or a pharmaceutically acceptable solvate of said compound or salt.

The invention also provides a method of treating the symptoms of inflammatory or autoimmune disease, including pruritis and fatigue.

In certain embodiments, the therapeutically effective amount used in accord with the method is from 0.01 mg/kg of body weight/day to 100 mg/kg of body weight/day. In certain other embod-iments, the therapeutically effective amount used in accord with the method is wherein the therapeutically effective amount is from 0.1 mg/kg of body weight/day to 10 mg/kg of body weight/day.

Compounds of the invention that have the same molecular formula but differ in the nature or sequence of bonding of their atoms or the arrangement of their atoms in space are termed "isomers". Isomers that differ in the arrangement of their atoms in space are termed "stereoisomers". It will be appreciated by those skilled in the art that the compound of formula I can exist as cis- and trans-achiral diastereomers.

Included within the scope of the described compounds are all isomers (e.g., cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds. Stereoisomeric mixtures, e.g., mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands. The present invention includes all pharmaceutically acceptable isotopically-labelled compounds of formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula I, for example, those incorporating a radioactive isotope, are useful in drug and/or substrate tissue distribution studies. The radioactive isotopes tritium, i.e., $^{3}$H, and carbon-14, i.e., $^{14}$C, particularly useful for this purpose in view of their ease of incorporation and ready means of detection.

Substitution with heavier isotopes such as deuterium, i.e., $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, a can be useful in Positron Emission Topography (PET) studies for examining substrate receptor occupancy. Isotopically-labeled compounds of formula I can generally be prepared by conventional techniques known to those skilled in the art or by processes analogous to those described in the accompanying Examples and Preparations using an appropriate isotopically-labeled reagent in place of the non-labeled reagent previously employed.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutically acceptable salts of the compounds of formula I and Ia-f include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts. For a review on suitable salts, see *Handbook of Pharmaceutical Salts: Properties, Selection*, and Use by Stahl and Wermuth (Wiley-VCH, 2002).

Pharmaceutically acceptable salts of compounds of formula I and Ia-f may be prepared, respectively, by one or more of three methods: (i) by reacting the compound of formula I and Ia-f with the desired acid or base; (ii) by removing an acid- or base-labile protecting group from a suitable precursor of the compound of formula I and Ia-f or by ring-opening a suitable cyclic precursor, for example, a lactone or lactam, using the desired acid or base; or (iii) by converting one salt of the compound of formula I or Ia-f to another by reaction with an appropriate acid or base or by means of a suitable ion exchange column. All three reactions are typically carried out in solution. The resulting salt may precipitate out and be collected by filtration or may be recovered by evaporation of the solvent. The degree of ionization in the resulting salt may vary from completely ionized to almost non-ionized.

Pharmaceutical compositions of the present invention may be manufactured by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in *Remington's Pharmaceutical Sciences*, Mack Pub. Co., New Jersey (1991). The formulations of the invention can be designed to be short-acting, fast-releasing, long-acting, and sustained-releasing. Thus, the pharmaceutical formulations can also be formulated for controlled release or for slow release.

Pharmaceutical compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day It is to be understood that the dosages may vary depending upon the requirements of each subject and the severity of the disorders or diseases being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

The present invention also provides any of the uses, methods or compositions as defined above wherein the compound of formula I or Ia-f, or a pharmaceutically acceptable salt thereof, or pharmaceutically acceptable solvate of said compound or salt, is used in combination with another pharmacologically active compound, particularly one of the functionally-defined classes or specific compounds listed below. These agents may be administered as part of the same or separate dosage forms, via the same or different routes of administration, and on the same or different administration schedules according to standard pharmaceutical practice known to one skilled in the art.

Suitable agents for use in combination therapy with a compound of formula I or Ia-f, or a pharmaceutically acceptable salt thereof, or pharmaceutically acceptable solvate of said compound or salt, sulfasalazine, mesalazine, prednisone, azathioprine, infliximab, adalimumab, belimumab, becertolizumab, natalizumab, vedolizumab, hydrocortisone, budesonide, cyclosporin, tacrolimus, fexofenadine, 6-mercaptopurine, methotrexate, ursodeoxycholic acid, obeticholic acid, anti-histamines, rifampin, prednisone, methotrexate, azathioprine, cyclophosphamide, hydroxychloroquine, mofetil, sodium mycophenolate, tacrolimus, leflunomide, chloroquine and quinacrine, thalidomide, rituxan, NSAIDs, solumedrol, depomedrol and dexamethasone.

Other suitable agents for use in combination therapy with a compound of formula I or Ia-f, or a pharmaceutically acceptable salt thereof, or pharmaceutically acceptable solvate of said compound or salt, include: a 5-lipoxygenase activating protein (FLAP) antagonist; a leukotriene antagonist (LTRA) such as an antagonist of $LTB_4$, $LTC_4$, $LTD_4$, $LTE_4$, $CysLT_1$ or $CysLT_2$, e.g., montelukast or zafirlukast; a histamine receptor antagonist, such as a histamine type 1 receptor antagonist or a histamine type 2 receptor antagonist, e.g., loratidine, fexofenadine, desloratidine, levocetirizine, methapyrilene or cetirizine; an al-adrenoceptor agonist or an α2-adrenoceptor agonist, e.g., phenylephrine, methoxamine, oxymetazoline or methylnorephrine; a muscarinic M3 receptor antagonist, e.g. tiotropium or ipratropium; a dual muscarinic M3 receptor antagononist/β2 agonist; a PDE inhibitor, such as a PDE3 inhibitor, a PDE4 inhibitor or a PDE5 inhibitor, e.g., theophylline, sildenafil, vardenafil, tadalafil, ibudilast, cilomilast or roflumilast; sodium cromoglycate or sodium nedocromil; a cyclooxygenase (COX) inhibitor, such as a non-selective inhibitor (e.g., aspirin or ibuprofen) or a selective inhibitor (e.g. celecoxib or valdecoxib); a glucocorticosteroid, e.g., fluticasone, mometasone, dexamethasone, prednisolone, budesonide, ciclesonide or beclamethasone; an anti-inflammatory monoclonal antibody, e.g., infliximab, adalimumab, tanezumab, ranibizumab, bevacizumab or mepolizumab; a β2 agonist, e.g., salmeterol, albuterol, salbutamol, fenoterol or formoterol, particularly a long-acting β2 agonist; an intigrin antagonist, e.g., natalizumab; an adhesion molecule inhibitor, such as a VLA-4 antagonist; a kinin $B_1$ or $B_2$ receptor antagonist; an immunosuppressive agent, such as an inhibitor of the IgE pathway (e.g., omalizumab) or cyclosporine; a matrix metalloprotease (MMP) inhibitor, such as an inhibitor of MMP-9 or MMP-12; a tachykinin $NK_1$, $NK_2$ or $NK_3$ receptor antagonist; a protease inhibitor, such as an inhibitor of elastase, chymase or catheopsin G; an adenosine $A_{2a}$ receptor agonist; an adenosine $A_{1b}$ receptor antagonist; a urokinase inhibitor; a dopamine receptor agonist (e.g., ropinirole), particularly a dopamine D2 receptor agonist (e.g., bromocriptine); a modulator of the NFκB pathway, such as an IKK inhibitor; a further modulator of a cytokine signalling pathway such as an inhibitor of JAK kinase, syk kinase, p38 kinase, SPHK-1 kinase, Rho kinase, EGF-R or MK-2; a mucolytic, mucokinetic or anti-tussive agent; an antibiotic; an antiviral agent; a vaccine; a chemokine; an epithelial sodium channel (ENaC) blocker or Epithelial sodium channel (ENaC) inhibitor; a nucleotide receptor agonist, such as a P2Y2 agonist; a thromboxane inhibitor; niacin; a 5-lipoxygenase (5-LO) inhibitor, e.g., Zileuton; an adhesion factor, such as VLAM, ICAM or ELAM; a CRTH2 receptor ($DP_2$) antagonist; a prostaglandin $D_2$ receptor ($DP_1$) antagonist; a haematopoietic prostaglandin D2 synthase (HPGDS) inhibitor; interferon-β; a soluble human TNF receptor, e.g., Etanercept; a HDAC inhibitor; a phosphoinositotide 3-kinase gamma (PI3Kγ) inhibitor; a phosphoinositide 3-kinase delta (PI3Kδ) inhibitor; a CXCR-1 or a CXCR-2 receptor antagonist; an IRAK-4 inhibitor; and, a TLR-4 or TLR-9 inhibitor, including the pharmaceutically acceptable salts of the specifically named compounds and the pharmaceutically acceptable solvates of said specifically named compounds and salts.

Accordingly, the invention provides methods of treating or preventing a disease, condition or disorder associated with JAK in a subject, such as a human or non-human mammal, comprising administering an effective amount of one or more compounds described herein to the subject. Suitable subjects that can be treated include domestic or wild animals, companion animals, such as dogs, cats, horses and the like; livestock including, cows and other ruminants, pigs, poultry, rabbits and the like; primates, for example monkeys, such as rhesus monkeys and cynomolgus (also known as crab-eating or long-tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier.

Conditions in which selective targeting of the JAK pathway or modulation of the JAK kinases, particularlyTYK2, are contemplated to be therapeutically useful include, inter alia, arthritis, asthma, autoimmune diseases, cancers or tumors, diabetes, certain eye diseases, disorders or conditions, inflammation, intestinal inflammations, allergies or conditions, neurodegenerative diseases, psoriasis, and transplant rejection. Conditions which can benefit from selective inhibition of TYK2 are discussed in greater detail below.

Accordingly, the compound of formula I or Ia-f or its pharmaceutically acceptable salts and solvates, and pharmaceutical compositions thereof, can be used to treat a variety of conditions or diseases such as the following:

Arthritis, including rheumatoid arthritis, juvenile arthritis, and psoriatic arthritis;

Autoimmune or inflammatory diseases or disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, autoimmune hepatitis, primary sclerosing cholangitis, chronic aggressive hepatitis, non-alcoholic fatty liver disease, non-alcoholic steatohepatitis ulcerative colitis and membranous glomerulopathy, systemic lupus erythematosis, rheumatoid arthritis, psoriatic arthritis, Sjogren's syndrome, Reiter's syndrome, polymyositis, dermatomyositis, type I interferonopathies including Aicardi-Goutières syndrome and other mendelian diseases of overexpression of type I interferon systemic sclerosis, polyarteritis nodosa, multiple sclerosis, relapsing remitting multiple sclerosis, primary progressive multiple sclerosis, secondary progressive multiple sclerosis, and bullous pemphigoid, and additional autoimmune diseases, which can be O-cell (humoral) based or T-cell based, including Cogan's syndrome, ankylosing spondylitis, Wegener's granulomatosis, autoimmune alopecia, Type I or juvenile onset diabetes, or thyroiditis;

Cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, or angiogenic-associated disorders including solid tumors;

Diabetes, including Type I diabetes or complications from diabetes;

Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, or ocular neovascularization;

Intestinal inflammations, including Crohn's disease, ulcerative colitis, inflammatory bowel disease, celiac diseases, proctitis, eosinophilic gastroenteritis, or mastocytosis;

Neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, or platelet aggregation;

Skin diseases, conditions or disorders including atopic dermatitis, eczema, psoriasis, scleroderma, pruritus or other pruritic conditions, vitiligo, alopecia;

Allergic reactions including allergic dermatitis in mammal (including horse allergic diseases such as bite hypersensitivity), summer eczema, sweet itch in horses, heaves, inflammatory airway disease, recurrent airway obstruction, airway hyper-responsiveness, or chronic obstruction pulmonary disease;

Asthma and other obstructive airways diseases, including chronic or inveterate asthma, late asthma, bronchitis, bronchial asthma, allergic asthma, intrinsic asthma, extrinsic asthma, or dust asthma;

Transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation.

Chemical Synthesis

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

All of the derivatives of formula (I) can be prepared by the procedures described in the general methods presented below or by routine modifications thereof. The present invention also encompasses any one or more of these processes for preparing the derivatives of formula (I), in addition to any novel intermediates used therein. The person skilled in the art will appreciate that the following reactions may be heated thermally or under microwave irradiation.

It will be further appreciated that it may be necessary or desirable to carry out the transformations in a different order from that described in the schemes, or to modify one or more of the transformations, to provide the desired compound of the invention.

The routes below, including those mentioned in the Examples and Preparations, illustrate methods of synthesising compounds of formula (I). The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by RC Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by TW Greene and PGM Wuts, John Wiley and Sons, Inc. (1999); and "Protecting Groups" by P J, Kocienski, Georg Thieme Verlag (1994); and any updated versions of said standard works.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

In the general synthetic methods below, unless otherwise specified, the substituents are as defined above with reference to the compounds of formula (I) above.

Where ratios of solvents are given, the ratios are by volume.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I).

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the derivatives of formula (I) can be prepared by the procedures described in the general methods presented below or by routine modifications thereof. The present invention also encompasses any one or more of these processes for preparing the derivatives of formula (I), in addition to any novel intermediates used therein. The person skilled in the art will appreciate that the following reactions may be heated thermally or under microwave irradiation.

It will be further appreciated that it may be necessary or desirable to carry out the transformations in a different order from that described in the schemes, or to modify one or more of the transformations, to provide the desired compound of the invention. The schemes are representative of methods useful in synthesizing the compounds of the present invention. They are not to constrain the scope of the invention in any way.

According to a first process, compounds of formula I may be prepared from compounds of formulae (A), (B), (C) and (D), as illustrated by Scheme 1.

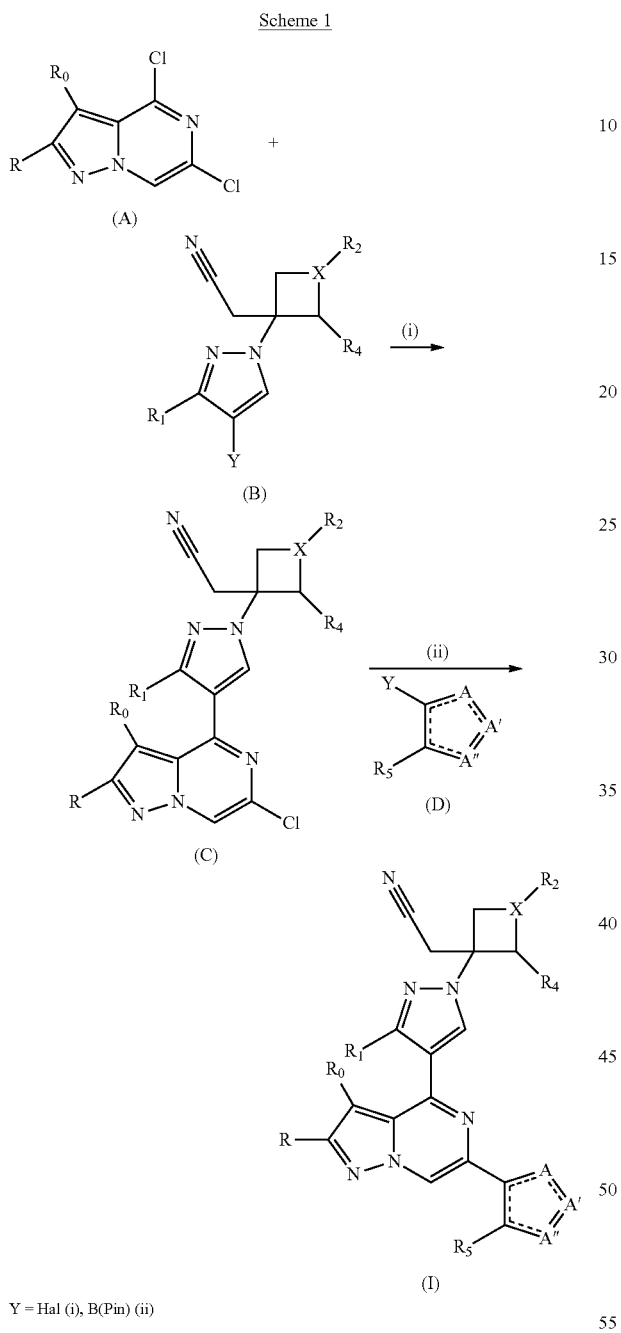

Y = Hal (i), B(Pin) (ii)

In scheme 1, compound of the Formula Bi (where Y=Hal) is converted to a compound of Formula Bii (Y=B(OR*)$_2$) by treatment with a suitable boronate such as B$_2$(Pin)$_2$, in the presence of a suitable base, such as K$_2$CO$_3$, and a suitable catalyst, such as Pd(dppf)Cl$_2$ in a suitable solvent, such as dioxane. A skilled person also knows that alternative organometallic coupling strategies can be used involving alternative coupling partners, metals and solvent combinations. A compound of the Formula Bii is prepared and isolated as described above or prepared in situ without isolation in a sequential cross-coupling strategy that is well understood by a skilled person. Thus, a compound of Formula Bii is cross-coupled with a compound of Formula A in the presence of a suitable catalyst, such as Pd(dppf)Cl$_2$, with a suitable base, such as K$_2$CO$_3$ in a suitable solvent such as dioxane at a suitable temperature from room temperature to reflux temperature. The resulting compound of Formula C is cross-coupled with a compound of the Formula D containing a suitable leaving group, such as Bu$_3$Sn or (Pin)$_2$B, with a suitable metal catalyst, such as Pd(PPh$_3$)$_4$, in a suitable solvent, such as MeCN at room or elevated temperatures.

According to a second process a compound of the Formula I is also be prepared by the organometallic cross-coupling reaction of compounds of the Formula F with compounds of Formula B, scheme 2.

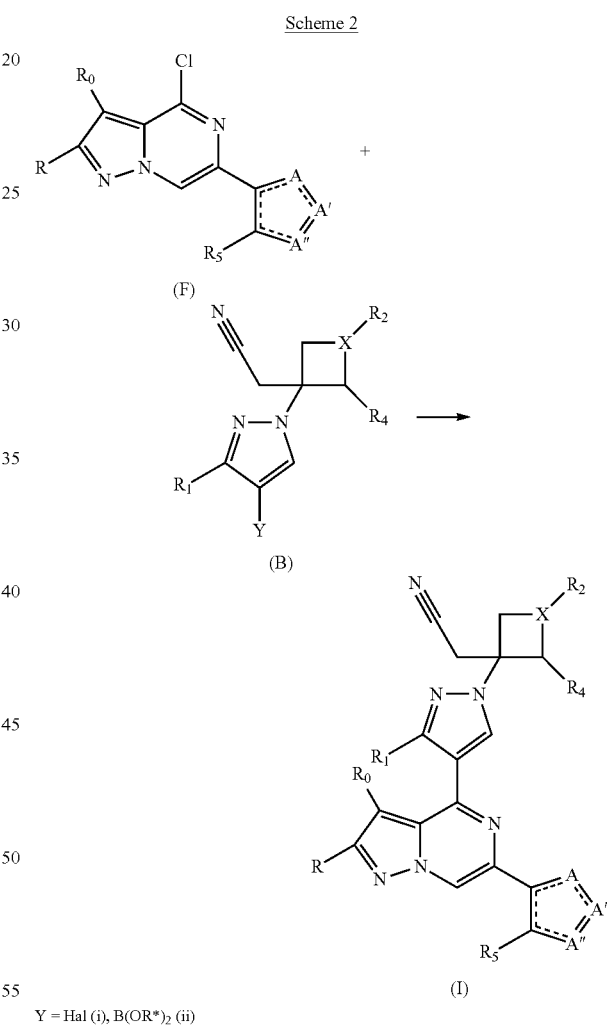

Y = Hal (i), B(OR*)$_2$ (ii)

Compound of the Formula Bi (where Y=Hal) is converted to a compound of Formula Bii (Y=B(OR*)$_2$) by treatment with a suitable boronate such as B(Pin)$_2$, in the presence of a suitable base, such as K$_2$CO$_3$, and a suitable catalyst, such as Pd(dppf)Cl$_2$ in a suitable solvent, such as dioxane. A skilled person also knows that alternative organometallic coupling strategies can be used involving alternative coupling partners, metals and solvent combinations. A compound of the Formula Bii is prepared and isolated as described above or prepared in situ without isolation in a sequential cross-coupling strategy that is well understood by a skilled person. Thus, a compound of Formula Bii is cross-coupled with a compound of Formula F in the presence of a suitable catalyst, such as Pd(dppf)Cl$_2$, with a suitable base, such as K$_2$CO$_3$ in a suitable solvent such as dioxane at a suitable temperature from room temperature to reflux temperature.

According to a third process, compound of Formula I is prepared by the alkylation, acylation, sulfonylation etc., of a compound of Formula G, Scheme 3.

Scheme 3

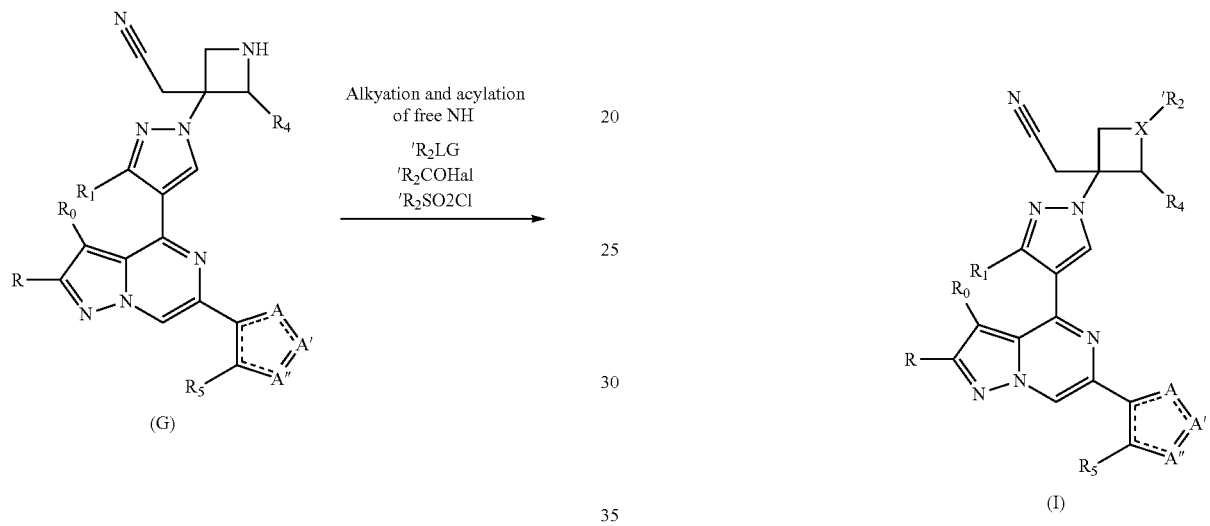

According to a Fourth process, compound of Formula I is prepared by the Michael addition of a compound of Formula H with a compound of Formula J in the presence of a suitable non-nucleophilic base, such as DBU in a suitable solvent, such as MeCN at a suitable temperature, scheme 4.

Scheme 4

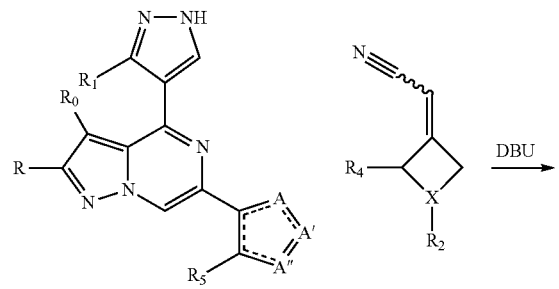

Scheme 5 illustrates a method for the preparation of compounds of Formula F. A diester of Formula Ei is treated with an alkylating agent of Formula K and a base such as K$_2$CO$_3$ in a suitable solvent such as MeCN. The resulting diester of Formula Eii is then cyclized in the presence NH$_4$OAc in a suitable solvent such as EtOH at elevated temperature to give bicyclic heterocyclic compound of Formula Eiii. The compound of Formula Eiii is hydrolysed to a compound of Formula Eiv with a suitable base, such as LiOH, in a suitable solvent such as MeOH. The resulting carboxylic acid of Formula Eiv is thermally decarboxylated in a suitable solvent, such as sulfolane at elevated temperature such as 280° C. The resulting compound of Formula Ev is chlorinated by treatment with a suitable reagent, such as POCl$_3$, in a suitable solvent, such as MeCN, at a suitable temperature such as reflux to prepare compounds of the Formula F.

Scheme 5

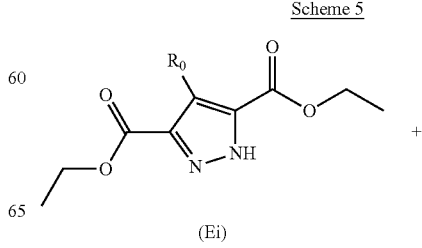

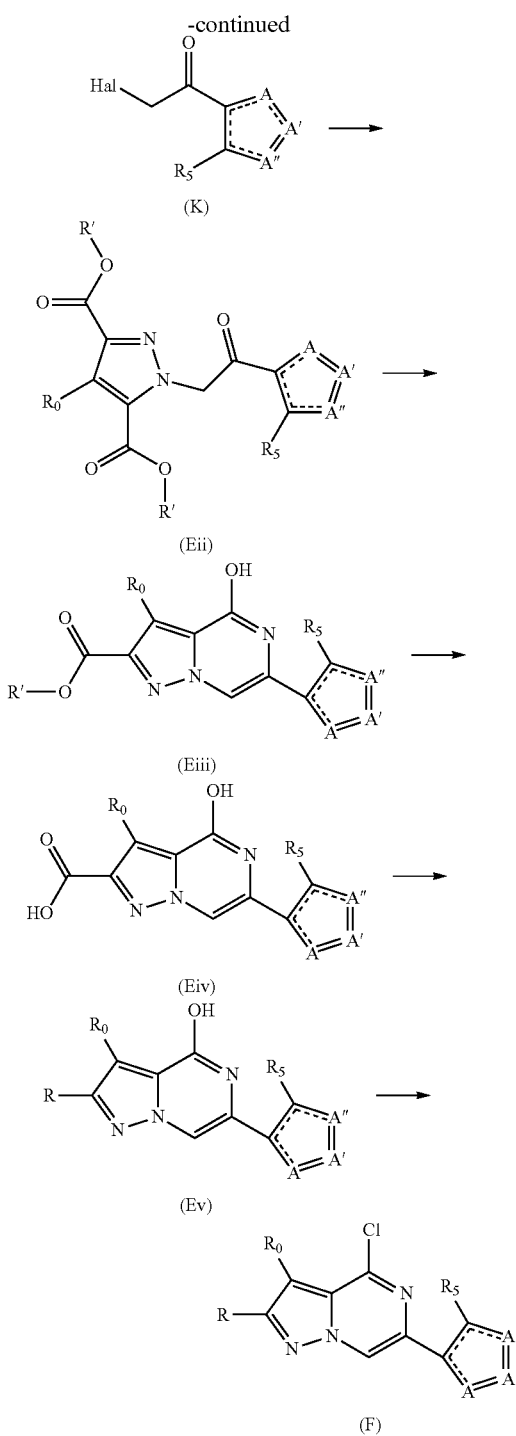

The following schemes and written descriptions provide general details regarding the preparation of the compounds of the invention. The compounds of the invention may be prepared by any method known in the art for the preparation of compounds of analogous structure. In particular, the compounds of the invention can be prepared by the procedures described by reference to the schemes that follow, or by the specific methods described in the examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I).

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in *Protective Groups in Organic Synthesis* by Theodora W. Greene and Peter G. M. Wuts, 3rd edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the derivatives of formula I and Ia-f can be prepared by the procedures described in the general methods presented below or by routine modifications thereof. The present invention also encompasses any one or more of these processes for preparing the derivatives of formula (I), in addition to any novel intermediates used therein. The person skilled in the art will appreciate that the following reactions may be heated thermally or under microwave irradiation.

In executing the synthesis of the compounds of the invention, one skilled in the art will recognize the need to sample and assay reaction mixtures prior to work up in order to monitor the progress of reactions and decide whether the reaction should be continued or whether it is ready to be worked up to obtain the desired product. Common methods for assaying reaction mixtures include thin-layer chromatography (TLC), liquid chromatography/mass spectroscopy (LCMS), and nuclear magnetic resonance (NMR).

One skilled in the art will also recognize that the compounds of the invention may be prepared as mixtures of diastereomers or geometric isomers (e.g., cis and trans substitution on a cycloalkane ring). These isomers can be separated by standard chromatographic techniques, such as normal phase chromatography on silica gel, reverse phase preparative high pressure liquid chromatography or supercritical fluid chromatography. One skilled in the art will also recognize that some compounds of the invention are chiral and thus may be prepared as racemic or scalemic mixtures of enantiomers. Several methods are available and are well known to those skilled in the art for the separation of enantiomers. A preferred method for the routine separation enantiomers is supercritical fluid chromatography employing a chiral stationary phase.

Experimental Section

Except where otherwise noted, reactions were run under an atmosphere of nitrogen.

Chromatography on silica gel was carried out using 250-400 mesh silica gel using pressurized nitrogen (~10-15 psi) to drive solvent through the column ("flash chromatography"). Where indicated, solutions and reaction mixtures were concentrated by rotary evaporation under vacuum.

The nomenclature in this patent is written as described by IUPAC (International Union of Pure and Applied Chemistry and using ChemBioDraw Ultra 13.0, Perkin Elmer to generate names.

The following non-limiting Preparations and Examples illustrate the preparation of compounds and salts of the present invention. In the Examples and Preparations that are set out below, and in the aforementioned Schemes, the following abbreviations, definitions and analytical procedures may be referred to. Other abbreviations common in the art may also be used. Standard IUPAC nomenclature has been used.
AcOH is acetic acid;
aq. is aqueous;
Boc is tert-butoxycarbonyl;
br is broad;
brine is a saturated solution of sodium chloride in water;
t-Bu is tert-butyl;
n-BuLi is n-butyllithium;
° C. is degrees celcius;
Cbz is carbobenzyloxy;
$CDCl_3$ is deutero-chloroform;
CDI is 1,1'-carbonyldiimidazole;
conc. is concentrated (in reference to reagents);
$Cs_2CO_3$ is cesium carbonate;
δ is chemical shift;
d is doublet;
DBU is 1,8-diazabicyclo[5.4.0]undec-7-ene;
DCM is dichloromethane;
DHP is 3,4-dihydro-2H-pyran;
DIPEA is N,N-diisopropylethylamine;
DMAP is 4-dimethylaminopyridine;
DMF is N,N-dimethylformamide;
DMSO is dimethyl sulfoxide;
$Et_2O$ is diethyl ether;
EtOAc is ethyl acetate;
EtOH is ethanol;
$(EtO)_2P(O)CH2CN$ is diethyl (cyanomethyl)phosphonate;
g is gram;
GCMS is gas chromatography mass spectrometry
HCl is hydrochloric acid;
$HCO_2H$ is formic acid;
HPLC is high performance liquid chromatography;
hrs is hours;
$H_2SO_4$ is sulfuric acid;
$K_2CO_3$ is potassium carbonate;
$KH_2PO_4$ is potassium dihydrogen phosphate
$K_2HPO_4$ is potassium monohydrogen phosphate;
$K_3PO_4$ is potassium phosphate (tribasic);
KOAc is potassium acetate
L is liter;
LCMS is liquid chromatography mass spectrometry;
LiBr is lithium bromide;
LiOH is lithium hydroxide;
m is multiplet;
M is molar;
MeCN is acetonitrile;
MeOH is methanol;
mg is milligram;
$MgSO_4$ is magnesium sulfate;
MHz is megaHertz;
min is minutes;
mL is milliliter;
mmol is millimole;
mol is mole;
MS m/z is mass spectrum ion peak;
MTBE is methyl t-butyl ether
$NaBH(OAc)_3$ is sodium triacetoxyborohydride;
$Na_2CO_3$ is sodium carbonate;
$NaHCO_3$ is sodium hydrogen carbonate;
$NaH_2PO_4$ is sodium dihydrogen phosphate;
$Na_2HPO_4$ is sodium monohydrogen phosphate;
NaI is sodium iodide;
$NaIO_4$ is sodium periodate;
NaOAc is sodium acetate;

NaOCl is sodium hypochlorite;
NaOH is sodium hydroxide;
$NH_3$ is ammonia;
$NH_4Cl$ is ammonium chloride;
$NH_4OH$ is ammonium hydroxide;
$NH_4OAc$ is ammonium acetate;
NMR is nuclear magnetic resonance;
$OsO_4$ is osmium tetroxide;
Pd/C is palladium on carbon;
$Pd(dppf)Cl_2$ is 1,1-bis(diphenylphosphino)ferrocene palladium(II)dichloride (CAS: 72287-26-4);
$Pd(dppf)Cl_2$ DCM is 1,1-bis(diphenylphosphino)ferrocene palladium(II)dichloride; complex with dichloromethane (CAS: 95464-05-4);
$Pd(OAc)_2$ is palladium acetate;
$Pd(PPh_3)_4$ is tetrakis(triphenylphosphine)palladium;
PMB-Cl is (4-methoxy)benzyl chloride;
$POCl_3$ is phosphorus(V) oxychloride;
ppm is parts per million;
psi is pounds per square inch;
PTSA is para-toluenesulfonic acid
$PyHBr_3$ is pyridine hydrobromide perbromide
PyHCl is pyridine hydrochloride
q is quartet;
Rt is retention time;
$Rh_2(OAc)_4$ is rhodium (II) acetate dimer;
$RuCl_3$ hydrate is ruthenium(II) chloride hydrate;
s is singlet;
$SOCl_2$ is thionyl chloride;
t is triplet;
TBAB is tetrabutylammonium bromide
TEA is triethylamine;
TFA is trifluoroacetic acid;
THF is tetrahydrofuran;
TMSCl is chorotrimethylsilane;
μL is microliter;
μmol is micromole
XPhos Pd G2 is chloro(2-dicyclohexylphosphino-2',4',6'-triisopropyl-1,1'-biphenyl)[2-(2'-amino-1,1'-biphenyl)]palladium(II); CAS 1310584-14-5.

$^1H$ Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common NMR solvents: $CD_3CN$, deuteroacetonitrile; $CDCl_3$, deuterochloroform; DMSO-$d_6$, deuterodimethylsulfoxide; and $CD_3OD$, deuteromethanol. Where appropriate, tautomers may be recorded within the NMR data; and some exchangeable protons may not be visible.

Mass spectra were recorded using electron impact ionization (EI), electrospray ionisation (ESI) or atmospheric pressure chemical ionisation (APCI). The observed ions are reported as MS m/z and may be positive ions of the compound [M]$^+$, compound plus a proton [MH]$^+$, or compound plus a sodium ion [MNa]$^+$. In some cases the only observed ions may be fragment ions reported as [MH-(fragment lost)]$^+$. Where relevant, the reported ions are assigned for isotopes of chlorine ($Cl^{35}$ and/or $^{37}Cl$), bromine ($^{79}Br$ and/or $^{81}Br$) and tin ($^{120}Sn$).

Wherein TLC, chromatography, or HPLC has been used to purify compounds, one skilled in the art may choose any appropriate solvent or combination of solvents to purify the desired compound. Chromatographic separations (excluding HPLC) were carried out using silica gel adsorbent unless otherwise noted.

All reactions were carried out using continuous stirring under an atmosphere of nitrogen or argon gas unless otherwise noted. In some cases, reactions were purged with nitrogen or argon gas prior to the start of the reaction. In these cases, the nitrogen or argon gas was bubbled through the liquid phase of the mixture for the approximate specified time. Solvents used were commercial anhydrous grades. All starting materials were commercially available products. In some cases, the Chemical Abstracts Service (CAS) identification number is provided to assist with clarity. In some cases, starting materials were prepared according to reported literature procedures as indicated by an asterisk (*). It will be apparent to one skilled in the art that the word "concentrated" as used herein generally refers to the practice of evaporation of solvent under reduced pressure, typically accomplished by the use of a rotary evaporator.

GCMS Conditions
Column: 12 m×0.2 mm, HP-1 Methyl Siloxane, 0.33 μm film, 1.0 ml/min column flow.
Methods: 7.6 min: Initial Oven Temp 105° C.; 0.1 min hold; 30° C./min ramp to 300° C. endpoint at 7.6 min; or 7.6 min: Initial Oven Temp 60° C.; 0.1 min hold; 40° C./min ramp to 320° C. endpoint at 7.6 min; or 5.1 min: Initial Oven Temp 40° C.; 0.1 min hold; 30° C./min ramp to 150° C. endpoint at 5.1 min.
GC Inlet Parameters: Front Inlet, Split 30:1, He, 8 psi pressure, 250° C. Injector, 33.9 ml/min total flow.
MSD Tune: 230° C. Source Temp, 150° C. Quad Temp, 280° C. Aux2 Temp Injection Volume: 1.0 μL
System Components: Agilent 5890 GC Oven with Agilent 5973 Mass Selective Detector
LCMS Conditions
Acid: Waters Acquity HSS T3, 2.1 mm×50 mm, C18, 1.7 μm; Column Temperature 60° C.
Base: Waters Acquity UPLC BEH, 2.1 mm×50 mm, C18, 1.8 μm; Column Temperature 60° C.
Mobile Phase: A: 0.1% formic acid in water (v/v); Mobile phase B: 0.1% formic acid in acetonitrile (v/v).
Mobile Phase A: 0.1% ammonia in water (v/v); Mobile phase B: 0.1% ammonia in acetonitrile (v/v)
Gradient Profiles: 1.5 min Run: Initial conditions: A-95%: B-5%; hold at initial from 0.0-0.1 min; Linear Ramp to A-5%:B-95% over 0.1-1.0 min; hold at A-5%:B-95% from 1.0-1.1 min; return to initial conditions 1.1-1.5 min
Purification Methods (PM)

The compounds of the Examples were purified according to one of the Purification Methods (PM) referred to below unless otherwise described:
Purification Method A: Preparative HPLC using [Agella venusil ASB C18 150×21.2 mm×5 μm, from 16% MeCN in water (0.225% formic acid) to 36% MeCN in water (0.225% formic acid)]
Purification Method B: Preparative HPLC using [Phenomenex Gemini C18 250×21.2 mm×8 um or 150 mm×25 mm×5 μm; from 16-55% MeCN in water (0.1% ammonia) to 36-60% MeCN in water (0.1% ammonia)]
Purification Method C: [YMC-Actus Triart C18 150×30 μm, from 24% MeCN in water (0.1% ammonia) to 44% MeCN in water (0.1% ammonia)]
Purification Method D: Preparative HPLC using [Phenomenex Gemini C18 250×21.2 mm×8 μm, from 25% MeCN in water (ammonia pH=10) to 45% MeCN in water (ammonia pH=10)] followed by chiral chromatography using AS 250× 25 mm I.D. 20 μM column, with supercritical CO₂: EtOH or IPA (0.05% aqueous ammonia) 70:30 at from 50-80 mL/min
Purification Method E: Preparative HPLC using [Phenomenex Gemini C18 250×21.2 mm×8 μm, from 25% MeCN in water (0.225% ammonia) to 45% MeCN in water (0.225% ammonia) followed by chiral chromatography using AD 250 mm×30 mm×20 μm column with mobile phase A: supercritical CO₂ and mobile phase B MeOH with 0.1% ammonia A:B 50:50 at 180 mL/min
Purification Method F: Silica gel column chromatography eluting with 100% DCM to 12% MeOH with 1% NH₄OH.
Purification Method G: Silica gel column chromatography eluting with 97:2:1 DCM:MeOH:NH₃ followed by preparative HPLC.
Purification Method H: Preparative HPLC using Column: Waters XBridge C18 19 mm×100 mm, 5μ; Mobile phase A: 0.03% ammonium hydroxide in water (v/v); Mobile phase B: 0.03% ammonium hydroxide in acetonitrile (v/v); from 5-20% B to 40-100% B at 25 mL/min flow rate.
Purification Method I: Preparative HPLC using Column: Waters Sunfire C18 19 mm×100 mm, 5μ; Mobile phase A: 0.05% TFA in water (v/v); Mobile phase B: 0.05% TFA in acetonitrile (v/v); from 20% B to 40% B at 6.75 minutes, then to 100% B at 7 minutes at 30 mL/min flow rate.
Specific Rotation Specific rotations based on the equation $[\alpha]=(100\cdot\alpha)/(l\cdot c)$ and are reported as unitless numbers where the concentration c is in g/100 mL and the path length l is in decimeters. The units of the specific rotation, (deg·mL)/(g·dm), are implicit and are not included with the reported value.

Preparation 1

Ethyl 1-(cyanomethyl)-1H-pyrazole-3-carboxylate

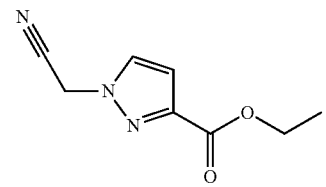

and

Ethyl 1-(cyanomethyl)-1H-pyrazole-5-carboxylate

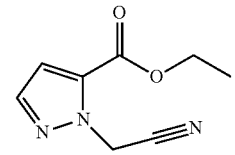

To a suspension of Cs₂CO₃ (2100 g, 6.44 mol) in DMF (12 L) was added ethyl 1H-pyrazole-3-carboxylate (750 g, 5.36 mol), followed by 2-chloroacetonitrile (450 g, 5.96 mol) and the mixture was stirred at about 25° C. for about 16 hrs. The reaction was poured into water (12 L) and extracted with EtOAc (5×5 L). The combined EtOAc extracts were washed with brine (2×5 L), dried (Na₂SO₄) and concentrated to afford a residue which was purified by chromatography to afford ethyl 1-(cyanomethyl)-1H-pyrazole-3-carboxylate (398 g, 39%) as a yellow oil and ethyl 1-(cyanomethyl)-1H-pyrazole-5-carboxylate (680 g). The ethyl 1-(cyanomethyl)-1H-pyrazole-5-carboxylate was dissolved in MTBE (15 L) and washed with brine (3×5 L), dried (Na$_2$SO$_4$) and concentrated to afford the compound as a yellow oil (489 g, 51%).

$^1$H NMR (400 MHz, CDCl$_3$) δ: 7.49 (s, 1H), 6.82 (s, 1H), 5.45 (s, 2H), 4.29 (q, 2H), 1.29 (t, 3H)

LCMS m/z=180.1 [MH]$^+$

Preparation 2

Ethyl 1-(2-amino-2-oxoethyl)-1H-pyrazole-5-carboxylate

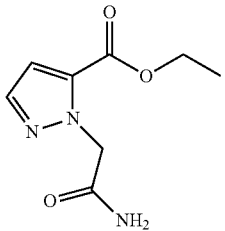

Two identical reactions were carried out in parallel.

To a solution of ethyl 1-(cyanomethyl)-1H-pyrazole-5-carboxylate (Preparation 1, 235.5 g, 1.32 mol) in TFA (1.2 L) was added conc. H$_2$SO$_4$ (377 mL, 7.04 mol) at about 25° C. The reaction mixture was stirred at about 25° C. for about 16 hrs before being combined with the parallel reaction and concentrated to remove most of the TFA. The residue was poured into ice-water (5 L) and extracted with EtOAc (5 L). The aqueous phase was further extracted with EtOAc (10×5 L) and the combined EtOAc extracts were washed with saturated aq. NaHCO$_3$ (2×10 L), dried (Na$_2$SO$_4$) and concentrated to afford the title compound as a yellow solid (477 g, 92%).

$^1$H NMR (400 MHz, CDCl$_3$) δ: 7.60 (s, 1H), 6.93 (s, 1H), 5.90 (br. s, 1H), 5.71 (br. s, 1H), 5.27 (s, 2H), 4.35 (q, 2H), 1.37 (t, 3H).

LCMS m/z=198.2 [MH]$^+$

Preparation 3

Pyrazolo[1,5-a]pyrazine-4,6(5H,7H)-dione

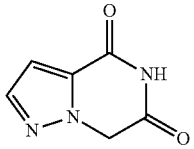 [SMILES: O=C1Cn2nccc2C(=O)N1]

To a solution of ethyl 1-(2-amino-2-oxoethyl)-1H-pyrazole-5-carboxylate (Preparation 2, 466 g, 2.17 mol) in EtOH (56 L) was added NaOtBu (498 g, 5.20 mol) in THF (4 L) at about 25° C. A white suspension developed during the addition and the mixture was then heated to about 70° C. for about 16 hrs. The reaction mixture was cooled to about 25° C. and acidified to about pH 6 with 12 M aq. HCl (500 mL), resulting in the formation of a white suspension. The mixture was concentrated to afford the title compound (admixed with sodium chloride) as yellow solid (783 g). This was used without further purification.

$^1$H NMR (400 MHz, DMSO-d$_6$) δ: 11.82 (s, 1H), 7.74 (s, 1H), 6.97 (s, 1H), 5.19 (s, 2H). LCMS m/z=152.1 [MH]$^+$

Preparation 4

4,6-Dichloropyrazolo[1,5-a]pyrazine

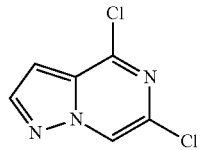 [SMILES: Clc1cn2nccc2c(Cl)n1]

Three identical reactions were carried out in parallel.

Pyrazolo[1,5-a]pyrazine-4,6(5H,7H)-dione (Preparation 3, 278 g, 1.14 mol) was added to POCl$_3$ (1.84 kg, 12 mol) at about 25° C., followed by PyHCl (131 g, 1.14 mol). The reaction mixture was heated at about 120° C. for about 16 hrs. The reactions were cooled to about 25° C. and concentrated to remove most of the POCl$_3$. Each residue was diluted with EtOAc (2 L) and the three EtOAc extracts were combined and poured into 1 M aq. NaH$_2$PO$_4$ (7.5 L) at about 25° C. and filtered through a pad of Celite®. The filter cake was washed with EtOAc (3×2 L) and all filtrates were combined and separated from the aqueous phase. The aqueous phase was extracted with MTBE (10 L). The combined EtOAc and MTBE extracts were washed with brine (2×5 L), dried (Na$_2$SO$_4$) and concentrated. The residue was purified by chromatography and the product was triturated with petroleum ether (300 mL) and filtered. The filter cake was dried to afford the title compound as a white solid (110 g, 22%).

$^1$H NMR (400 MHz, CDCl$_3$) δ: 8.42 (s, 1H), 8.06 (s, 1H), 6.93 (s, 1H).

LCMS m/z=189.8 [MH]$^+$ (Cl$^{37}$ isotope)

Preparation 5

1-(1-Methyl-1H-pyrazol-4-yl)ethan-1-one

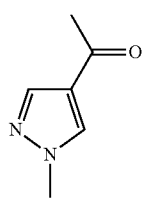

Two identical reactions were carried out in parallel.

To a mixture of 1-methylpyrazole (750 g, 9.16 mol) and acetic anhydride (1.7 kg, 16.67 mol) was added concentrated H$_2$SO$_4$ (75 g, 0.75 mol) at about 20° C. The reaction mixture was heated at about 150° C. for about 3 hrs. After cooling, the two mixtures were combined, poured into ice-water (15 L), adjusted to about pH 10 with 20% aq. NaOH and extracted with DCM (4×10 L). The combined DCM extracts were dried (Na$_2$SO$_4$) and concentrated to afford the title compound as a brown oil (1240 g, 72%).

¹H NMR (400 MHz, CDCl₃) δ: 7.86 (s, 1H), 7.84 (s, 1H), 3.92 (s, 3H), 2.40 (s, 3H).
GCMS m/z=109.0 [M−CH₃]⁺

Preparation 6

2-Bromo-1-(1-methyl-1H-pyrazol-4-yl)ethan-1-one

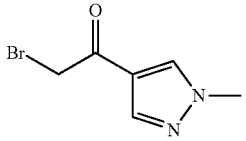

Two identical reactions were carried out in parallel.
To a solution of 1-(1-methyl-1H-pyrazol-4-yl)ethan-1-one (Preparation 5, 620 g, 5 mol) in DCM (12 L) and ethanol (3 L) was added PyHBr₃ (1.6 kg, 5 mol) at about 15° C. The mixture was stirred at about 15° C. for about 18 hrs. The two reaction mixtures were combined, quenched with water (10 L), separated, and the aqueous phase was extracted with DCM (4×10 L). The combined DCM extracts were dried (Na₂SO₄) and concentrated to remove about 69 L of solvent. The residue was diluted with petroleum ether (5 L), stirred at about 15° C. for about 30 min and the mixture was filtered. The precipitate was dried to afford the title compound as a yellow solid (1.73 kg, 85%).
¹H NMR (400 MHz, CDCl₃) δ: 7.97 (s, 1H), 7.91 (s, 1H), 4.17 (s, 2H), 3.93 (s, 3H).
LCMS m/z=203.1 [MH]⁺ (⁷⁹Br isotope)

Preparation 7

Diethyl 1-(2-(1-methyl-1H-pyrazol-4-yl)-2-oxoethyl)-1H-pyrazole-3,5-dicarboxylate

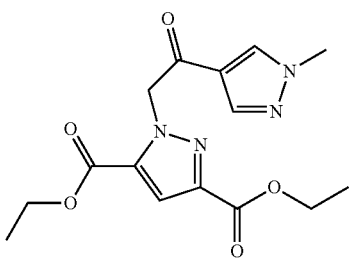 [SMILES: CCOC(=O)c1cc(C(=O)OCC)n(CC(=O)c2cnn(C)c2)n1]

Two reactions were carried out in parallel.
To a mixture of 2-bromo-1-(1-methyl-1H-pyrazol-4-yl)ethan-1-one (Preparation 6; 500 g, 2.46 mol) and diethyl-1H-pyrazole-3,5-dicarboxylate (580 g, 2.73 mol) in DMF (8 L) was added Cs₂CO₃ (1050 g, 3.23 mol) at about 20° C. After about 18 hrs, the two reaction mixtures were combined, diluted with water (10 L) and extracted with DCM (3×10 L). The combined DCM extracts were dried (Na₂SO₄) and concentrated. The residue was purified by chromatography to afford the title compound as a yellow solid (1.53 kg, 93%).
¹H NMR (400 MHz, CDCl₃) δ: 7.96 (s, 2H), 7.46 (s, 1H), 5.86 (s, 2H), 4.45 (q, 2H), 4.32 (q, 2H), 3.99 (s, 3H), 1.44 (t, 3H), 1.36 (t, 3H).
LCMS m/z=335.0 [MH]⁺

Preparation 8

Ethyl 4-hydroxy-6-(1-methyl-1H-pyrazol-4-yl)pyrazolo[1,5-a]pyrazine-2-carboxylate

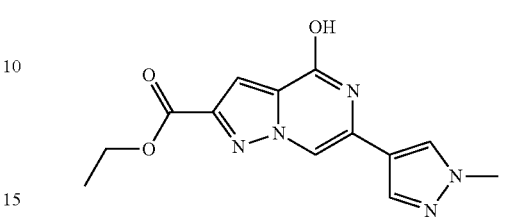

Three identical reactions were carried out in parallel.
To a solution of diethyl 1-(2-(1-methyl-1H-pyrazol-4-yl)-2-oxoethyl)-1H-pyrazole-3,5-dicarboxylate (Preparation 7; 510 g, 1.52 mol) in ethanol (6 L) was added NH₄OAc (352 g, 4.57 mol) at about 20° C. The mixture was heated in an autoclave at about 130° C. for about 24 hrs. The reaction mixtures were cooled to about 50° C. and were combined and filtered. The precipitate was dried to afford the title compound (1090 g, 83%) as an off-white solid.
¹H NMR (400 MHz, DMSO-d₆) δ: 11.35 (br. s, 1H), 8.31 (s, 1H), 8.20 (s, 1H), 8.05 (s, 1H), 7.38 (s, 1H), 4.34 (q, 2H), 3.89 (s, 3H), 1.33 (t, 3H).
LCMS m/z=288.0 [MH]⁺

Preparation 9

4-Hydroxy-6-(1-methyl-1H-pyrazol-4-yl)pyrazolo[1,5-a]pyrazine-2-carboxylic acid

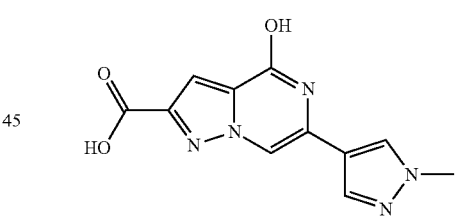

Two identical reactions were carried out in parallel.
To a suspension of ethyl 4-hydroxy-6-(1-methyl-1H-pyrazol-4-yl)pyrazolo[1,5-a]pyrazine-2-carboxylate (Preparation 8, 545 g, 1.9 mol) in MeOH (10 L) was added 1 M aq. NaOH (5.75 L) at about 20° C. After about 30 min, the suspension became a clear solution and stirring was continued at about 20° C. for about 18 hrs. The reaction mixtures were adjusted to about pH 2 with 12 M aq. HCl (650 mL), combined, and concentrated to remove most of the MeOH. The residue was filtered and the precipitate was dried to afford the title compound as an off-white solid (1040 g, 100%).
¹H NMR (400 MHz, DMSO-d₆) δ: 13.25 (br. s, 1H), 11.67 (s, 1H), 8.34 (s, 1H), 8.16 (s, 1H), 8.06 (s, 1H), 7.32 (s, 1H), 3.88 (s, 3H).
LCMS m/z=260.0 [MH]⁺

Preparation 10

6-(1-Methyl-1H-pyrazol-4-yl)pyrazolo[1,5-a]pyrazin-4-ol

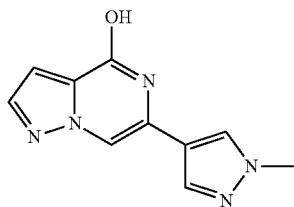 [SMILES: Cn1cc(-c2cn3nccc3c(O)n2)cn1]

Five identical reactions were carried out in parallel.

4-Hydroxy-6-(1-methyl-1H-pyrazol-4-yl)pyrazolo[1,5-a]pyrazine-2-carboxylic acid (Preparation 9, 85 g, 0.328 mol) was added in portions to pre-heated sulfolane (800 mL) at about 280° C. The five reaction mixtures were stirred at about 280° C. for about 2 hrs, cooled to about 25° C., and stirred for about 18 hrs. The reaction mixtures were combined and the mixture was purified by chromatography eluting with petroleum ether-EtOAc (10:1 to 0:1), followed by DCM-MeOH (10:1) to afford the title compound as a yellow solid (490 g, 75%).

$^1$H NMR (400 MHz, DMSO-d$_6$) δ: 11.45 (s, 1H), 8.28 (s, 1H), 8.10 (s, 1H), 8.04 (s, 1H), 7.88 (s, 1H), 6.99 (s, 1H), 3.88 (s, 3H).

LCMS m/z=216.0 [MH]$^+$

Preparation 11

4-Chloro-6-(1-methyl-1H-pyrazol-4-yl)pyrazolo[1,5-a]pyrazine

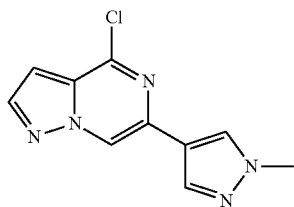 [SMILES: Cn1cc(-c2cn3nccc3c(Cl)n2)cn1]

Two identical reactions were carried out in parallel.

To a suspension of 6-(1-methyl-1H-pyrazol-4-yl)pyrazolo[1,5-a]pyrazin-4-ol (Preparation 10, 307 g, 1.43 mol) in MeCN (7.5 L) was added POCl$_3$ (2006 g, 13 mol) at about 25° C. The mixture was heated at about 85° C. for about 48 hrs. The reaction mixtures were combined and filtered. The precipitate was washed with EtOAc and dried under vacuum. The dried precipitate was purified by chromatography to afford a yellow solid which was dissolved in DCM (15 L) and washed with 1 M aq. NaHCO$_3$ (5 L). The DCM concentrated to remove about 13 L of solvent and the residue was diluted MTBE (2 L) and petroleum ether (2 L). The mixture was filtered and the precipitate was dried to afford the title compound as a yellow solid (385 g, 58%).

$^1$H NMR (400 MHz, DMSO-d$_6$) δ: 9.22 (s, 1H), 8.27 (s, 1H), 8.21 (s, 1H), 8.04 (s, 1H), 7.02 (s, 1H), 3.88 (s, 3H).

LCMS m/z=233.8 [MH]$^+$ (Cl$^{35}$ isotope)

Preparation 12

1-(4-Methoxybenzyl)-1H-pyrazole-4-carboxylic acid

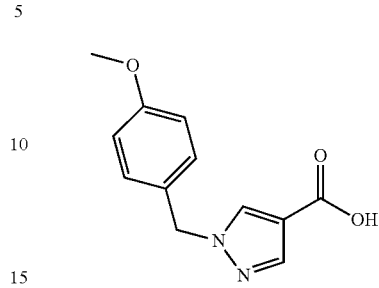

Part 1: Three identical reactions were carried out in parallel.

To a stirred solution of ethyl 1H-pyrazole-4-carboxylate (16 g, 110 mmol) in MeCN (160 mL) was added PMB-Cl (85.8 g, 548 mmol) and K$_2$CO$_3$ (23.7 g, 171 mmol) and the mixture was heated under reflux for about 18 hrs. The three batches were cooled, combined and filtered. The filtrate was concentrated to afford ethyl 1-(4-methoxybenzyl)-1H-pyrazole-4-carboxylate as a yellow oil that was used without further purification.

Part 2: Three identical reactions were carried out in parallel.

To a stirred solution of crude ethyl 1-(4-methoxybenzyl)-1H-pyrazole-4-carboxylate (Part 1, 50.0 g, 96 mmol) in THF (150 mL) and MeOH (150 mL) was added a solution of LiOH (10 g, 238 mmol) in water (75 mL). The mixture was heated at about 60° C. for about 18 hrs. The three batches were combined and evaporated to dryness. The residue was diluted with water (800 mL) and MeOH (150 mL) and washed with EtOAc (2×500 mL). The EtOAc extracts were discarded and the aqueous solution was acidified to about pH 2 with 6 M aq. HCl and extracted with EtOAc (2×800 mL). The combined EtOAc extracts were washed with brine (500 mL), dried (Na$_2$SO$_4$) and concentrated to afford the title compound as a white solid (33.0 g, 83% for the two steps).

$^1$H NMR (400 MHz, DMSO-d$_6$) δ: 12.34 (br. s, 1H), 8.32 (s, 1H), 7.79 (s, 1H), 7.23 (m, 2H), 6.89 (m, 2H), 5.26 (s, 2H), 3.72 (s, 3H).

Preparation 13

1-(4-Methoxybenzyl)-1H-pyrazole-4-carbonyl chloride

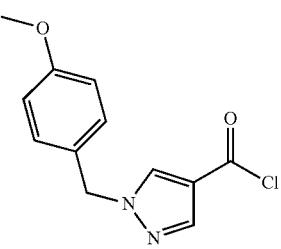 [SMILES: COc1ccc(Cn2cc(C(=O)Cl)cn2)cc1]

A solution of 1-(4-methoxybenzyl)-1H-pyrazole-4-carboxylic acid (Preparation 12, 25.0 g, 110 mmol) in SOCl$_2$ (40 mL) was stirred at about 60° C. for about 5 hrs. The solution was concentrated to afford title compound as a brown oil (27.0 g, 100%) which was used without further purification or characterization.

Preparation 14

N-Methoxy-1-(4-methoxybenzyl)-N-methyl-1H-pyrazole-4-carboxamide

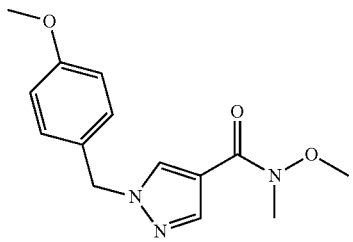

To a solution of N,O-dimethylhydroxylamine hydrochloride (26.3 g, 269 mmol) and TEA (131.0 g, 1.29 mol) in DCM (200 mL) was slowly added a solution of 1-(4-methoxybenzyl)-1H-pyrazole-4-carbonyl chloride (Preparation 13, 27.0 g, 108 mmol) in DCM (50 mL). After the addition was complete, the reaction mixture was stirred at about 20° C. for about 5 hrs. The mixture was diluted with DCM (150 mL) and water (300 mL). The combined DCM extracts were washed with brine, dried (Na$_2$SO$_4$) and concentrated to afford the title compound (20.0 g, 67%) as a brown oil which was used without further purification.

$^1$H NMR (400 MHz, CDCl$_3$) δ: 7.99 (s, 1H), 7.90 (s, 1H), 7.22 (d, 2H), 6.89 (d, 2H), 5.25 (s, 2H), 3.81 (s, 3H), 3.69 (s, 3H), 3.31 (s, 3H).

LCMS m/z=275.0 [MH]$^+$

Preparation 15

1-(1-(4-Methoxybenzyl)-1H-pyrazol-4-yl)ethan-1-one

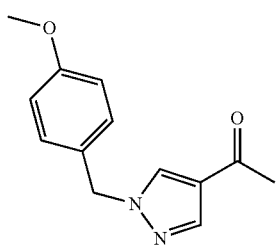 [SMILES: COc1ccc(Cn2cc(C(C)=O)cn2)cc1]

Two identical reactions were carried out in parallel.

To a solution of N-m ethoxy-1-(4-methoxybenzyl)-N-methyl-1H-pyrazole-4-carboxamide (Preparation 14, 10.0 g, 36.3 mmol) in THF (120 mL) was added dropwise 3 M methylmagnesium bromide in ether (24.2 mL) at about 0° C. The reaction mixture was warmed to about 25° C. and stirred for about 5 hrs. The reaction was quenched by the addition of saturated aq. NH$_4$Cl (100 mL) and extracted with EtOAc (2×200 mL). The combined EtOAc extracts were dried (Na$_2$SO$_4$) and concentrated. The concentrated residues from both experiments were combined and purified by chromatography to afford the title compound (10.0 g, 60%) as a brown solid.

$^1$H NMR (400 MHz, DMSO-d$_6$) δ: 8.47 (s, 1H), 7.91 (s, 1H), 7.25 (m, 2H), 6.90 (m, 2H), 5.27 (s, 2H), 3.72 (s, 3H), 2.34 (s, 3H).

LCMS m/z=231.7 [MH]$^+$

Preparation 16

2-Bromo-1-(1-(4-methoxybenzyl)-1H-pyrazol-4-yl)ethan-1-one

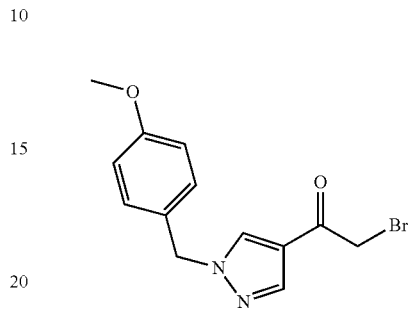

Two identical reactions were carried out in parallel.

To a solution of 1-(1-(4-methoxybenzyl)-1H-pyrazol-4-yl)ethan-1-one (Preparation 15, 8.0 g, 34.7 mmol) in DCM (96 mL) and EtOH (24 mL) was added PyHBr$_3$ (13.3 g, 41.7 mmol) at about 20° C. The reaction mixtures were kept at about 25° C. for about 18 hrs and quenched with water (100 mL) before being combined and extracted with EtOAc (2×300 mL). The combined EtOAc extracts were washed with brine, dried (Na$_2$SO$_4$) and concentrated. The residue was purified by chromatography to afford a yellow solid. This was triturated with MTBE (100 mL) to afford the title compound (15.0 g, 70%) as a yellow solid. An additional sample (5.0 g, 23%) of slightly impure product was obtained as a yellow solid by concentration of the trituration liquors.

$^1$H NMR (400 MHz, CDCl$_3$) δ: 7.99 (s, 1H), 7.89 (s, 1H), 7.23 (m, 2H), 6.92 (m, 2H), 6.92 (m, 2H), 5.25 (s, 2H), 4.15 (s, 2H), 3.81 (s, 3H).

LCMS m/z=333.0 [MNa]$^+$ ($^{81}$Br isotope)

Preparation 17

Dimethyl 1-(2-(1-(4-methoxybenzyl)-1H-pyrazol-4-yl)-2-oxoethyl)-1H-pyrazole-3,5-dicarboxylate

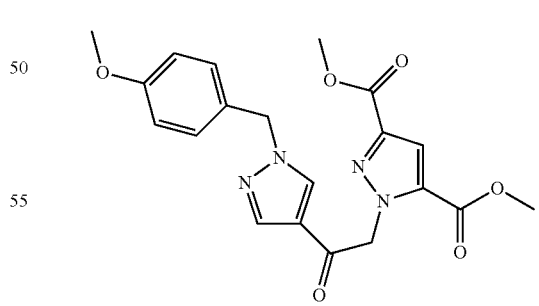

To a mixture of dimethyl 1H-pyrazole-3,5-dicarboxylate (1 g, 5 mmol) and 2-bromo-1-(1-(4-methoxybenzyl)-1H-pyrazol-4-yl)ethan-1-one (Preparation 16, 2.18 g, 7.06 mmol) in DMF (20 mL) was added Cs$_2$CO$_3$ (2.3 g, 7.06 mmol) at about 20° C. After about 2 days, the mixture was concentrated to dryness. The residue was dissolved in DCM and washed once with saturated aq. NH$_4$Cl. The DCM was concentrated and the residue was purified by chromatography. The product was stirred in EtOAc (20 mL) at about 20° C. for about 18 hrs. The solid formed was filtered and dried to afford the title compound (1.38 g, 60%).

$^1$H NMR (400 MHz, CDCl$_3$) δ: 7.96 (s, 1H), 7.82 (s, 1H), 7.42 (s, 1H), 7.24 (d, 2H), 6.93 (d, 2H), 5.80 (s, 2H), 5.27 (s, 2H), 3.95 (s, 3H), 3.84 (s, 3H), 3.83 (s, 3H).

LCMS m/z=413.1 [MH]$^+$

Preparation 18

Methyl 4-hydroxy-6-(1-(4-methoxybenzyl)-1H-pyrazol-4-yl)pyrazolo[1,5-a]pyrazine-2-carboxylate

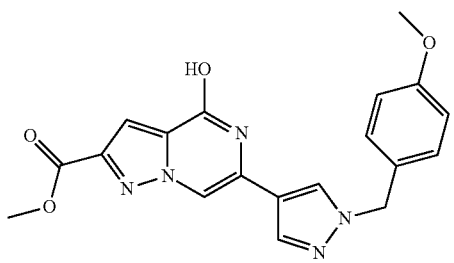 [SMILES: COC(=O)c1cc2c(O)nc(-c3cnn(Cc4ccc(OC)cc4)c3)cn2n1]

and

Ethyl 4-hydroxy-6-(1-(4-methoxybenzyl)-1H-pyrazol-4-yl)pyrazolo[1,5-a]pyrazine-2-carboxylate

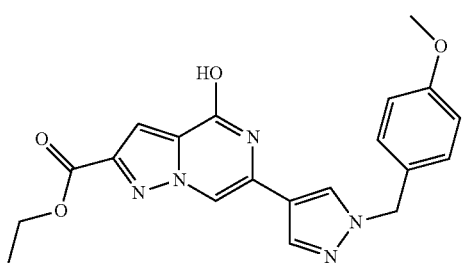 [SMILES: CCOC(=O)c1cc2c(O)nc(-c3cnn(Cc4ccc(OC)cc4)c3)cn2n1]

Six identical reactions were carried out in parallel.

To each of six vials was added dimethyl 1-(2-(1-(4-methoxybenzyl)-1H-pyrazol-4-yl)-2-oxoethyl)-1H-pyrazole-3,5-dicarboxylate (Preparation 17, 300 mg, 0.73 mmol), NH$_4$OAc (336 mg, 4.37 mmol) and EtOH (6 mL). The mixtures were heated under microwave irradiation at about 150° C. for about 2 hrs, then cooled to about 20° C., stirred for about 1 hrs, and filtered. The combined solids were dried to afford a mixture of both title compounds which was used without further purification in the next step (1.61 g).

$^1$H NMR (400 MHz, DMSO-d$_6$) δ: 11.65 (br. s., 1H), 8.38 (s, 1H), 8.17 (s, 1H), 8.07 (s, 1H), 7.36 (s, 1H), 7.26 (d, 2H), 6.93 (d, 2H), 5.75 (s, 1H), 5.28 (s, 2H), 3.86 (s, 3H), 3.74 (s, 3H). This is the methyl ester which was the major component.

LCMS m/z=380.1 [MH]$^+$, 394.1 [MH]$^+$

Preparation 19

4-Hydroxy-6-(1-(4-methoxybenzyl)-1H-pyrazol-4-yl)pyrazolo[1,5-a]pyrazine-2-carboxylic acid

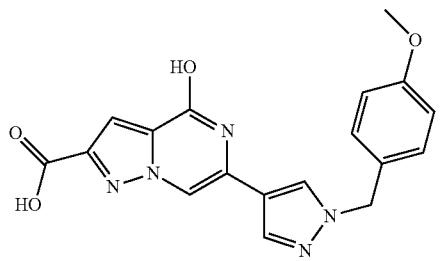 [SMILES: COc1ccc(Cn2cc(-c3cn4nc(C(=O)O)cc4c(O)n3)cn2)cc1]

To a solution of the mixture of methyl 4-hydroxy-6-(1-(4-methoxybenzyl)-1H-pyrazol-4-yl)pyrazolo[1,5-a]pyrazine-2-carboxylate and ethyl 4-hydroxy-6-(1-(4-methoxybenzyl)-1H-pyrazol-4-yl)pyrazolo[1,5-a]pyrazine-2-carboxylate (Preparation 18, 524 mg, about 1.38 mmol) in MeOH (10 mL) was added 1 M aq. NaOH (4.83 mL). The mixture was kept at about 20° C. for about 18 hrs before additional 1 M aq. NaOH (1.38 mL) was added. The mixture was kept at about 20° C. for about 24 additional hours. The MeOH was evaporated and the residue was diluted with water (2 mL) and stirred at about 40° C. until all solid was dissolved. The solution was acidified with 12 M aq. HCl and stirred at about 0° C. for about 10 min. The resulting precipitate was filtered and the precipitate was washed with water. The solid was dried under vacuum to afford the title compound (487 mg, 96%).

$^1$H NMR (400 MHz, DMSO-d$_6$) δ: 11.65 (s, 1H), 8.38 (s, 1H), 8.18 (m, 1H), 8.10 (s, 1H), 7.25-7.32 (m, 4H), 6.95 (m, 2H), 5.28 (s, 2H), 3.78 (s, 3H).

LCMS m/z=366.0 [MH]$^+$

Preparation 20

6-(1-(4-Methoxybenzyl)-1H-pyrazol-4-yl)42yrazole[1,5-a]42yrazole-4-ol

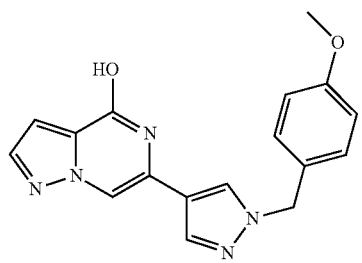 [SMILES: COc1ccc(Cn2cc(-c3cn4nccc4c(O)n3)cn2)cc1]

Three reactions were carried out in parallel.
Sample 1:

4-Hydroxy-6-(1-(4-methoxybenzyl)-1H-pyrazol-4-yl)42yrazole[1,5-a]pyrazine-2-carboxylic acid (Preparation 19, 40 mg, 0.11 mmol) was heated at about 350° C. for about 10 seconds until the off white solid melted and turned into dark brown liquid.

Sample 2:

4-hydroxy-6-(1-(4-methoxybenzyl)-1H-pyrazol-4-yl) 42yrazole[1,5-a]pyrazine-2-carboxylic acid (Preparation 19, 120 mg, 0.33 mmol) was heated at about 350° C. for about 15 seconds until the off white solid melted and turned into dark brown liquid.

Sample 3:

4-hydroxy-6-(1-(4-methoxybenzyl)-1H-pyrazol-4-yl) 42yrazole[1,5-a]pyrazine-2-carboxylic acid (Preparation 19, 310 mg, 0.85 mmol) was heated at about 350° C. for about 15 seconds until the off white solid all melted and turned into dark brown liquid.

All three batches were cooled, combined and concentrated twice with toluene to afford the title compound which was used without additional purification in the next step.

$^1$H NMR (400 MHz, DMSO-$d_6$) δ: 11.43 (s, 1H), 8.37 (s, 1H), 8.11 (s, 1H), 8.08 (s, 1H), 7.88 (d, 1H), 7.28 (d, 2H), 6.99 (d, 1H), 6.94 (d, 2H), 5.28 (s, 2H), 3.76 (s, 3H).

LCMS m/z=322.1 [MH]$^+$

Preparation 21

4-Chloro-6-(1-(4-methoxybenzyl)-1H-pyrazol-4-yl) pyrazolo[1,5-a]pyrazine

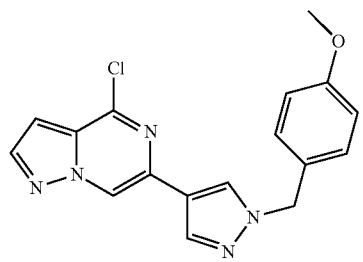 [SMILES: COc1ccc(Cn2cc(-c3cn4nccc4c(Cl)n3)cn2)cc1]

6-(1-(4-Methoxybenzyl)-1H-pyrazol-4-yl)pyrazolo[1,5-a]pyrazin-4-ol (Preparation 20, 390 mg, 1.21 mmol), PyHCl (143 mg, 1.21 mmol) and POCl$_3$ (10 mL) were heated at about 120° C. for about 18 hrs. The mixture was concentrated and the residue was treated with aq. NaH$_2$PO$_4$ solution to maintain about pH 4. The resulting solution was stirred at about 20° C. for about 10 min and extracted three times with DCM. The combined DCM extracts were dried and concentrated to afford the title compound as a brown solid (300 mg, 72%).

$^1$H NMR (400 MHz, CDCl$_3$) δ: 8.74 (s, 1H), 8.50 (s, 1H), 8.22 (m, 2H), 7.45 (m, 2H), 6.92-7.02 (m, 3H), 3.88 (s, 2H), 2.15 (s, 3H).

LCMS m/z=340.0 [MH]$^+$

Preparation 22 tert-Butyl 4-(6-chloropyrazolo[1,5-a]pyrazin-4-yl)-1H-pyrazole-1-carboxylate

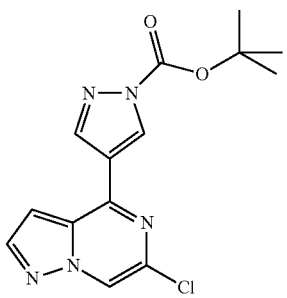 [SMILES: CC(C)(C)OC(=O)n1cc(-c2nc(Cl)cn3nccc23)cn1]

A solution of 4,6-dichloropyrazolo[1,5-a]pyrazine (Preparation 4, 700 mg, 3.72 mmol), tert-butyl 4-(4,4,5,5-tetramethyl-1,3,2-dioxaborolan-2-yl)-1H-pyrazole-1-carboxylate (1100 mg, 3.72 mmol), 2 M aq. K$_3$PO$_4$ (3 mL, 6 mmol) in 1,4-dioxane (10.0 mL) was purged with argon for about 5 min. To this was added bis(tri-t-butylphosphine) palladium(0) (96.1 mg, 0.19 mmol) and the reaction was kept at about 20° C. for about 18 hrs. The solvent was concentrated to afford an amber residue which was taken up in DCM and purified by chromatography to afford the title compound (710 mg, 60%).

$^1$H NMR (400 MHz, CDCl$_3$) δ: 8.82 (m, 1H), 8.44 (m, 3H), 8.14 (s, 1H), 1.60 (s, 9H).

LCMS m/z=220.1 [MH-BOC]$^+$

Preparation 23 tert-Butyl 4-(6-vinylpyrazolo[1,5-a]pyrazin-4-yl)-1H-pyrazole-1-carboxylate

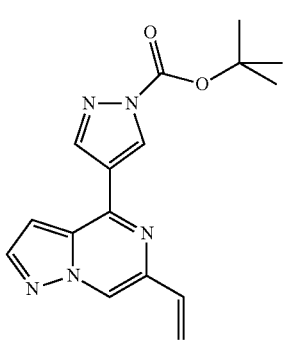 [SMILES: C=Cc1cn2nccc2c(-c2cnn(C(=O)OC(C)(C)C)c2)n1]

A solution of tert-butyl 4-(6-chloropyrazolo[1,5-a]pyrazin-4-yl)-1H-pyrazole-1-carboxylate (Preparation 22, 700 mg, 2.19 mmol) and tributyl(vinyl)stannane (694 mg, 2.19 mmol) in 1,4-dioxane (30 mL) was purged with argon for about 5 min followed by the addition of XPhos Pd G2 (344 mg, 0.44 mmol). The mixture was heated to about 55° C. for about 18 hrs. The mixture was concentrated and the residue was purified by chromatography to afford the title compound (449 mg, 66%).

$^1$H NMR (400 MHz, CDCl$_3$) δ: 8.79 (s, 1H), 8.46 (s, 1H), 8.26 (s, 1H), 8.07 (d, 1H), 6.95 (dd, 1H), 6.77 (dd, 1H), 6.43 (dd, 1H), 5.52 (dd, 1H), 1.74 (s, 9H).

LCMS m/z=312.3 [MH]$^+$

Preparation 24 tert-Butyl 4-(6-formylpyrazolo[1,5-a]pyrazine-4-yl)-1H-pyrazole-1-carboxylate

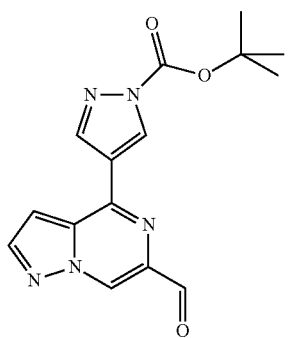 [SMILES: CC(C)(C)OC(=O)n1cc(-c2nc(C=O)cn3nccc23)cn1]

A solution of tert-butyl 4-(6-vinylpyrazolo[1,5-a]44yrazine-4-yl)-1H-pyrazole-1-carboxylate (Preparation 23; 446 mg, 1.43 mmol) and 2,6-lutidine (767 mg, 7.16 mmol) in 1,4-dioxane (9 mL) and water (3 mL) was cooled to about 0° C., and NaIO$_4$ (1530 mg, 7.16 mmol) and 4% aq. OsO$_4$ solution (0.54 mL) were added. The mixture was allowed to warm to about 20° C. for about 3 hrs. The solids were removed by filtration and washed with ether. The combined 1,4-dioxane and ether were concentrated and the residue was purified by chromatography to afford the title compound as an off white solid (289 mg, 65%).

$^1$H NMR (400 MHz, CDCl$_3$) δ: 10.20 (s, 1H), 9.01 (s, 1H), 8.85 (s, 1H), 8.50 (s, 1H), 8.30 (d, 1H), 7.08-7.12 (m, 1H), 1.73 (s, 9H).
LCMS m/z=314.2 [MH]$^+$

Preparation 25 tert-Butyl-4-(6-((hydroxyimino)methyl)45yrazine[1,5-a]45yrazine-4-yl)-1H-pyrazole-1-carboxylate

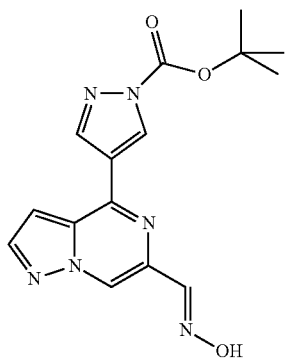 [SMILES: CC(C)(C)OC(=O)n1cc(-c2nc(/C=N/O)cn3nccc23)cn1]

Hydroxylamine HCl (112 mg, 1.58 mmol) was added to a mixture of tert-butyl 4-(6-formylpyrazolo[1,5-a]45yrazine-4-yl)-1H-pyrazole-1-carboxylate (Preparation 24, 450 mg, 1.44 mmol), and Na$_2$CO$_3$ (196 mg, 1.58 mmol) in MeOH (20 mL). The mixture was kept at about 20° C. for about 1.5 hrs. The mixture was concentrated, water (30 mL) was added, and the mixture was stirred for about 5 min before the solid was filtered and dried to yield the title compound as an off white solid (325 mg, 69%).

$^1$H NMR (400 MHz, CDCl$_3$) δ: 10.46 (br. s., 1H), 9.53 (s, 1H), 8.81 (s, 1H), 8.46 (s, 1H), 8.41 (s, 1H), 8.19 (d, 1H), 7.03 (d, 1H), 1.73 (s, 9H).
LCMS m/z=329.2 [MH]$^+$

Preparation 26

(3-(4-(1H-Pyrazol-4-yl)pyrazolo[1,5-a]pyrazin-6-yl)isoxazol-5-yl)methanol

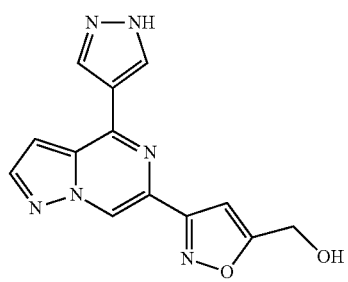 [SMILES: OCc1cc(-c2cn3nccc3c(-c3cn[nH]c3)n2)no1]

Sodium hypochlorite solution (about 12% to 15%, 0.19 mL about 3.0 mmol) was added dropwise to a solution of tert-butyl (E)-4-(6-((hydroxyimino)methyl)pyrazolo[1,5-a]pyrazin-4-yl)-1H-pyrazole-1-carboxylate (Preparation 25, 200 mg, 0.61 mmol) and propargyl alcohol (171 mg, 3.05 mmol) in DCM (5 mL) at about 0° C. The mixture was allowed to warm to about 20° C. for about 18 hrs. The resulting solid was filtered to afford the title compound (115 mg, 67%).

$^1$H NMR (400 MHz, DMSO-d$_6$) δ: 9.14 (s, 1H), 8.56 (s, 2H), 8.31 (d, 1H), 7.50 (d, 1H), 7.09 (s, 1H), 4.57-4.75 (m, 2H).
LCMS m/z=283.1 [MH]$^+$

Preparation 27

3-(Cyanomethylene)cyclobutane-1-carbonitrile

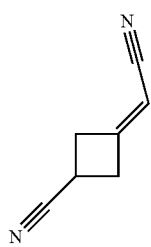

A solution of 3-oxocyclobutane-1-carbonitrile* (CAS: 20249-16-5, 14.5 g, 152 mmol) in THF (250 mL) was added to a mixture of (EtO)$_2$P(O)CH$_2$CN (31.1 g, 175 mmol), LiBr (19.9 g, 229 mmol) and TEA (30.9 g, 305 mmol) in THF (300 mL) at about 25° C. After about 16 hrs, the mixture was filtered and the filtrate was concentrated. The residue was purified by chromatography to afford the title compound as a light yellow oil (16.01 g, 89%).

*See *Synthetic Communications* 2005, 35, 657-662.

¹H NMR (400 MHz, CD₃CN) δ: 5.38 (s, 1H), 3.30-3.43 (m, 2H), 3.16-3.30 (m, 3H).

LCMS m/z=119.1 [MH]⁺

Example 1

(1s,3s)-3-(Cyanomethyl)-3-(4-(6-(5-(hydroxymethyl)isoxazol-3-yl)pyrazolo[1,5-a]pyrazin-4-yl)-1H-pyrazol-1-yl)cyclobutane-1-carbonitrile (cis isomer)

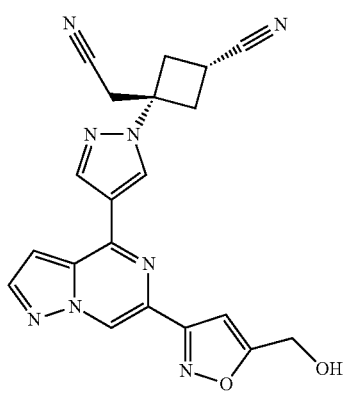 [SMILES: N#CC[C@]1(n2cc(-c3nc(-c4cc(CO)on4)cn4nccc34)cn2)C[C@@H](C#N)C1]

DBU (89.0 mg, 0.58 mmol) was added to a solution of (3-(4-(1H-pyrazol-4-yl)pyrazolo[1,5-a]pyrazin-6-yl)isoxazol-5-yl)methanol (Preparation 26; 55.0 mg, 0.19 mmol) and 3-(cyanomethylene)cyclobutane-1-carbonitrile (Preparation 27; 23.0 mg, 0.19 mmol) in MeCN (4 mL). The reaction was purged with nitrogen and stirred at about 20° C. for about 20 hrs. The mixture was partitioned between EtOAc (5 mL) and 1 M aq. NaH₂PO₄ (5 mL). The EtOAc was separated, dried (Na₂SO₄), and concentrated. The residue was purified chromatography afford the title compound (5 mg, 6%).

¹H NMR (400 MHz, DMSO-d₆) δ: 9.26 (m, 1H), 8.92 (m, 1H), 8.54 (m, 1H), 8.40 (m, 1H), 7.52 (m, 1H), 7.14 (m, 1H), 5.55 (br s, 1H), 4.70 (s, 2H), 3.60 (m, 3H), 3.42-3.45 (m, 2H), 2.78-2.83 (m, 2H).

LCMS m/z=401.4 [MH]⁺

Preparation 28 tert-Butyl 3-(cyanomethyl)-3-(4-(4,4,5,5-tetramethyl-1,3,2-dioxaborolan-2-yl)-1H-pyrazol-1-yl)azetidine-1-carboxylate

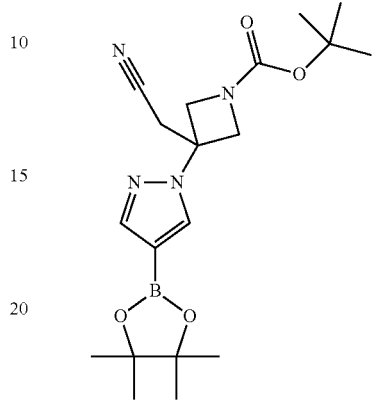

To a solution of tert-butyl 3-(cyanomethylene)azetidine-1-carboxylate (CAS 1153949-11-1, 7.00 g, 36.1 mmol) in MeCN (100 mL) was added 4-pyrazoleboronic acid pinacol ester (7.71 g, 39.7 mmol) and DBU (2.75 g, 18.0 mmol) at about 25° C. After about 18 hrs, the mixture was concentrated and the residue was purified column chromatography to afford the title compound as a white solid (11 g, 78%).

¹H NMR (400 MHz, CDCl₃) δ: 7.92 (s, 1H), 7.86 (s, 1H), 4.40 (m, 2H), 4.21 (m, 2H), 3.52 (s, 2H), 1.44 (s, 9H), 1.32 (s, 12H).

LC-MS m/z=333.0 [MH-C₄H₈]⁺

Preparation 29 tert-Butyl 3-(4-(6-chloropyrazolo[1,5-a]pyrazin-4-yl)-1H-pyrazol-1-yl)-3-(cyanomethyl)azetidine-1-carboxylate

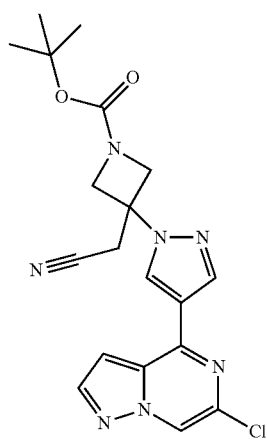 [SMILES: CC(C)(C)OC(=O)N1CC(CC#N)(n2cc(-c3nc(Cl)cn4nccc34)cn2)C1]

To a solution of tert-butyl 3-(cyanomethyl)-3-(4-(4,4,5,5-tetramethyl-1,3,2-dioxaborolan-2-yl)-1H-pyrazol-1-yl)azetidine-1-carboxylate (Preparation 28, 362 mg, 0.93 mmol) and 4,6-dichloropyrazolo[1,5-a]pyrazine (Preparation 4; 167 mg, 0.89 mmol) in 1,4-dioxane (5 mL) was added 2 M aq. K₃PO₄ (1.40 mL) at about 25° C. The mixture was purged with argon for about 2 min and bis(tri-t-butylphosphine)paladium(0) (94.3 mg, 0.184 mmol) was added. The mixture was stirred at about 20° C. for about 2 hrs. The mixture was diluted with DCM, separated, and the aqueous phase was extracted twice with DCM. The combined DCM extracts were dried (Na₂SO₄) and concentrated. The residue was purified by chromatography to afford the title compound as a white solid (295 mg, 75%).

¹H NMR (400 MHz, CDCl₃) δ: 8.42 (s, 1H), 8.41 (s, 1H), 8.31 (s, 1H), 8.10 (d, 1H), 7.02 (d, 1H), 4.54 (d, 2H), 4.31 (d, 3H), 3.33 (s, 2H), 1.49 (s, 9H).

LCMS m/z=358.1 [MH-C₄H₈]⁺

Preparation 30

2-(3-(4-(6-Chloropyrazolo[1,5-a]pyrazin-4-yl)-1H-pyrazol-1-yl)-1-(cyclopropyl methyl)azetidin-3-yl)acetonitrile

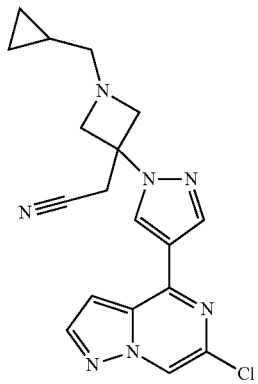 [SMILES: N#CCC1(n2cc(-c3nc(Cl)cn4nccc34)cn2)CN(CC2CC2)C1]

Part 1

To a solution of tert-butyl 3-(4-(6-chloropyrazolo[1,5-a]pyrazin-4-yl)-1H-pyrazol-1-yl)-3-(cyanomethyl)azetidine-1-carboxylate (Preparation 29, 0.56 g, 1.35 mmol) in DCM (13.5 mL) was added TFA (7 mL) at about 25° C. After about 4 hrs, the mixture was concentrated to dryness to afford 2-(3-(4-(6-chloropyrazolo[1,5-a]pyrazin-4-yl)-1H-pyrazol-1-yl)azetidin-3-yl)acetonitrile as a yellow solid (578 mg, about 100%) which was used without further purification.

Part 2

To a solution of 2-(3-(4-(6-chloropyrazolo[1,5-a]pyrazin-4-yl)-1H-pyrazol-1-yl)azetidin-3-yl)acetonitrile (Part 1, 1.35 mmol) and bromomethylcyclopropane (365 mg, 2.71 mmol) in DMF (13.5 mL) was added TEA (548 mg, 5.41 mmol) at about 25° C. The mixture was heated at about 50° C. for about 14 hrs. The cooled solution was diluted with water (20 mL) and extracted with EtOAc (3×20 mL). The combined EtOAc extracts were washed with brine (30 mL), dried (Na₂SO₄) and concentrated. The residue was purified by chromatography to afford the title compound as a yellow solid (314 mg, 63%).

¹H NMR (400 MHz, CDCl₃) δ: 8.39 (s, 1H), 8.37 (s, 1H), 8.27 (s, 1H), 8.08 (d, 1H), 7.02 (d, 1H), 3.78-3.84 (m, 2H), 3.59 (d, 2H), 3.42 (s, 2H), 2.45 (d, 2H), 0.77-0.87 (m, 1H), 0.48-0.55 (m, 2H), 0.14 (q, 2H).

LCMS m/z=367.9 [MH]⁺ (³⁵Cl isotope)

Preparation 31

Ethyl 3-(tri butylstannyl)-1H-pyrazole-5-carboxylate

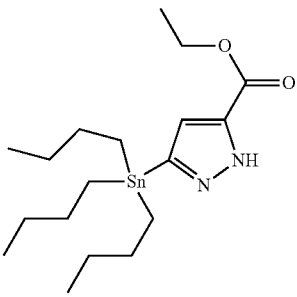 [SMILES: CCC[CH2][Sn]([CH2]CCC)([CH2]CCC)[c]1cc(C(=O)OCC)[nH]n1]

Ethynyltributylstannane (50 g, 158 mmol) was added to a solution of ethyldiazoacetate (19.9 g, 175 mmol) in toluene (500 mL) at about 25° C. The solution was heated for about 16 hrs at about 100° C., then was concentrated to afford the crude product as a yellow oil (110 g). This was combined with the crude product from an equivalent reaction carried out with ethynyltributylstannane (22 g, 70 mmol) and ethyldiazoacetate (8.76 g, 77 mmol), and the combined residues were purified by column chromatography on alumina to afford the title compound as a yellow oil (42 g, 61%).

¹H NMR (400 MHz, CDCl₃) δ: 10.28 (br. s., 1H), 6.84-6.99 (m, 1H), 4.41 (q, 2H), 1.47-1.67 (m, 6H), 1.41 (t, 3H), 1.28-1.39 (m, 6H), 1.04-1.24 (m, 6H), 0.90 (t, 9H).

LCMS m/z 431.2 [MH]⁺ (¹²⁰Sn isotope).

Preparation 32

(3-(Tributylstannyl)-1H-pyrazol-5-yl)methanol

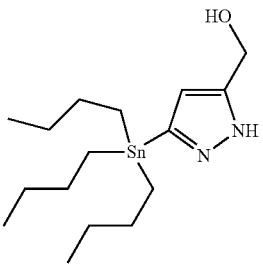 [SMILES: CCC[CH2][Sn]([CH2]CCC)([CH2]CCC)[c]1cc(CO)[nH]n1]

Ethyl 3-(tributylstannyl)-1H-pyrazole-5-carboxylate (Preparation 31, 6000 mg, 13.98 mmol) in THF (200 mL) was added to a stirred suspension of lithium aluminum hydride (3108 mg, 83.9 mmol) in THF (200 mL) at about −10° C. After about 4 hrs, the mixture was quenched with Na₂SO₄ decahydrate at about −10° C. until effervescence ceased. The mixture was filtered and the filter cake was washed with THF (500 mL) and DCM (5×500 mL). The combined filtrates were concentrated to afford the title compound as a white solid (4460 mg, 82%).

¹H NMR (400 MHz, CDCl₃) δ: 10.35 (br. s., 1H), 6.28-6.43 (m, 1H), 4.75 (s, 2H), 1.49-1.60 (m, 6H), 1.29-1.39 (m, 6H), 1.08-1.15 (m, 6H), 0.87-0.93 (m, 9H).

LCMS m/z=388.9 [MH]⁺ (¹²⁰Sn isotope)

Example 2

2-(1-(Cyclopropylmethyl)-3-(4-(6-(5-(hydroxymethyl)-1H-pyrazol-3-yl)pyrazolo[1,5-a]pyrazin-4-yl)-1H-pyrazol-1-yl)azetidin-3-yl)acetonitrile

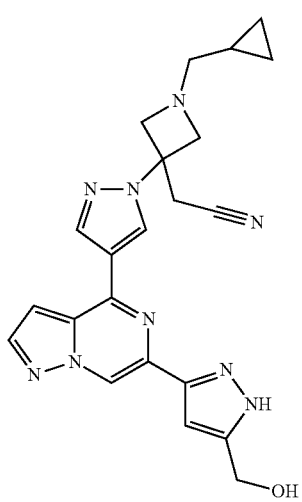 [SMILES: N#CCC1(n2cc(-c3nc(-c4cc(CO)[nH]n4)cn4nccc34)cn2)CN(CC2CC2)C1]

To a solution of 2-(3-(4-(6-chloropyrazolo[1,5-a]pyrazin-4-yl)-1H-pyrazol-1-yl)-1-(cyclopropylmethyl)azetidin-3-yl)acetonitrile (Preparation 30, 204 mg, 0.55 mmol) and 3-(tributylstannyl)-1H-pyrazol-5-yl)methanol (Preparation 32, 215 mg, 0.55 mmol) was added XPhos Pd G2 (43.6 mg, 0.055 mmol) in 1,4-dioxane (5.5 mL). The mixture was heated at about 110° C. for about 4 hrs. The mixture was evaporated to dryness and the residue was combined with the residue from an equivalent reaction using 2-(3-(4-(6-chloropyrazolo[1,5-a]pyrazin-4-yl)-1H-pyrazol-1-yl)-1-(cyclopropylmethyl)azetidin-3-yl)acetonitrile (Preparation 30, 110 mg, 0.27 mmol) and 3-(tributylstannyl)-1H-pyrazol-5-yl)methanol (Preparation 32, 105 mg, 0.27 mmol). The combined residues were purified by HPLC to afford the title compound (112 mg, 31%).

$^1$H NMR (400 MHz, CDCl$_3$) δ: 8.66 (s, 1H), 8.64-8.69 (m, 1H), 8.38 (s, 1H), 8.23 (s, 1H), 8.06 (d, 1H), 6.94 (d, 1H), 6.67 (s, 1H), 4.80 (s, 2H), 3.80 (d, 2H), 3.62 (d, 2H), 3.41 (s, 2H), 2.44 (d, 2H), 0.76-0.86 (m, 1H), 0.46-0.53 (m, 2H), 0.10-0.16 (m, 2H).

LCMS m/z 430.1 [MH]$^+$

Preparation 33

2-(3-(4-(6-Chloropyrazolo[1,5-a]pyrazin-4-yl)-1H-pyrazol-1-yl)azetidin-3-yl)acetonitrile

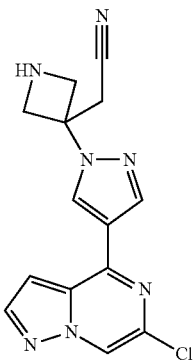 [SMILES: N#CCC1(n2cc(-c3nc(Cl)cn4nccc34)cn2)CNC1]

To a solution of tert-butyl 3-(4-(6-chloropyrazolo[1,5-a]pyrazin-4-yl)-1H-pyrazol-1-yl)-3-(cyanomethyl)azetidine-1-carboxylate (Preparation 29, 485 mg, 1.17 mmol) in DCM (20 mL) was added TFA (6 mL) at about 0° C. The mixture was stirred at about 25° C. for about 4 hrs. The solution was concentrated. The residue was adjusted to about pH 9 with conc. NH$_4$OH (about 0.5 mL) and partitioned between water (10 mL) and DCM (30 mL). The aqueous solution was extracted with DCM (3×30 mL). The combined DCM extracts were dried (Na$_2$SO$_4$) and concentrated to afford the title compound as a yellow solid (300 mg, 81%).

$^1$H NMR (400 MHz, CD$_3$OD) δ: 8.91 (s, 1H), 8.72 (s, 1H), 8.53 (s, 1H), 8.20 (d, 1H), 7.40 (d, 1H), 4.90 (d, 2H), 4.66 (d, 2H), 3.72 (s, 2H).

LCMS m/z 313.9 [MH]$^+$ ($^{35}$Cl isotope)

Preparation 34

2-(3-(4-(6-Chloropyrazolo[1,5-a]pyrazin-4-yl)-1H-pyrazol-1-yl)-1-ethylazetidin-3-yl)acetonitrile

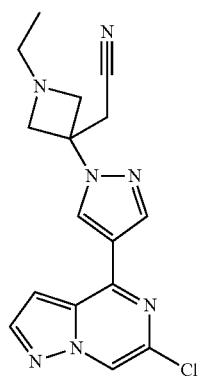 [SMILES: CCN1CC(CC#N)(n2cc(-c3nc(Cl)cn4nccc34)cn2)C1]

Sodium acetate (314 mg, 3.82 mmol) and acetaldehyde (842 mg, 19.1 mmol) were added to a solution of 2-(3-(4-(6-chloropyrazolo[1,5-a]pyrazin-4-yl)-1H-pyrazol-1-yl)azetidin-3-yl)acetonitrile (Preparation 33, 120 mg, 0.38 mmol) in MeOH (6 mL) and the mixture was stirred for about 4 hrs. Then NaBH(OAc)$_3$ (243 mg, 1.15 mmol) was added and the mixture was stirred for about 16 hrs longer at about 25° C. The mixture was concentrated and the residue was purified by chromatography to afford the title compound as a yellow solid (115 mg, 88%).

$^1$H NMR (400 MHz, CDCl$_3$) δ: 8.41 (s, 1H), 8.39 (s, 1H), 8.29 (s, 1H), 8.10 (d, 1H), 7.04 (d, 1H), 3.79 (d, 2H), 3.59 (d, 2H), 3.43 (s, 2H), 2.65 (q, 2H), 1.06 (t, 3H).

LCMS m/z=342.1 [MH]$^+$ (Cl$^{35}$ isotope)

Example 3

2-(1-Ethyl-3-(4-(6-(5-(hydroxymethyl)-1H-pyrazol-3-yl)pyrazolo[1,5-a]pyrazin-4-yl)-1H-pyrazol-1-yl)azetidin-3-yl)acetonitrile

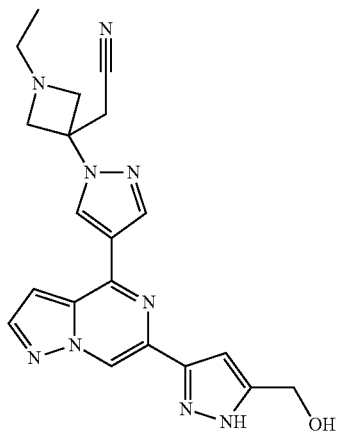 [SMILES: CCN1CC(CC#N)(n2cc(-c3nc(-c4cc(CO)[nH]n4)cn4nccc34)cn2)C1]

To a solution of 2-(3-(4-(6-chloropyrazolo[1,5-a]pyrazin-4-yl)-1H-pyrazol-1-yl)-1-ethylazetidin-3-yl)acetonitrile (Preparation 34, 100 mg, 0.29 mmol) in 1,4-dioxane (5 mL) was added 3-(tributylstannyl)-1H-pyrazol-5-yl)methanol (Preparation 32, 136 mg, 0.35 mmol) and XPhos Pd G2 (23.0 mg, 0.029 mmol). The mixture was heated at about 110° C. for about 16 hrs. The mixture was concentrated and the residue was purified by chromatography. The product was further purified by HPLC to afford the title compound as a yellow solid (59 mg, 46%).

$^1$H NMR (400 MHz, DMSO-d$_6$) δ: 13.21 (s, 0.5H), 12.93 (s, 0.5H), 9.23 (s, 0.5H), 9.07 (s, 1H), 8.6-8.89 (m, 1H), 8.69 (s, 0.5H), 8.47 (s, 0.5H), 8.26 (s, 1H), 7.47-7.53 (m, 1H), 6.-9-6.94 (m, 1H), 5.35 (s, 0.5H), 5.35 (s, 0.5H), 4.50-4.57 (m, 2H), 3.68-3.71 (m, 2H), 3.57-3.54 (m, 4H), 3.17-3.16 (m, 0.5H), 2.57-2.54 (m, 2H), 0.96-0.93 (m, 3H). This spectrum was consistent with the presence of distinguishable tautomers.

LCMS m/z=404.3 [MH]$^+$

Preparation 35

2-Cyclobutylideneacetonitrile

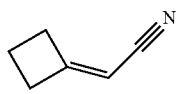

A mixture of (EtO)$_2$P(O)CH$_2$CN (4.48 g, 25.2 mmol), LiBr (1.96 g, 22.6 mmol) and TEA (2.28 g, 22.6 mmol) in dry THF (40 mL) was stirred at about 25° C. for about 2 hrs. To this was added a solution of cyclobutanone (1.58 g, 22.6 mmol) in THF (5 mL) at about 25° C. After about 16 hrs, the mixture was concentrated and the residue was purified by chromatography to afford the title compound as a colorless oil (1.2 g, 57%).

$^1$H NMR (400 MHz, CDCl$_3$) δ: 5.11 (quin), 2.93-3.05 (m), 2.82-2.92 (m), 2.04-2.17 (m).

Preparation 36

2-(1-(4-(4,4,5,5-Tetramethyl-1,3,2-dioxaborolan-2-yl)-1H-pyrazol-1-yl)cyclobutyl)acetonitrile

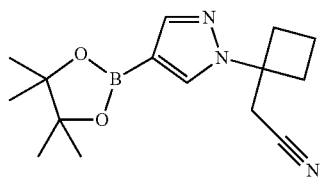 [SMILES: CC1(C)OB(c2cnn(C3(CC#N)CCC3)c2)OC1(C)C]

To a mixture of 2-cyclobutylideneacetonitrile (Preparation 35, 200 mg, 2.15 mmol) and 4-pyrazoleboronic acid pinacol ester (458 mg, 2.36 mmol) in MeCN (15 mL) was added DBU (981 mg, 6.44 mmol). The reaction was stirred at about 25° C. for about 16 hrs and then heated to about 50° C. for about 24 hrs. The mixture was concentrated and the residue was purified by chromatography to afford the title compound as a colorless oil (150 mg, 24%).

$^1$H NMR (400 MHz, CDCl$_3$) δ: m 7.89 (s, 1H), 7.86 (s, 1H), 3.09 (s, 2H), 2.68-2.80 (m, 2H), 2.45-2.55 (m, 2H), 2.01-2.10 (m, 2H), 1.33 (s, 12H).

LCMS m/z=287.9 [MH]$^+$

Example 4

2-(1-(4-(6-(1-Methyl-1H-pyrazol-4-yl)pyrazolo[1,5-a]pyrazin-4-yl)-1H-pyrazol-1-yl)cyclobutyl)acetonitrile

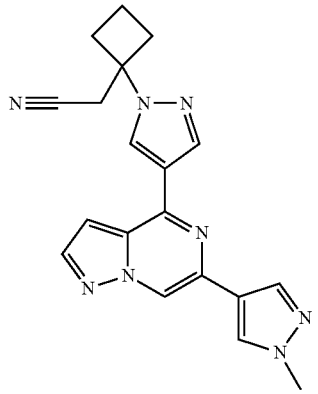 [SMILES: Cn1cc(-c2cn3nccc3c(-c3cnn(C4(CC#N)CCC4)c3)n2)cn1]

To a mixture of 2-(1-(4-(4,4,5,5-tetramethyl-1,3,2-dioxaborolan-2-yl)-1H-pyrazol-1-yl)cyclobutyl)acetonitrile (Preparation 36, 129 mg, 0.45 mmol) and 4-chloro-6-(1-methyl-1H-pyrazol-4-yl)pyrazolo[1,5-a]pyrazine (Preparation 11, 100 mg, 0.43 mmol) in 1,4-dioxane (4.3 mL) was added 2 M aq. K$_3$PO$_4$ (0.85 mL) and PdCl$_2$(dppf) (15.7 mg, 0.021 mmol). The mixture was purged with nitrogen for about 1 min and stirred at about 80° C. for about 16 hrs. The reaction mixture was combined with an equivalent reaction conducted using 2-(1-(4-(4,4,5,5-tetramethyl-1,3,2-dioxaborolan-2-yl)-1H-pyrazol-1-yl)cyclobutyl)acetonitrile (Preparation 36, 20 mg, 0.07 mmol) and 4-chloro-6-(1-methyl-1H-pyrazol-4-yl)pyrazolo[1,5-a]pyrazine (Preparation 11, 19. mg, 0.083 mmol), 2 M aq. $K_3PO_4$ (0.14 mL) and $PdCl_2$(dppf) (2.5 mg, 0.0035 mmol) in 1,4-dioxane (2 mL). The combined reaction mixtures were concentrated and the residue was purified by chromatography. The compound was further purified by HPLC to afford the title compound as a white solid (22 mg, 12%).

$^1$H NMR (400 MHz, $CD_3OD$) δ: 8.68 (s, 1H), 8.63 (s, 1H), 8.39 (s, 1H), 8.22 (s, 1H), 8.07 (d, 1H), 8.06 (s, 1H), 7.21 (d, 1H), 3.97 (s, 3H), 3.94-3.99 (m, 1H), 3.37 (s, 2H), 3.35-3.39 (m, 1H), 2.84-2.95 (m, 2H), 2.54 (ddd, 2H), 2.05-2.21 (m, 2H).

LCMS m/z=358.9 [MH]$^+$

Preparation 37

2-((1r,3s)-1-(4-Bromo-1H-pyrazol-1-yl)-3-methoxycyclobutyl)acetonitrile (trans isomer)

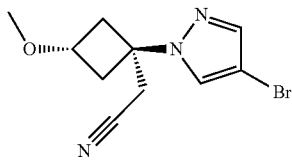

and 2-((1s,3r)-1-(4-Bromo-1H-pyrazol-1-yl)-3-methoxycyclobutyl)acetonitrile (cis isomer)

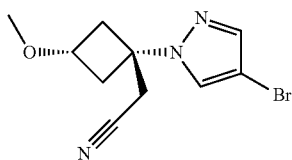

DBU (4.25 mL, 28.4 mmol) was added to a solution of 2-(3-methoxycyclobutylidene)acetonitrile (Preparation 90, 3.50 g, 28.4 mmol) and 4-bromopyrazole (4.18 g, 28.4 mmol) in MeCN (80 mL) at about 25° C. After about 18 hrs, the mixture was poured into $NaH_2PO_4$ (17.04 g, 142 mmol) in water and the phases were separated. The aqueous layer was extracted twice with EtOAc and the combined EtOAc extracts were concentrated. The excess 4-bromopyrazole was removed by chromatography eluting with DCM:THF (100:0 to 95:5). The material was further purified by chromatography eluting with ether:heptane to afford 2-((1r,3s)-1-(4-bromo-1H-pyrazol-1-yl)-3-methoxycyclobutyl)acetonitrile as a white solid (trans isomer, 2.19 g, 28%)

$^1$H NMR (400 MHz, $CDCl_3$) δ: 7.62 (s, 1H), 7.55 (s, 1H), 3.99 (tt, 1H), 3.30 (s, 3H), 3.12 (s, 2H), 2.96-3.04 (m, 2H), 2.44-2.51 (m, 2H).

LCMS m/z=270.0 [MH]$^+$ ($^{79}$Br isotope)

and 2-((1s,3r)-1-(4-bromo-1H-pyrazol-1-yl)-3-methoxycyclobutyl)acetonitrile as a colorless oil (cis isomer, 5.00 g, 65%).

$^1$H NMR (400 MHz, $CDCl_3$) δ: 7.60 (s, 1H), 7.53 (s, 1H), 4.00 (quin, 1H), 3.29 (s, 3H), 2.99 (s, 2H), 2.85-2.96 (m, 2H), 2.56-2.67 (m, 2H).

LCMS m/z=270.0 [MH]$^+$ ($^{79}$Br isotope)

Preparation 38

2-((1r,3s)-3-Methoxy-1-(4-(4,4,5,5-tetramethyl-1,3,2-dioxaborolan-2-yl)-1H-pyrazol-1-yl)cyclobutyl)acetonitrile

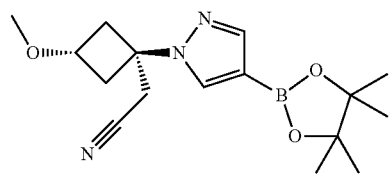

A mixture of 2-((1r,3s)-1-(4-bromo-1H-pyrazol-1-yl)-3-methoxycyclobutyl)acetonitrile (Preparation 37, trans isomer, 3399 mg, 12.58 mmol), bis(pinacolato)diboron (3510 mg, 13.8 mmol) and potassium acetate (3700 mg, 37.7 mmol) in 1,4-dioxane (33 mL) was purged with argon for about 5 min, followed by the addition of XPhos Pd G2 (1980 mg, 2.52 mmol) at about 25° C. The mixture was heated at about 65° C. for about 4 hrs. The mixture was concentrated and the residue was purified by chromatography to afford a solid. To this solid was added EtOAc (10 mL) and heptane (40 mL) and the mixture was stirred at about 25° C. for about 30 min. The solid was filtered and dried under vacuum to afford the title compound as a white solid (1.95 g, 49%).

$^1$H NMR (500 MHz, $CDCl_3$) δ: 7.91 (s, 1H), 7.87 (s, 1H), 3.98 (tt, 1H), 3.28 (s, 3H), 3.17 (s, 2H), 2.98-3.07 (m, 2H), 2.45-2.53 (m, 2H), 1.31 (s, 12H).

LCMS m/z=318.0 [MH]$^+$

Preparation 39

2-((1r,3s)-1-(4-(6-Chloropyrazolo[1,5-a]pyrazin-4-yl)-1H-pyrazol-1-yl)-3-methoxycyclobutyl)acetonitrile

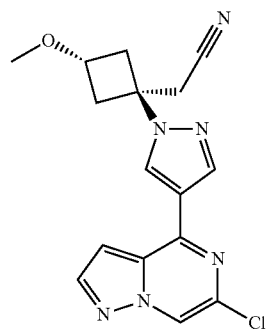 [SMILES: CO[C@H]1C[C@](CC#N)(n2cc(-c3nc(Cl)cn4nccc34)cn2)C1]

A solution of 2-((1r,3s)-3-methoxy-1-(4-(4,4,5,5-tetramethyl-1,3,2-dioxaborolan-2-yl)-1H-pyrazol-1-yl)cyclobutyl)acetonitrile (Preparation 38, 1950 mg, 6.15 mmol), 4,6- dichloropyrazolo[1,5-a]pyrazine (Preparation 4, 1160 mg, 6.15 mmol) and 2 M aq. $K_3PO_4$ (9.22 mL) in 1,4-dioxane (25 mL) was purged with argon for about 5 min followed by the addition of bis(tri-t-butylphosphine)palladium(0) (157 mg, 0.31 mmol) at about 25° C. After about 2 hrs, the mixture was diluted with EtOAc, the phases were separated and the aqueous phase was extracted twice with DCM. The combined EtOAc and DCM extracts were dried ($Na_2SO_4$) and concentrated to afford a solid that was recrystallized from a warm (about 40° C.) mixture of DCM and heptane to afford the title compound as an off-white solid (1.12 g, 53%). The filtrate was concentrated and purified by chromatography to afford additional title compound (1.01 g, 47%).

$^1$H NMR (500 MHz, $CDCl_3$) δ: m 8.39 (d, 1H), 8.38 (s, 1H), 8.28 (s, 1H), 8.09 (d, 1H), 7.03 (dd, 1H), 4.04-4.10 (m, 1H), 3.33 (s, 3H), 3.25 (s, 2H), 3.09-3.17 (m, 2H), 2.53-2.61 (m, 2H)

LCMS m/z=343.1 $[MH]^+$ ($Cl^{35}$ isotope)

Preparation 40

3,5-Dibromo-1-(tetrahydro-2H-pyran-2-yl)-1H-pyrazole

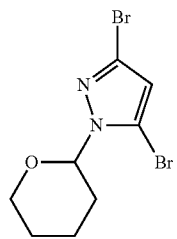 [SMILES: Brc1cc(Br)n(C2CCCCO2)n1]

To a solution of 3,5-dibromopyrazole* (CAS: 67460-86-0, 18.0 g, 79.7 mmol) and DHP (30 mL) was added $CF_3COOH$ (73 mg, 0.64 mmol). The mixture was heated at about 95° C. for about 12 hrs. The reaction was quenched with NaOH (96 mg, 2.4 mmol) and then concentrated. The residue was purified by chromatography to afford the title compound (11.5 g, 46%).

*See: *Justus Liebigs Annalen der Chemie* 1959, 625, 55-65.

$^1$H NMR (400 MHz, $CDCl_3$) δ: 6.35 (s, 1H), 5.42 (d, 1H), 4.05 (m, 1H), 3.65 (m, 1H), 2.38-2.48 (m, 1H), 2.11 (m, 1H), 1.90 (m, 1H), 1.62-1.77 (m, 3H).

LCMS m/z=226.7 $[MH-THP]^+$ ($^{79}Br$, $^{81}Br$ isotope)

Preparation 41

3-Bromo-1-(tetrahydro-2H-pyran-2-yl)-1H-pyrazole-5-carboxylic acid

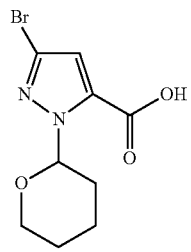

n-BuLi (2.5 M, 15.8 mL, 39.5 mmol) was added dropwise to a solution of 3,5-dibromo-1-(tetrahydro-2H-pyran-2-yl)-1H-pyrazole (Preparation 40, 9.4 g, 30.0 mmol) in THF (87 mL) at about −78° C. The mixture was kept at about −78° C. for about 2 hrs. A solution of $CO_2$ (prepared by bubbling $CO_2$ into anhydrous THF (100 mL) for 20 min at about −70° C. and stirring at that temperature for about 1.5 hrs) was added dropwise while maintaining the internal reaction temperature below about −65° C. The mixture was then stirred at about −70° C. for about 1 hr. The mixture was adjusted to about pH 4 with 1 M aq. HCl at about 0° C. and was extracted with EtOAc (3×100 mL). The combined EtOAc extracts were washed with brine (2×50 mL), dried ($Na_2SO_4$) and concentrated. The residue was purified by chromatography to afford the title compound as a yellow solid (5.0 g, 60%).

$^1$H NMR (400 MHz, DMSO-$d_6$) δ: 6.99 (s, 1H), 6.17 (dd, 1H), 3.90 (d, 1H), 3.49-3.66 (m, 2H), 2.12-2.28 (m, 1H), 1.91-2.04 (m, 1H), 1.83-1.92 (m, 1H), 1.58-1.70 (m, 1H), 1.45-1.57 (m, 2H).

Preparation 42 tert-Butyl (3-bromo-1-(tetrahydro-2H-pyran-2-yl)-1H-pyrazol-5-yl)carbamate

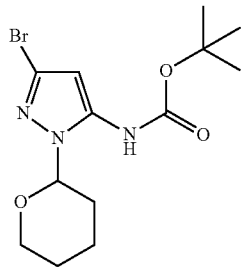 [SMILES: CC(C)(C)OC(=O)Nc1cc(Br)nn1C1CCCCO1]

Diphenylphosphoryl azide (10 g, 36.4 mmol) was added to a solution of 3-bromo-1-(tetrahydro-2H-pyran-2-yl)-1H-pyrazole-5-carboxylic acid (Preparation 41, 5 g, 18.17 mmol) and DIPEA (6.4 mL, 37.0 mmol) in t-butanol (60.6 mL). The mixture was heated at about 45° C. for about 30 min, and then heated under reflux for about 5 hrs. The mixture was diluted with EtOAc (300 mL) and washed with saturated aq. $NaHCO_3$ (3×100 mL), brine (2×100 mL), dried ($Na_2SO_4$) and concentrated. The residue was purified by chromatography to afford the title compound as a light yellow oil (3.36 g, 53%).

$^1$H NMR (400 MHz, DMSO-$d_6$) δ: 9.64 (br. s., 1H), 6.26 (s, 1H), 5.44 (dd, 1H), 3.84 (d, 1H), 3.55-3.70 (m, 1H), 2.08-2.20 (m, 1H), 1.91-2.00 (m, 1H), 1.75 (dd, 1H), 1.54-1.64 (m, 1H), 1.48-1.53 (m, 2H), 1.46 (s, 9H).

LCMS m/z=367.9 $[MNa]^+$ ($^{79}Br$ isotope)

Preparation 43

3-Bromo-1-(tetrahydro-2H-pyran-2-yl)-5-(diBoc)-amino-1H-pyrazole

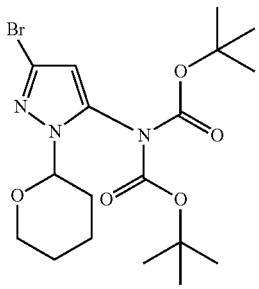 [SMILES: CC(C)(C)OC(=O)N(C(=O)OC(C)(C)C)c1cc(Br)nn1C1CCCCO1]

DMAP (27 mg, 0.22 mmol) was added to a solution of tert-butyl (3-bromo-1-(tetrahydro-2H-pyran-2-yl)-1H-pyrazol-5-yl)carbamate (Preparation 42, 390 mg, 1.13 mmol), di-tert-butyl dicarbonate (492 mg, 2.25 mmol) and TEA (0.47 mL, 3.38 mmol) in DCM (4 mL) at about 20° C. After about 18 hrs, the mixture was concentrated and the residue was purified by chromatography to afford the title compound (450 mg, 89%)

$^1$H NMR (400 MHz, CDCl$_3$) δ: 6.42 (s, 1H), 5.15 (m, 1H), 4.02 (m, 1H), 3.60 (m, 1H), 2.40 (m, 1H), 2.15 (m, 1H), 1.88 (m, 1H), 1.58-1.76 (m, 3H), 1.48 (s, 18H).

LCMS m/z=467.9 [MNa]$^+$ ($^{79}$Br isotope)

Preparation 44

2-((1r,3s)-1-(4-(6-(5-(DiBoc)-amino-1-(tetrahydro-2H-pyran-2-yl)-pyrazol-3-yl)pyrazolo[1,5-a]pyrazin-4-yl)-1H-pyrazol-1-yl)-3-methoxycyclobutyl)acetonitrile

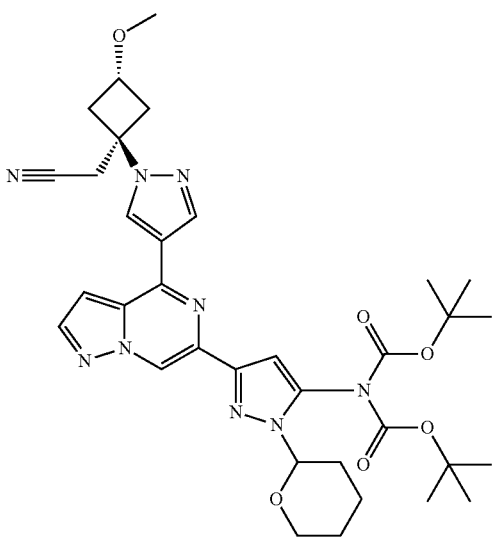 [SMILES: CO[C@H]1C[C@](CC#N)(n2cc(-c3nc(-c4cc(N(C(=O)OC(C)(C)C)C(=O)OC(C)(C)C)n(C5CCCCO5)n4)cn4nccc34)cn2)C1]

A mixture of KOAc (110 mg, 1.06 mmol), bis(pinacolato)diboron (164 mg, 0.64 mmol), 3-bromo-1-(tetrahydro-2H-pyran-2-yl)-5-(diBoc)-amino-1H-pyrazole (Preparation 43, 191 mg, 0.43 mmol) and XPhos Pd G2 (55 mg, 0.07 mmol) in 1,4-dioxane (3.5 mL) was heated to about 65° C. for about 3.5 hrs. The mixture was cooled to about 25° C. and 2-((1r,3s)-1-(4-(6-chloropyrazolo[1,5-a]pyrazin-4-yl)-1H-pyrazol-1-yl)-3-methoxy-cyclobutyl)acetonitrile (Preparation 39, 68 mg, 0.20 mmol) was added and the mixture was purged with nitrogen before 2 M aq. K$_3$PO$_4$ (0.53 mL, 1.06 mmol) and XPhos Pd G2 (55 mg, 0.07 mmol) were added. The mixture was heated at about 80° C. for about 3 hrs. The reaction was quenched with brine and extracted with EtOAc. The EtOAc extract was concentrated and the residue was purified by chromatography to afford the title compound as a yellow solid (91 mg, 32%).

$^1$H NMR (400 MHz, CDCl$_3$) δ: 9.08 (s, 1H), 8.39 (s, 1H), 8.33 (s, 1H), 8.09 (d, 1H), 6.97 (d, 1H), 6.90 (s, 1H), 5.26 (dd, 1H), 4.02-4.11 (m, 2H), 3.64 (t, 1H), 3.34 (s, 3H), 3.25 (s, 2H), 3.12-3.20 (m, 2H), 2.55-2.62 (m, 2H), 2.17-2.25 (m, 1H), 1.93 (dd, 1H), 1.58-1.82 (m, 4H), 1.45 (s, 18H).

LCMS m/z=674.5 [MH]$^+$

Preparation 45

2-((1r,3s)-1-(4-(6-(5-Amino-1H-pyrazol-3-yl)pyrazolo[1,5-a]pyrazin-4-yl)-1H-pyrazol-1-yl)-3-methoxycyclobutyl)acetonitrile

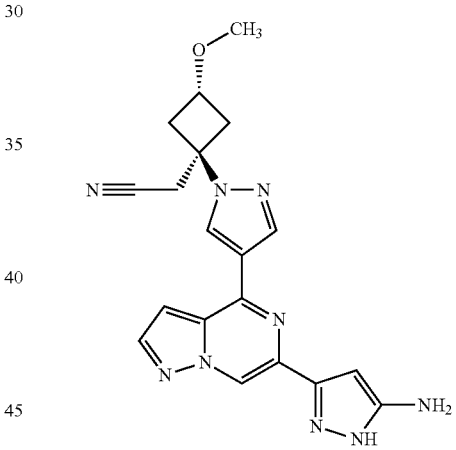

TFA (2 mL) was added to 2-((1r,3s)-1-(4-(6-(5-(diBoc)-amino-1-(tetrahydro-2H-pyran-2-yl)-pyrazol-3-yl)pyrazolo[1,5-a]pyrazin-4-yl)-1H-pyrazol-1-yl)-3-methoxycyclobutyl)-acetonitrile (Preparation 44, 91 mg, 0.13 mmol) in anhydrous DCM (1 mL) at about 20° C. After about 1 hr, the mixture was concentrated. DCM was added, followed by saturated aq. NaHCO$_3$ until the solution pH became basic. The phases were separated and the aqueous phase was extracted twice with DCM. The combined DCM extracts were dried (Na$_2$SO$_4$), concentrated, and the residue was purified by chromatography to afford the title compound (50 mg, 95%).

$^1$H NMR (400 MHz, CDCl$_3$) δ: 8.53 (s, 1H), 8.40 (s, 1H), 8.25 (s, 1H), 8.06 (s, 1H), 6.96 (br. s., 1H), 6.01 (br. s., 1H), 4.33 (br. s., 1H), 4.05 (m, 1H), 3.31 (s, 3H), 3.25 (s, 2H), 3.11 (dd, 2H), 2.55 (dd, 2H).

LCMS m/z=390.3 [MH]$^+$

Example 5

N-(3-(4-(1-(((1r,3s)-1-(Cyanomethyl)-3-methoxycyclobutyl)-1H-pyrazol-4-yl)pyrazolo[1,5-a]pyrazin-6-yl)-1H-pyrazol-5-yl)acetamide

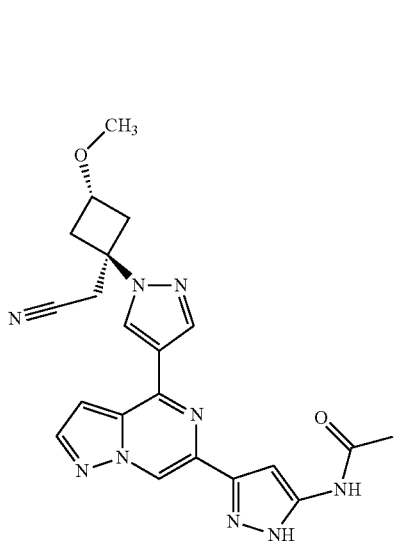 [SMILES: CO[C@H]1C[C@](CC#N)(n2cc(-c3nc(-c4cc(NC(C)=O)[nH]n4)cn4nccc34)cn2)C1]

2-((1r,3s)-1-(4-(6-(5-Amino-1H-pyrazol-3-yl)pyrazolo[1,5-a]pyrazin-4-yl)-1H-pyrazol-1-yl)-3-methoxy-cyclobutyl)acetonitrile (Preparation 45, 39 mg, 0.1 mmol) was placed in a reaction tube, which was then evacuated and backfilled three times with nitrogen. To this was added anhydrous DCM (1 mL). The tube was cooled to about 0° C. before N-methylmorpholine (11 mg, 0.11 mmol) and acetyl chloride (8.6 mg, 0.11 mmol) were added. The mixture was allowed to warm to about 25° C. over about 18 hrs. The mixture was concentrated and the residue was dissolved in MeOH (2 mL). $K_2CO_3$ (30 mg, 0.22 mmol) was added at about 0° C. After about 3 hrs, the mixture was filtered through Celite®. The filtrate was concentrated and the residue was purified by chromatography to afford the title compound (30 mg, 63%).

$^1$H NMR (400 MHz, CD$_3$OD) δ: 8.80 (s, 1H), 8.75 (s, 1H), 8.40 (s, 1H), 8.09 (d, 1H), 7.23 (d, 1H), 6.88 (s, 1H), 4.02-4.12 (m, 1H), 3.81 (s, 3H), 3.34 (s, 2H), 3.15-3.24 (m, 2H), 2.48-2.59 (m, 2H), 2.21 (s, 3H).

LCMS m/z=432.2 [MH]$^+$

Preparation 46

Ethyl 5-(4-(1-(((1r,3s)-1-(cyanomethyl)-3-methoxycyclobutyl)-1H-pyrazol-4-yl)pyrazolo[1,5-a]pyrazin-6-yl)-1H-pyrazole-3-carboxylate

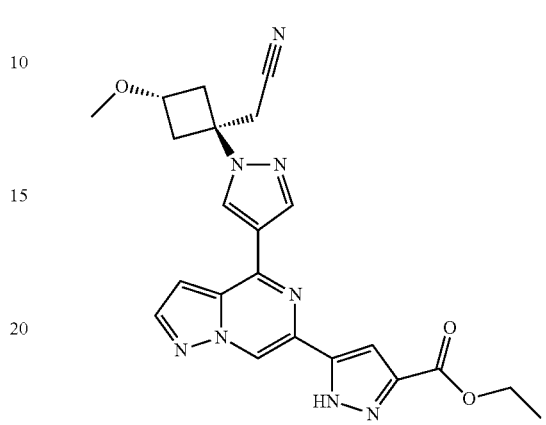

A solution of 2-((1r,3s)-1-(4-(6-chloropyrazolo[1,5-a]pyrazin-4-yl)-1H-pyrazol-1-yl)-3-methoxycyclobutyl)acetonitrile (Preparation 39, 200 mg, 0.58 mmol) and ethyl 3-(tributylstannyl)-1H-pyrazole-5-carboxylate (Preparation 31, 300 mg, 0.70 mmol) in 1,4-dioxane (5.8 mL) was purged with nitrogen and XPhos Pd G2 (45.9 mg, 0.058 mmol) added at about 25° C. The reaction was heated at about 80° C. for about 16 hrs. The cooled mixture was purified by chromatography to afford the title compound as a yellow solid (220 mg, 84%).

$^1$H NMR (400 MHz, DMSO-d$_6$) δ: 14.09 (s, 1H), 9.39 (s, 1H), 9.10 (s, 1H), 8.72 (s, 1H), 8.30 (d, 1H), 7.59 (d, 1H), 7.53 (d, 1H), 4.33 (q, 2H), 4.01 (dd, 1H), 3.44 (s, 3H), 3.22 (s, 2H), 3.14-3.20 (m, 2H), 2.43-2.48 (m, 2H), 1.34 (t, 3H).

LCMS m/z=447.2 [MH]$^+$

Example 6

5-(4-(1-(((1r,3s)-1-(Cyanomethyl)-3-methoxycyclobutyl)-1H-pyrazol-4-yl)pyrazolo[1,5-a]pyrazin-6-yl)-N-methyl-1H-pyrazole-3-carboxamide

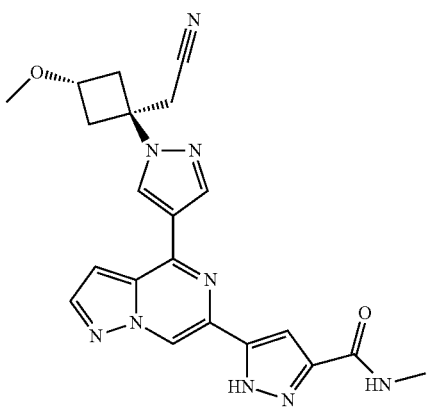

A solution of ethyl 5-(4-(1-((1r,3s)-1-(cyanomethyl)-3-methoxycyclobutyl)-1H-pyrazol-4-yl)pyrazolo[1,5-a]

pyrazin-6-yl)-1H-pyrazole-3-carboxylate (Preparation 46, 100 mg, 0.22 mmol) in 30% MeNH₂ in EtOH solution (35 mL) was sealed in a microwave tube at about 20° C. After about 16 hrs, the mixture was concentrated and the residue was purified by HPLC to afford the title compound as a white solid (62 mg, 58%).

¹H NMR (400 MHz, CD₃OD) δ: 9.00 (s, 1H), 8.91 (s, 1H), 8.57 (s, 1H), 8.18 (s, 1H), 7.37 (br. s., 1H), 7.26 (s, 1H), 4.61 (s, 1H), 4.04-4.15 (m, 1H), 3.37 (s, 3H), 3.33 (s, 2H), 3.18-3.26 (m, 2H), 2.95 (s, 3H), 2.56 (dd, 2H).

LCMS m/z=432.1 [M+H]⁺

Preparation 47 tert-Butyl 3-(cyanomethyl)-3-(4-(6-(1-methyl-1H-pyrazol-4-yl)pyrazolo[1,5-a]pyrazin-4-yl)-1H-pyrazol-1-yl)azetidine-1-carboxylate

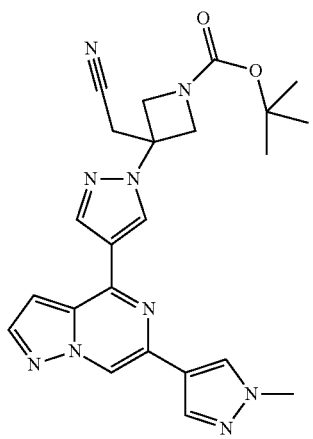 [SMILES: Cn1cc(-c2cn3nccc3c(-c3cnn(C4(CC#N)CN(C(=O)OC(C)(C)C)C4)c3)n2)cn1]

To a vial were added 4-chloro-6-(1-methyl-1H-pyrazol-4-yl)pyrazolo[1,5-a]pyrazine (Preparation 11, 150 mg), tert-butyl 3-(cyanomethyl)-3-(4-(4,4,5,5-tetramethyl-1,3,2-dioxaborolan-2-yl)-1H-pyrazol-1-yl)azetidine-1-carboxylate (Preparation 28, 374 mg, 0.96 mmol), 2 M aq. Na₂CO₃ (0.96 mL) and 1,4-dioxane (4 mL). The mixture was purged with argon for about 5 min, followed by the addition of PdCl₂(dppf) (93.7 mg, 0.13 mmol). The mixture was heated at about 120° C. for about 1 hr under microwave irradiation. The mixture was diluted with EtOAc, washed with water, dried (Na₂SO₄), and concentrated. The residue was purified by chromatography to afford the title compound as a yellow solid (233 mg, 79%).

¹H NMR (400 MHz, DMSO-d₆) δ: 9.03 (s, 1H), 8.95 (s, 1H), 8.53 (s, 1H), 8.37 (s, 1H), 8.20 (d, 1H), 8.16 (s, 1H), 7.46 (s, 1H), 4.54 (d, 2H), 4.25 (d, 3H), 3.91 (s, 3H), 3.67 (s, 2H), 1.42 (s, 9H).

LCMS m/z=460.2 [MH]⁺

Preparation 48

2-(3-(4-(6-(1-Methyl-1H-pyrazol-4-yl)pyrazolo[1,5-a]pyrazin-4-yl)-1H-pyrazol-1-yl)azetidin-3-yl)acetonitrile

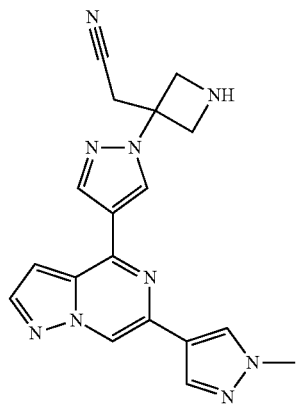 [SMILES: Cn1cc(-c2cn3nccc3c(-c3cnn(C4(CC#N)CNC4)c3)n2)cn1]

TFA (1 mL) was added to tert-butyl 3-(cyanomethyl)-3-(4-(6-(1-methyl-1H-pyrazol-4-yl)pyrazolo[1,5-a]pyrazin-4-yl)-1H-pyrazol-1-yl)azetidine-1-carboxylate (Preparation 47, 233 mg, 0.51 mmol) in DCM (5 mL) at about 25° C. After about 90 min, the mixture was concentrated. The residue was concentrated twice with toluene, then dried under vacuum. The residue was dissolved in MeOH and passed through a bed of polymer supported carbonate resin. The eluted solution was concentrated to afford the title compound (200 mg, about 100%) which was used without further purification.

¹H NMR (400 MHz, DMSO-d₆) δ: 9.12 (s, 1H), 9.06 (s, 1H), 8.58 (s, 1H), 8.39 (s, 1H), 8.22 (d, 1H), 8.17 (s, 1H), 7.50 (d, 1H), 4.68-4.77 (m, 2H), 4.35-4.40 (m, 2H), 3.93 (s, 2H), 3.91 (s, 3H).

LCMS m/z=360.5 [MH]⁺

Example 7

2,2'-(3-(4-(6-(1-Methyl-1H-pyrazol-4-yl)pyrazolo[1,5-a]pyrazin-4-yl)-1H-pyrazol-1-yl)azetidine-1,3-diyl)diacetonitrile

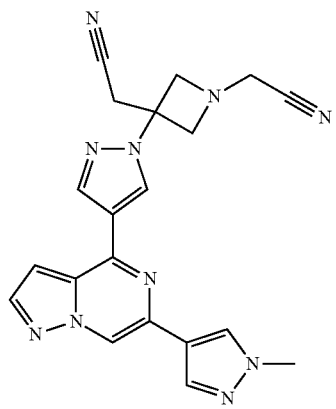 [SMILES: Cn1cc(-c2cn3nccc3c(-c3cnn(C4(CC#N)CN(CC#N)C4)c3)n2)cn1]

DIPEA (132 μl, 0.76 mmol) was added to a solution of 2-(3-(4-(6-(1-methyl-1H-pyrazol-4-yl)pyrazolo[1,5-a]pyrazin-4-yl)-1H-pyrazol-1-yl)azetidin-3-yl)acetonitrile (Preparation 48, 91 mg, 0.25 mmol) in DMF (2 mL). Bromoacetonitrile (36 mg, 0.30 mmol) was added at about 25° C. After about 18 hrs, the reaction was quenched with conc. NH₄OH and stirred at about 25° C. for about 10 min. The mixture was concentrated and the residue was diluted with DCM. The DCM was washed twice with saturated aq. NH₄Cl, then twice with saturated aq. Na₂CO₃. The DCM was dried (Na₂SO₄) and concentrated. The residue was .purified by chromatography to afford the title compound as an off white solid (68 mg, 68%).

¹H NMR (400 MHz, CD₃OD) δ: 8.77 (s, 1H), 8.74 (s, 1H), 8.45 (s, 1H), 8.25 (s, 1H), 8.08-8.10 (m, 2H), 7.25 (d, 1H), 4.01 (d, 2H), 3.98 (s, 3H), 3.86 (d, 2H), 3.78 (s, 2H), 3.54 (s, 2H)

LCMS m/z=399.3 [MH]⁺

Example 8

2-(3-(4-(6-(1-Methyl-1H-pyrazol-4-yl)pyrazolo[1,5-a]pyrazin-4-yl)-1H-pyrazol-1-yl)-1-(methylsulfonyl)azetidin-3-yl)acetonitrile

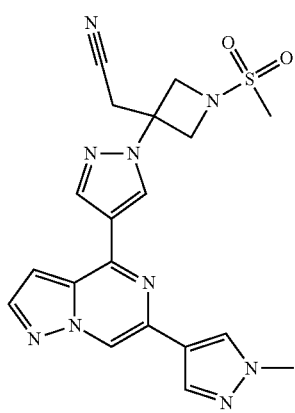 [SMILES: Cn1cc(-c2cn3nccc3c(-c3cnn(C4(CC#N)CN(S(C)(=O)=O)C4)c3)n2)cn1]

To a solution of 2-(3-(4-(6-(1-methyl-1H-pyrazol-4-yl)pyrazolo[1,5-a]pyrazin-4-yl)-1H-pyrazol-1-yl)azetidin-3-yl)acetonitrile (Preparation 48, 120 mg, 0.27 mmol) and TEA (331 mg, 3.27 mmol) in DCM (20 mL) was added methanesulfonyl chloride (313 mg, 2.73 mmol) at about 0° C. The mixture was then stirred at about 10° C. for about 1 hr before being concentrated. The residue was purified using HPLC to afford the title compound as a white solid (39 mg, 33%).

¹H NMR (400 MHz, DMSO-d₆) δ: 9.05 (s, 1H), 8.99 (s, 1H), 8.57 (s, 1H), 8.37 (s, 1H), 8.21 (d, 1H), 8.17 (s, 1H), 7.47 (d, 1H), 4.65 (d, 2H), 4.30 (d, 2H), 3.91 (s, 3H), 3.70 (s, 2H), 3.14 (s, 3H).

LCMS m/z=437.9 [MH]⁺

Example 9

2-(1-(Cyclopropylsulfonyl)-3-(4-(6-(1-methyl-1H-pyrazol-4-yl)pyrazolo[1,5-a]pyrazin-4-yl)-1H-pyrazol-1-yl)azetidin-3-yl)acetonitrile

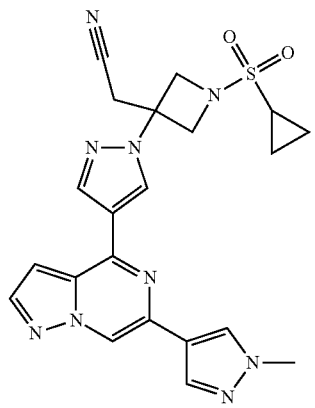 [SMILES: Cn1cc(-c2cn3nccc3c(-c3cnn(C4(CC#N)CN(S(=O)(=O)C5CC5)C4)c3)n2)cn1]

To a mixture of 2-(3-(4-(6-(1-methyl-1H-pyrazol-4-yl)pyrazolo[1,5-a]pyrazin-4-yl)-1H-pyrazol-1-yl)azetidin-3-yl)acetonitrile (Preparation 48, 100 mg, 0.25 mmol) in DCM (10 mL) were added TEA (153 mg, 1.52 mmol) and cyclopropanesulfonyl chloride (107 mg, 0.76 mmol) at about 0° C. The mixture was stirred at about 20° C. for about 16 hrs, then concentrated. The residue was purified by HPLC to afford the title compound as a white solid (60 mg, 46%).

¹H NMR (400 MHz, DMSO-d₆) δ: 9.05 (s, 1H), 9.00 (s, 1H), 8.57 (s, 1H), 8.37 (s, 1H), 8.21 (d, 1H), 8.16 (s, 1H), 7.46 (d, 1H), 4.69 (d, 2H), 4.32 (d, 2H), 3.91 (s, 3H), 3.70 (s, 2H), 2.85 (m, 1H), 0.96-1.09 (m, 4H).

LCMS m/z=464.0 [MH]⁺

Example 10

2-(3-(4-(6-(1-Methyl-1H-pyrazol-4-yl)pyrazolo[1,5-a]pyrazin-4-yl)-1H-pyrazol-1-yl)-1-propionylazetidin-3-yl)acetonitrile

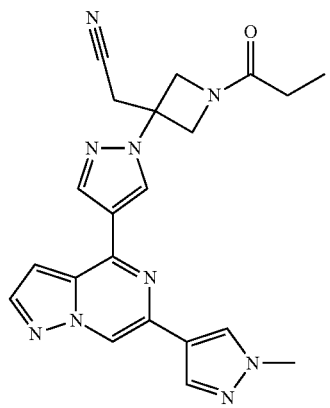 [SMILES: CCC(=O)N1CC(CC#N)(n2cc(-c3nc(-c4cnn(C)c4)cn4nccc34)cn2)C1]

To a solution of 2-(3-(4-(6-(1-methyl-1H-pyrazol-4-yl)pyrazolo[1,5-a]pyrazin-4-yl)-1H-pyrazol-1-yl)azetidin-3-yl)acetonitrile (Preparation 48, 90 mg, 0.23 mmol) in DCM (5 mL) were added TEA (69 mg, 0.68 mmol) and propionic anhydride (59 mg, 0.45 mmol). The reaction was stirred at about 20° C. for about 30 min, then concentrated and the residue was purified by HPLC to afford the title compound as a white solid (28 mg, 30%).

$^1$H NMR (400 MHz, DMSO-$d_6$) δ: 9.05 (s, 1H), 8.97 (s, 1H), 8.55 (s, 1H), 8.37 (s, 1H), 8.21 (d, 1H), 8.16 (s, 1H), 7.46 (d, 1H), 4.80 (d, 1H), 4.52 (dd, 2H), 4.23 (d, 1H), 3.91 (s, 3H), 3.70 (s, 2H), 2.16 (q, 2H), 0.99 (t, 3H).

LCMS m/z 416.0 [MH]$^+$

Preparation 49

2-(3-(Benzyloxy)cyclobutylidene)acetonitrile

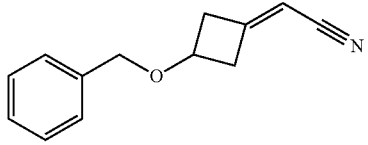 [SMILES: N#CC=C1CC(OCc2ccccc2)C1]

LiBr (0.270 g, 3.12 mmol) was placed under vacuum, then backfilled with nitrogen and THF (28 mL) was added, followed by (EtO)$_2$POCH$_2$CN (0.53 mL, 3.12 mmol) and TEA (0.79 mL, 5.67 mmol). The resulting solution was stirred at about 20° C. for about 45 min, then a solution of 3-(benzyloxy)cyclobutanone (500 mg, 2.84 mmol) in dry THF (3 mL) was added. After about 5 hrs, the mixture was poured into EtOAc (100 mL) and the EtOAc was washed three times with saturated aq. NH$_4$Cl (3×50 mL) and with brine (25 mL). The EtOAc extract was dried (MgSO$_4$) and concentrated. The residue was chromatographed to afford the title compound (480 mg, 85%).

$^1$H NMR (400 MHz, CDCl$_3$) δ: 7.29-7.43 (m, 5H), 5.24 (quin, 1H), 4.45-4.53 (m, 2H), 4.19 (quin, 1H), 3.18-3.29 (m, 1H), 3.03-3.13 (m, 1H), 2.86-3.00 (m, 2H).

Preparation 50

2-(3-Hydroxycyclobutyl)acetonitrile

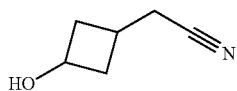

Palladium hydroxide on carbon (20% Pd, wet, 430 mg) was added to a solution of 2-(3-(benzyloxy)cyclobutylidene)acetonitrile (Preparation 49, 430 mg, 2.16 mmol) in THF (6.5 mL). The mixture was pressurized under hydrogen (100 psi) in a steel reactor and stirred at about 20° C. for about 1 hr. Additional palladium hydroxide on carbon (20% Pd, wet, 430 mg) added and the mixture was re-pressurized under hydrogen (100 psi) and stirred for about 1.5 hrs longer. The mixture was diluted with EtOAc, filtered through Celite®, and the filtrate was concentrated to afford the title compound as a colorless oil (240 mg, 100%) as a mixture of cis and trans isomers.

Isomer 1-(400 MHz, CDCl$_3$) δ: 4.52 (quin, 1H), 2.63-2.74 (m, 2H), 2.19-2.28 (m, 4H), 2.07-2.17 (m, 1H), 1.83 (br. s, 1H).

Isomer 2: $^1$H NMR (400 MHz, CDCl$_3$) δ: 4.14-4.25 (m, 1H), 2.55-2.64 (m, 2H), 2.48 (dd, 4H), 1.83 (br. s, 1H), 1.67-1.79 (m, 1H).

Preparation 51

2-(3-Oxocyclobutyl)acetonitrile

To a solution of 2-(3-hydroxycyclobutyl)acetonitrile (Preparation 50, 50 mg, 0.45 mmol) in dry THF (1.8 mL) was added Dess-Martin periodinane (CAS: 87413-09-0, 216 mg, 0.49 mmol). The vial was sealed under ambient atmosphere and stirred at about 50° C. for about 2 hrs. The mixture was diluted with Et$_2$O (10 mL) followed by saturated aq. NaHCO$_3$ (4 mL). Sodium thiosulfate pentahydrate (954 mg, 3.82 mmol) was added and the mixture was stirred vigorously for about 10 min until all solids had dissolved. The phases were separated and the aqueous phase extracted once more with Et$_2$O. The combined Et$_2$O extracts were dried (MgSO$_4$) and concentrated. The residue was purified by chromatography to afford the title compound as a colorless oil (27 mg, 55%).

$^1$H NMR (400 MHz, CDCl$_3$) δ: 3.23-3.37 (m, 2H), 2.89-3.01 (m, 2H), 2.75-2.89 (m, 1H), 2.69 (d, 2H).

$^{13}$C NMR (101 MHz, CDCl$_3$) δ: 203.6, 117.6, 52.3, 23.1, 20.6.

Preparation 52

2-(3-(Cyanomethyl)cyclobutylidene)acetonitrile

The title compound was prepared (75 mg, 89%) using the method of Preparation 35 using 2-(3-oxocyclobutyl)acetonitrile (Preparation 51, 70 mg, 0.64 mmol), (EtO)$_2$POCH$_2$CN (213 mg, 1.15 mmol), LiBr (100 mg, 1.15 mmol) and TEA (0.27 mL, 1.92 mmol). The title compound was used directly in the next reaction (Example 11 and 12).

$^1$H NMR (400 MHz, CDCl$_3$) δ: 5.25 (m, 1H), 3.10-3.30 (m, 2H), 2.80 (m, 3H), 2.60 (m, 2H).

GCMS m/z=132 [M]$^+$

Preparation 53

6-(1-Methyl-1H-pyrazol-4-yl)-4-(1H-pyrazol-4-yl)pyrazolo[1,5-a]pyrazine

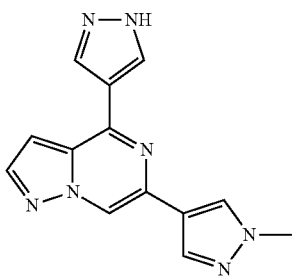 [SMILES: Cn1cc(-c2cn3nccc3c(-c3cn[nH]c3)n2)cn1]

Pd(dppf)Cl$_2$ (5.01 g, 6.85 mmol) was added a mixture of 4-chloro-6-(1-methyl-1H-pyrazol-4-yl)pyrazolo[1,5-a]pyrazine (Preparation 11, 8 g, 34 mmol), tert-butyl 4-(4,4,5,5-tetramethyl-1,3,2-dioxaborolan-2-yl)-1H-pyrazole-1-carboxylate (12.1 g, 41.1 mmol) and 2 M aq. K$_2$CO$_3$ (34.2 mL) in 1,4-dioxane (30 mL) and toluene (30 mL) at about 10° C. while a stream of nitrogen was bubbled through the solution. The mixture was stirred at about 100° C. for about 16 hrs, then kept at about 10° C. for about 48 hrs. The mixture was filtered and the filtrate was concentrated. The residue was purified by chromatography to afford the title compound as a grey oil (6.3 g, 69%).

$^1$H NMR (400 MHz, DMSO-d$_6$) δ: 8.97 (s, 1H), 8.72 (s, 1H), 8.40 (s, 1H), 8.35 (s, 1H), 8.15 (d, 1H), 8.12 (s, 1H), 7.36 (d, 1H), 3.91 (s, 3H).

LCMS m/z=265.8 [MH]$^+$

Example 11

2,2'-((1s,3s)-1-(4-(6-(1-Methyl-1H-pyrazol-4-yl)pyrazolo[1,5-a]pyrazin-4-yl)-1H-pyrazol-1-yl)cyclobutane-1,3-diyl)diacetonitrile (cis isomer)

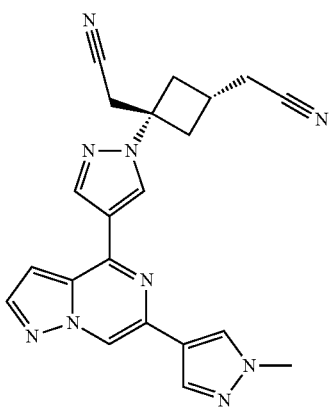 [SMILES: Cn1cc(-c2cn3nccc3c(-c3cnn([C@]4(CC#N)C[C@H](CC#N)C4)c3)n2)cn1]

and

Example 12

2,2'-((1r,3r)-1-(4-(6-(1-Methyl-1H-pyrazol-4-yl)pyrazolo[1,5-a]pyrazin-4-yl)-1H-pyrazol-1-yl)cyclobutane-1,3-diyl)diacetonitrile (trans isomer)

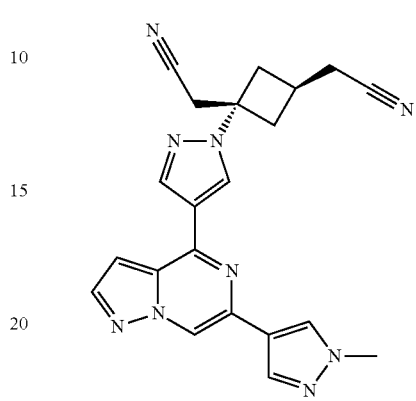

DBU (34 mg, 0.22 mmol) was added to a slurry of 2-(3-(cyanomethyl)cyclobutylidene)acetonitrile (Preparation 52, 32 mg, 0.24 mmol) and 6-(1-methyl-1H-pyrazol-4-yl)-4-(1H-pyrazol-4-yl)pyrazolo[1,5-a]pyrazine (Preparation 53, 53 mg, 0.20 mmol) in MeCN (4.8 mL). The mixture was heated at about 50° C. for about 16 hours, then concentrated. The residue was purified by chromatography to afford a mixture of the title compounds as 1:1 mixture of cis/trans isomers (80 mg, 83%). The isomers were separated by HPLC to afford 2,2'-((1s,3s)-1-(4-(6-(1-methyl-1H-pyrazol-4-yl)pyrazolo[1,5-a]pyrazin-4-yl)-1H-pyrazol-1-yl)cyclobutane-1,3-diyl)diacetonitrile as a solid (cis isomer, 27 mg, 36%).

$^1$H NMR (500 MHz, 9:1 CDCl$_3$-CD$_3$OD) δ: 8.45 (s, 1H), 8.35 (s, 1H), 8.25 (s, 1H), 7.99 (d, 1H), 7.95 (s, 1H), 7.92 (s, 1H), 6.93 (s, 1H), 3.95 (s, 3H), 3.72 (s, 2H), 3.18 (s, 2H), 2.81-2.91 (m, 2H), 2.72-2.81 (m, 1H), 2.72-2.81 (m, 1H), 2.64-2.72 (m, 2H), 2.61 (d, 2H).

LCMS m/z=399.1 [MH]

and 2,2'-((1r,3r)-1-(4-(6-(1-methyl-1H-pyrazol-4-yl)pyrazolo[1,5-a]pyrazin-4-yl)-1H-pyrazol-1-yl)cyclo-butane-1,3-diyl)diacetonitrile as a solid (trans isomer, 14 mg, 18%).

$^1$H NMR (500 MHz, CDCl$_3$) δ: 8.49 (s, 1H), 8.46 (s, 1H), 8.32 (s, 1H), 8.05 (d, 1H), 7.96 (m, 2H), 6.95 (d, 1H), 4.00 (s, 3H), 3.75 (br. s., 1H), 3.15-3.25 (m, 2H), 3.11 (s, 2H), 2.88 (tt, 1H), 2.64 (d, 2H), 2.48-2.59 (m, 2H).

LCMS m/z=399.1 [MH]

Preparation 54

2-(3-(Benzyloxy)cyclobutylidene)acetonitrile

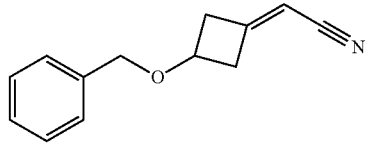 [SMILES: N#CC=C1CC(OCc2ccccc2)C1]

To a solution of (EtO)$_2$P(O)CH$_2$CN (24.1 g, 136 mmol) in dry THF (500 mL) was added LiBr (11.8 g, 136 mmol) and TEA (18.4 g, 182 mmol) and the resulting mixture was stirred at about 20° C. for about 1 hr. To this was added 3-(benzyloxy)cyclobutan-1-one (16.00 g, 90.8 mmol). The mixture was stirred at about 20° C. for about 20 hrs. The mixture was filtered and the filtrate was concentrated. The residue was purified by chromatography to afford the title compound as a pale yellow liquid (18 g, 99%).

$^1$H NMR (400 MHz, CDCl$_3$) δ: 7.29-7.40 (m, 5H), 5.24 (dt, 1H), 4.45-4.53 (m, 2H), 4.19 (quin, 1H), 3.19-3.29 (m, 1H), 3.03-3.13 (m, 1H), 2.86-3.00 (m, 2H).

LCMS m/z=200.1 [MH]$^+$

Preparation 55

2-(3-(Benzyloxy)-1-(4-(6-(1-methyl-1H-pyrazol-4-yl)pyrazolo[1,5-a]pyrazin-4-yl)-1H-pyrazol-1-yl) cyclobutyl)acetonitrile (mixture of cis and trans isomers)

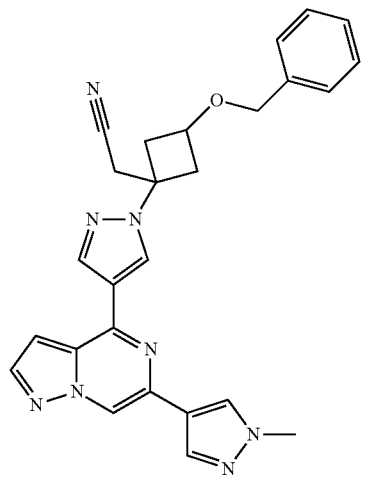 [SMILES: Cn1cc(-c2cn3nccc3c(-c3cnn(C4(CC#N)CC(OCc5ccccc5)C4)c3)n2)cn1]

DBU (1.448 g, 9.4 mmol) was added to a solution of 6-(1-methyl-1H-pyrazol-4-yl)-4-(1H-pyrazol-4-yl)pyrazolo [1,5-a]pyrazine (Preparation 53, 313 mg, 1.18 mmol) and 2-(3-(benzyloxy)cyclobutylidene)acetonitrile (Preparation 54, 470 mg, 2.36 mmol) in MeCN (6.38 mL). The mixture was stirred at about 20° C. for about 18 hrs, then it was poured into aq. NaH$_2$PO$_4$ solution to maintain a pH of about 5. The mixture was extracted three times with DCM. The combined DCM extracts were concentrated and the residue was purified by chromatography to afford the title compound (474 mg, 86%).

$^1$H NMR (400 MHz, CD$_3$OD) δ: 8.67-8.72 (m, 2H), 8.63 (s, 1H), 8.39 (s, 1H), 8.22 (s, 1H), 8.04-8.10 (m, 2H), 7.25-7.42 (m, 5H), 4.53 (s, 2H), 4.24-4.34 (m, 1H), 3.97 (s, 3H), 3.29 (s, 2H), 2.92-3.02 (m, 2H), 2.77-2.88 (m, 2H).

LCMS m/z=465.3 [MH]$^+$

Example 13

2-((1s,3r)-3-Hydroxy-1-(4-(6-(1-methyl-1H-pyrazol-4-yl)pyrazolo[1,5-a]pyrazin-4-yl)-1H-pyrazol-1-yl) cyclobutyl)acetonitrile (cis isomer)

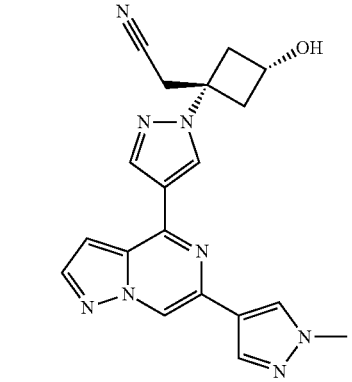 [SMILES: Cn1cc(-c2cn3nccc3c(-c3cnn([C@]4(CC#N)C[C@H](O)C4)c3)n2)cn1]

and

Example 14 PF-06877900

2-((1r,3s)-3-Hydroxy-1-(4-(6-(1-methyl-1H-pyrazol-4-yl)pyrazolo[1,5-a]pyrazin-4-yl)-1H-pyrazol-1-yl) cyclobutyl)acetonitrile (trans isomer)

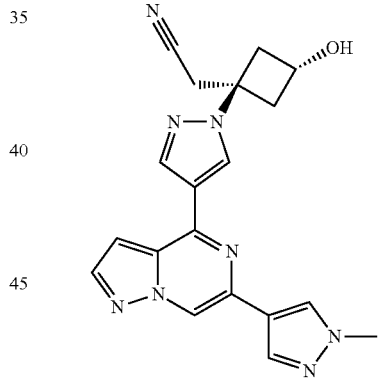

Sodium iodide was dried with a heating gun at full heat for 5 min then cooled to about 25° C. under nitrogen prior to use. The dried NaI (1.21 g, 8.1 mmol) was added at about 20° C. to a stirred solution of (2-(3-(benzyloxy)-1-(4-(6-(1-methyl-1H-pyrazol-4-yl)pyrazolo[1,5-a]pyrazin-4-yl)-1H-pyrazol-1-yl)cyclobutyl)acetonitrile (Preparation 55, 377 mg, 0.81 mmol) in MeCN (12 mL), followed by TMSCl (1.05 mL, 8.1 mmol). The mixture was stirred at about 50° C. for about 18 hrs. An additional portion of both NaI and TMSCl were added and the mixture was maintained at about 50° C. for about 8 hrs additional. The cooled mixture was poured into ice cold saturated aq. NaHCO$_3$ containing sodium thiosulfate pentahydrate (10.1 g, 40.6 mmol) and extracted three times with EtOAc. The combined EtOAc extracts were concentrated to afford a mixture of the two title compounds. This mixture was purified by chromatography to afford 2-((is, 3r)-3-hydroxy-1-(4-(6-(1-methyl-1H-pyrazol-4-yl)pyrazolo[1,5-a]pyrazin-4-yl)-1H-pyrazol-1-yl)cyclobutyl)acetonitrile (trans isomer, 80 mg, 26%)

$^1$H NMR (400 MHz, CD$_3$OD) δ: 8.72 (s, 1H), 8.71 (s, 1H), 8.42 (s, 1H), 8.24 (s, 1H), 8.05-8.10 (m, 2H), 7.24 (d, 1H), 4.34-4.44 (m, 1H), 3.98 (s, 3H), 3.35 (s, 2H), 3.22-3.28 (m, 2H), 2.49 (dd, 2H).

LCMS m/z=375.4 [MH]$^+$ and 2-((1r,3s)-3-hydroxy-1-(4-(6-(1-methyl-1H-pyrazol-4-yl)pyrazolo[1,5-a]pyrazin-4-yl)-1H-pyrazol-1-yl)cyclobutyl)acetonitrile (cis isomer, 180 mg, 59%).

$^1$H NMR (400 MHz, CD$_3$OD) δ: 8.67 (s, 1H), 8.62 (s, 1H), 8.38 (s, 1H), 8.21 (s, 1H), 8.07 (d, 1H), 8.05 (s, 1H), 8.04-8.06 (m, 1H), 7.21 (d, 1H), 4.41 (quin, 1H), 3.97 (s, 3H), 3.28 (s, 2H), 2.95-3.04 (m, 2H), 2.68-2.78 (m, 2H).

LCMS m/z=375.4 [MH]$^+$

Example 15

2-((1r,3s)-3-Methoxy-1-(4-(6-(1-methyl-1H-pyrazol-4-yl)pyrazolo[1,5-a]pyrazin-4-yl)-1H-pyrazol-1-yl)cyclobutyl)acetonitrile (trans isomer)

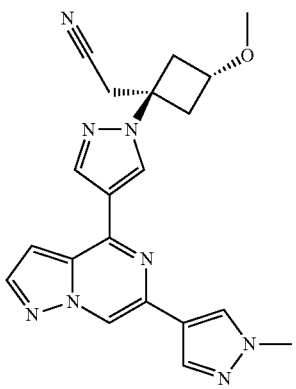 [SMILES: CO[C@H]1C[C@](CC#N)(n2cc(-c3nc(-c4cnn(C)c4)cn4nccc34)cn2)C1]

and

Example 16

2-((1s,3r)-3-Methoxy-1-(4-(6-(1-methyl-1H-pyrazol-4-yl)pyrazolo[1,5-a]pyrazin-4-yl)-1H-pyrazol-1-yl)cyclobutyl)acetonitrile (cis isomer)

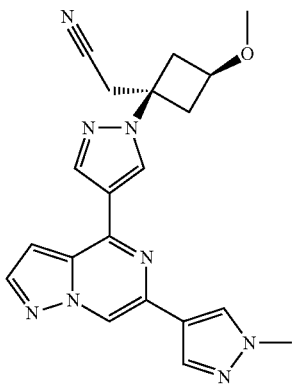 [SMILES: CO[C@H]1C[C@@](CC#N)(n2cc(-c3nc(-c4cnn(C)c4)cn4nccc34)cn2)C1]

A solution of a mixture of 24(1s,3r)-3-hydroxy-1-(4-(6-(1-methyl-1H-pyrazol-4-yl)pyrazolo[1,5-a]pyrazin-4-yl)-1H-pyrazol-1-yl)cyclobutyl)acetonitrile and 2-((1r,3s)-3-Hydroxy-1-(4-(6-(1-methyl-1H-pyrazol-4-yl)pyrazolo[1,5-a]pyrazin-4-yl)-1H-pyrazol-1-yl)cyclobutyl)acetonitrile (Examples 13 and 14, mixture of cis and trans isomers, 48 mg, 0.13 mmol) in THF (0.2 mL) was sequentially treated with tetrabutylammonium bromide (TBAB, 126 mg, 0.38 mmol), 1 M aq. NaOH (1.02 mL) and dimethyl sulfate (6 µL). The reaction vial was sealed and stirred vigorously at about 20° C. for about 1 hr. Additional dimethyl sulfate (14 µL) and TBAB (10 mg) were added and the reaction was kept at about 20° C. for about 2 hrs. The mixture was extracted three times with EtOAc and the combined EtOAc extracts were dried (Na$_2$SO$_4$) and concentrated. The residue was purified by chromatography to afford a mixture of cis and trans isomers. Further purification by HPLC afforded 24(1r,3s)-3-methoxy-1-(4-(6-(1-methyl-1H-pyrazol-4-yl)pyrazolo[1,5-a]pyrazin-4-yl)-1H-pyrazol-1-yl)cyclobutyl)acetonitrile as a solid (trans isomer, 10 mg, 20%)

$^1$H NMR (400 MHz, CD$_3$CN) δ: 8.61 (d, 1H), 8.55 (s, 1H), 8.38 (s, 1H), 8.12 (s, 1H), 8.05 (d, 1H), 7.99 (s, 1H), 7.13 (d, 1H), 3.99-4.08 (m, 1H), 3.93 (s, 3H), 3.27 (s, 5H), 3.13-3.21 (m, 2H), 2.45-2.53 (m, 2H).

LCMS m/z=389.1 [MH]$^+$ and 2-((1s, 3r)-3-methoxy-1-(4-(6-(1-methyl-1H-pyrazol-4-yl)pyrazolo[1,5-a]pyrazin-4-yl)-1H-pyrazol-1-yl)cyclobutyl)acetonitrile as a solid (cis isomer, 17 mg, 33%).

$^1$H NMR (400 MHz, CD$_3$CN) δ: 8.60 (d, 1H), 8.49 (s, 1H), 8.36 (s, 1H), 8.12 (s, 1H), 8.04 (d, 1H), 7.98 (s, 1H), 7.12 (dd, 1H), 4.03 (quin, 1H), 3.92 (s, 3H), 3.26 (s, 3H), 3.19 (s, 2H), 2.89-2.97 (m, 2H), 2.65-2.74 (m, 2H).

LCMS m/z=389.1 [MH]$^+$

Preparation 56

Benzyl (R)-2-methyl-3-oxoazetidine-1-carboxylate

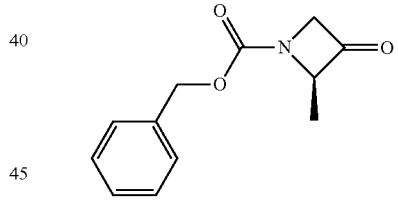

Part 1

A solution of N,4-dimethyl-N-nitrosobenzenesulfonamide (Diazald®, 21.25 g, 99.19 mmol) in Et$_2$O (150 mL) was added dropwise to a solution of KOH (6 g, 106.9 mmol) and 2-(2-ethoxyethoxy)ethanol (30 mL) and water (10 mL) at about 70° C. The mixture was heated at about 70° C. and an ethereal solution of diazomethane was collected as a yellow liquid by distillation (100 mL, estimated to contain 66 mmol of diazomethane) using a dry-ice/acetone condenser and used immediately in Part 2.

Part 2

Ethyl chloroformate (2.430 g, 22.4 mmol) was added dropwise to a solution of Cbz-D-alanine (5.00 g, 22.4 mmol) and TEA (2.27 mg, 22.4 mmol) in THF (50 mL) at about −15° C. The reaction mixture was warmed to about 0° C. and the diazomethane solution from Part 1 (100 mL, about 66 mmol) was added dropwise and stirred at about 20° C. for about 16 hrs. The reaction mixture was quenched with water (10 mL) and extracted with EtOAc (2×30 mL). The combined EtOAc extracts were dried (Na$_2$SO$_4$) and concentrated. The residue was purified by chromatography to afford the diazo-ketone intermediate (4.5 g, 81%) as a white solid. The material was used in Part 3.

Part 3

To a solution of the diazo-ketone intermediate of Part 2 (4.50 g, 18.2 mmol) in DCM (450 mL) were added TEA (18 mg, 0.18 mmol) and Rh$_2$(OAc)$_4$ (40 mg, 0.091 mmol) at about 0° C. The mixture was stirred for about 16 hrs at about 25° C. The mixture was quenched with water (50 mL) and the DCM phase was separated and concentrated. The residue was purified by chromatography on afford the title compound as a white solid (1.20 g, 30%).

$^1$H NMR (400 MHz, CDCl$_3$) δ: 7.34-7.38 (m, 5H), 5.18 (m, 2H), 5.03 (m, 1H), 4.65-4.81 (m, 2H), 1.49 (d, 3H).

GCMS m/z=219 [M]$^+$

Preparation 57

Benzyl (R)-3-(cyanomethylene)-2-methylazetidine-1-carboxylate

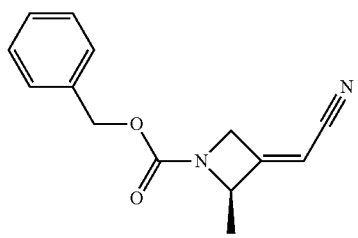 [SMILES: C[C@@H]1/C(=C/C#N)CN1C(=O)OCc1ccccc1]

To a mixture of LiBr (166 mg, 1.92 mmol) and TEA (277 mg, 2.74 mmol) in THF (10 mL) was added (EtO)$_2$P(O)CH$_2$CN (339 mg, 1.92 mmol) at about 25° C. After about 2.5 hrs, benzyl (R)-2-methyl-3-oxoazetidine-1-carboxylate (Preparation 56, 300 mg, 1.37 mmol) in THF (2 mL) was added at about 25° C. and the mixture was stirred for about 16 hrs. The mixture was concentrated and the residue was purified by chromatography to afford the title compound as mixture of E/Z olefin isomers as colorless oil (290 mg, 87%).

$^1$H NMR (400 MHz, CDCl$_3$) δ: 7.33-7.40 (m, 5H), 5.36 (m, 1H), 5.10-5.17 (m, 2H), 4.97 (m, 1H), 4.63-4.77 (m, 2H), 1.50-1.67 (m, 3H).

Preparation 58

Benzyl (2R)-3-(cyanomethyl)-2-methyl-3-(4-(6-(1-methyl-1H-pyrazol-4-yl)pyrazolo[1,5-a]pyrazin-4-yl)-1H-pyrazol-1-yl)azetidine-1-carboxylate

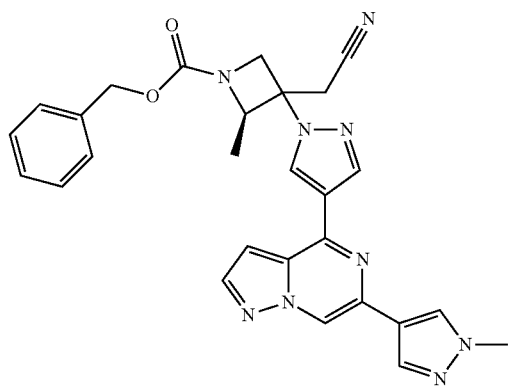 [SMILES: C[C@H]1N(C(=O)OCc2ccccc2)CC1(CC#N)n1cc(-c2nc(-c3cnn(C)c3)cn3nccc23)cn1]

To a solution of 6-(1-methyl-1H-pyrazol-4-yl)-4-(1H-pyrazol-4-yl)pyrazolo[1,5-a]pyrazine (Preparation 53, 268 mg, 1.01 mmol) in MeCN (15 mL) were added benzyl (R)-3-(cyanomethylene)-2-methylazetidine-1-carboxylate (Preparation 57, 294 mg, 1.21 mmol) and DBU (77 mg, 0.51 mmol) at about 15° C. The mixture was stirred at about 25° C. for about 7 hrs before being diluted with EtOAc (50 mL) and washed with 1 M aq. citric acid (15 mL) followed by brine (15 mL). The EtOAc extract was concentrated and the residue was purified by chromatography to afford the title compound as a yellow gum (500 mg, 97%).

$^1$H NMR (400 MHz, CDCl$_3$) δ: 8.49 (s, 1H), 8.33 (s, 1H), 8.32 (s, 1H), 8.05 (d, 1H), 7.96 (s, 1H), 7.95 (s, 1H), 7.33-7.40 (m, 5H), 6.93 (d, 2H), 5.15 (s, 2H), 4.87 (m, 1H), 4.61 (d, 1H), 4.26 (d, 1H), 4.01 (s, 3H), 3.27 (s, 2H), 1.69 (d, 3H).

LCMS m/z=530.1 [M+Na]$^+$

Preparation 59

2-((2R)-2-Methyl-3-(4-(6-(1-methyl-1H-pyrazol-4-yl)pyrazolo[1,5-a]pyrazin-4-yl)-1H-pyrazol-1-yl)azetidin-3-yl)acetonitrile

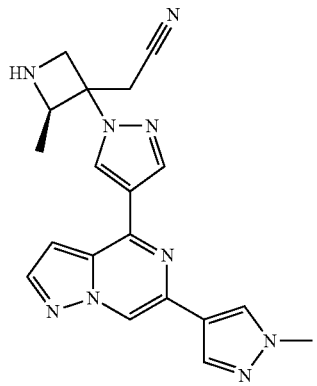 [SMILES: C[C@H]1NCC1(CC#N)n1cc(-c2nc(-c3cnn(C)c3)cn3nccc23)cn1]

To a mixture of NaI (2.36 g, 15.8 mmol) in MeCN (16 mL) was added TMSCl (2 mL, 15.8 mmol) at about 0° C.

The mixture was stirred at about 15° C. for about 4 hrs. A solution of benzyl (2R)-3-(cyanomethyl)-2-methyl-3-(4-(6-(1-methyl-1H-pyrazol-4-yl)pyrazolo[1,5-a]pyrazin-4-yl)-1H-pyrazol-1-yl)azetidine-1-carboxylate (Preparation 58, 400 mg, 0.79 mmol) in MeCN (4 mL) was added at about 0° C. Stirring was continued at about 15° C. for about 3 hrs. The mixture was cooled to about 10° C. and quenched by the addition of TEA (2 mL). The mixture was concentrated. The residue was dissolved in EtOAc (20 mL) and MeOH (2 mL) and the solids present were removed by filtration. The filtrate was concentrated and the residue was purified by TLC to afford the title compound as a yellow solid (200 mg, 68%).

$^1$H NMR (400 MHz, DMSO-$d_6$) δ: 9.06 (s, 1H), 9.03 (s, 1H), 8.59 (s, 1H), 8.39 (s, 1H), 8.22 (d, 1H), 8.16 (s, 1H), 7.47 (s, 1H), 5.09 (m, 1H), 4.74 (d, 1H), 4.24 (d, 1H), 3.91 (s, 3H), 2.99 (s, 2H), 1.65 (d, 3H).

LCMS m/z=374.0 [MH]$^+$

Example 17

2-((2R,3S)-2-Methyl-3-(4-(6-(1-methyl-1H-pyrazol-4-yl)pyrazolo[1,5-a]pyrazin-4-yl)-1H-pyrazol-1-yl)-1-(2,2,2-trifluoroethyl)azetidin-3-yl)acetonitrile

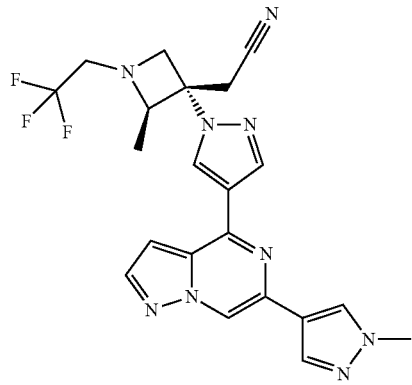 [SMILES: C[C@H]1N(CC(F)(F)F)C[C@]1(CC#N)n1cc(-c2nc(-c3cnn(C)c3)cn3nccc23)cn1]

To a solution of 2-((2R)-2-methyl-3-(4-(6-(1-methyl-1H-pyrazol-4-yl)pyrazolo[1,5-a]pyrazin-4-yl)-1H-pyrazol-1-yl) azetidin-3-yl)acetonitrile (Preparation 59, 200 mg, 0.43 mmol) in DMF (5 mL) were added 2,2,2-trifluoroethyl trifluoromethanesulfonate (298 mg, 1.29 mmol) and DIPEA (332 mg, 2.57 mmol). The mixture was stirred at about 10° C. for about 36 hrs before being diluted with EtOAc (30 mL) and washed with brine (15 mL). The EtOAc extract was concentrated the residue was purified by HPLC to afford the title compound as a mixture of diastereomers (80 mg, 41%) as a white solid. Further HPLC purification afforded the title compound as a white solid (41.8 mg, 21%, 94.7% ee).

$^1$H NMR (400 MHz, CD$_3$CN) δ: 8.59 (s, 1H), 8.45 (s, 1H), 8.36 (s, 1H), 8.10 (s, 1H), 8.04 (d, 1H), 7.98 (s, 1H), 7.09-7.13 (m, 1H), 3.92-3.96 (m, 1H), 3.91 (s, 3H), 3.84-3.89 (m, 1H), 3.77-3.84 (m, 1H), 3.38 (s, 2H), 3.28-3.43 (m, 1H), 3.15 (dq, 1H), 1.36 (d, 3H).

LCMS m/z=456.2 [MH]$^+$

Example 18

2-((1r,3r)-1-(4-(6-(1-Methyl-1H-pyrazol-4-yl)pyrazolo[1,5-a]pyrazin-4-yl)-1H-pyrazol-1-yl)-3-(1H-pyrazol-5-yl)cyclobutyl)acetonitrile

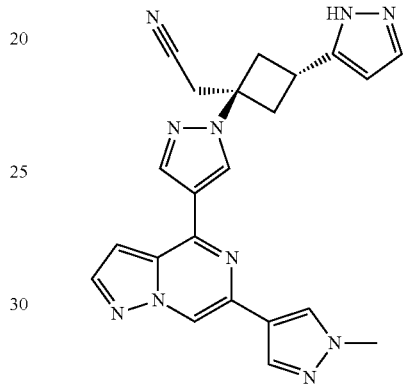

To a solution of LiBr (70 mg, 0.81 mmol), TEA (205 μL, 1.47 mmol) in THF (10 mL), was added (EtO)$_2$P(O)CH$_2$CN (143 mg, 0.81 mmol). The mixture was stirred at about 20° C. for about 30 min. 3-(1H-Pyrazol-5-yl)cyclobutan-1-one (Preparation 99, 100 mg, 0.74 mmol) was added and mixture was kept at about 20° C. for about 18 hrs. About 30% of the reaction solution was taken out and 6-(1-methyl-1H-pyrazol-4-yl)-4-(1H-pyrazol-4-yl)pyrazolo[1,5-a]pyrazine (Preparation 53, 58 mg, 0.22 mmol) and DBU (110 μL, 0.73 mmol) in MeCN (5 mL) were added. Stirring at about 20° C. was maintained for about 20 hrs. The mixture was concentrated and the residue was purified by chromatography to afford the title compound (6 mg, 6%).

$^1$H NMR (500 MHz, CD$_3$OD) δ: 8.85 (s, 1H), 8.73 (s, 1H), 8.46 (s, 1H), 8.26 (s, 1H), 8.10 (s, 2H), 7.60 (br. s., 1H), 7.28 (d, 1H), 6.32 (d, 1H), 3.95-4.04 (m, 3H), 3.69-3.78 (m, 1H), 3.33-3.43 (m, 2H), 2.77-2.89 (m, 2H).

LCMS m/z=425.4 [MH]$^+$

Example 19

(1s,3s)-3-(Cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile

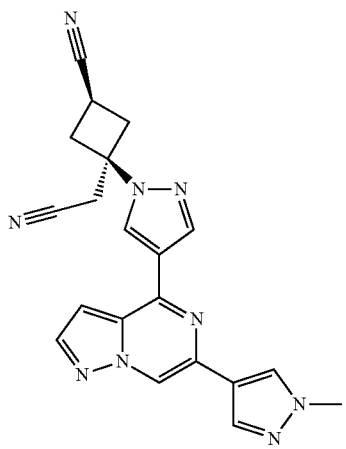 [SMILES: Cn1cc(-c2cn3nccc3c(-c3cnn([C@]4(CC#N)C[C@H](C#N)C4)c3)n2)cn1]

To a solution of (1s,3S)-3-(cyanomethyl)-3-(4-(4,4,5,5-tetramethyl-1,3,2-dioxaborolan-2-yl)-1H-pyrazol-1-yl)cyclobutane-1-carbonitrile (Preparation 91, 539 mg, 1.72 mmol) and 4-chloro-6-(1-methyl-1H-pyrazol-4-yl)pyrazolo[1,5-a]pyrazine (Preparation 11, 350 mg, 1.5 mmol) in 1,4-dioxane (7.5 mL) was added 2 M aq. $K_3PO_4$ (2.25 mL) at about 25° C. The mixture was placed under nitrogen, then XPhos Pd G2 (11.8 mg, 0.0150 mmol) was added. The mixture was heated at about 40° C. for about 6 h, then it was heated to about 80° C. to dissolve the precipitated product. The aqueous layer was removed while maintaining the temperature at about 80° C., then the 1,4-dioxane phase was added to EtOH (70 mL, previously preheated to about 50° C.). The mixture was stirred for about 10 min at about 50° C. before being removed from heat. Stirring at about 25° C. was continued for about 18 h. The solid was filtered and washed with EtOH (2×25 mL) and dried under vacuum to afford the title compound as a white solid (483 mg, 84%).

mp 217-220° C.

$^1$H NMR (400 MHz, DMSO-$d_6$) δ: 9.02 (s, 1H), 8.87 (s, 1H), 8.51 (s, 1H), 8.37 (s, 1H), 8.20 (s, 1H), 8.16 (s, 1H), 7.45 (s, 1H), 3.92 (s, 3H), 3.65-3.59 (m, 1H), 3.57 (s, 2H), 3.26-3.16 (m, 2H), 2.88 (m, 2H).

$^{13}$C NMR (101 MHz, DMSO-$d_6$) δ: 145.21, 142.50, 140.09, 137.15, 133.80, 131.39, 129.54, 129.24, 121.94, 121.03, 120.33, 117.69, 114.55, 99.94, 59.62, 39.28, 36.90, 27.42, 14.64.

LCMS m/z=384.2 [MH]$^+$

Example 20

(1r,3r)-3-(Cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile

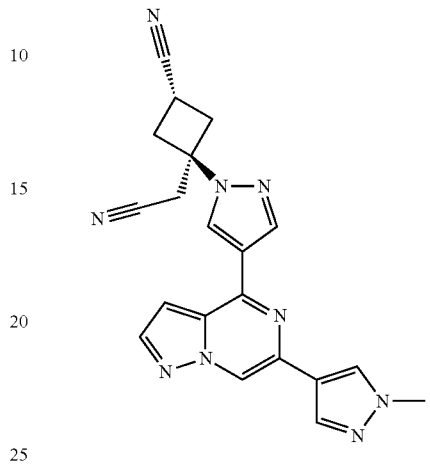

To a solution of (1r,3r)-3-(cyanomethyl)-3-(4-(4,4,5,5-tetramethyl-1,3,2-dioxaborolan-2-yl)-1H-pyrazol-1-yl)cyclobutane-1-carbonitrile (Preparation 91, 3.38 g, 10.8 mmol) and 4-chloro-6-(1-methyl-1H-pyrazol-4-yl)pyrazolo[1,5-a]pyrazine (Preparation 11, 2.20 g, 9.4 mmol) in 1,4-dioxane (47.1 mL) was added 2 M aq. $K_3PO_4$ (14.1 mL). Nitrogen was bubbled through the mixture for about 5 min at about 25° C., then XPhos Pd G2 (37.0 mg, 0.047 mmol) was added.

The mixture was heated at about 40° C. for about 18 h, then it was heated to about 80° C. to dissolve the precipitated product. The aqueous layer was removed while maintaining the temperature at about 80° C., then the 1,4-dioxane phase was added to EtOH (471 mL, previously preheated to about 50° C.). The mixture was stirred for about 10 min at about 50° C. before being removed from heat. Stirring at about 25° C. was continued for about 6 h. The solid was filtered and washed with EtOH (2×25 mL), water (2×50 mL), and EtOH (2×25 mL). The precipitate was dried under vacuum to afford the title compound as a white solid (3.61 g, 74%). The title compound (500 mg, 1.30 mmol) was heated in 1,4-dioxane (6.5 mL) at about 80° C. until all of the material was dissolved. 1,2-Bis(diphenylphosphino)ethane (7.8 mg, 0.019 mmol) was added and heating at about 80° C. was continued for about 4 hrs, then the 1,4-dioxane phase was added to EtOH (58.7 mL, previously preheated to about 50° C.). An additional 6.5 mL of preheated EtOH was used to rinse the reaction vessel. The mixture was removed from heat. Stirring at about 25° C. was continued for about 18 h. The solid was filtered and washed with EtOH (2×5 mL), water (5 mL), then EtOH (3×5 mL). The precipitate was dried under vacuum to afford the title compound as a white solid (450 mg, 90%).

Melting point 213-215° C.

$^1$H NMR (400 MHz, DMSO-$d_6$) δ: 9.02 (s, 1H) 8.92 (s, 1H) 8.52 (s, 1H) 8.37 (s, 1H) 8.19 (s, 1H) 8.16 (s, 1H) 7.45 (s, 1H) 3.91 (s, 3H) 3.55-3.65 (m, 1H) 3.52 (s, 2H) 3.22-3.38 (m, 2H) 2.85-3.00 (m, 2H).

$^{13}$C NMR (126 MHz, DMSO-$d_6$) δ: 145.17, 142.46, 140.20, 137.13, 133.78, 131.38, 129.82, 129.51, 122.28, 121.13, 120.33, 117.30, 114.54, 99.91, 61.51, 39.26, 36.26, 29.65, 16.05.

LCMS m/z=384.1 [MH]$^+$.

Preparation 60

(1r,3r)-3-(Cyanomethyl)-3-(3-methyl-4-(4,4,5,5-tetramethyl-1,3,2-dioxaborolan-2-yl)-1H-pyrazol-1-yl)cyclobutane-1-carbonitrile (trans isomer)

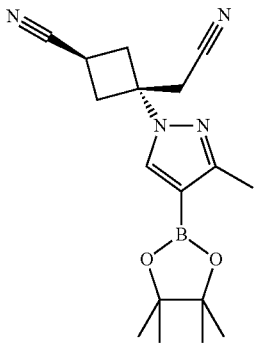 [SMILES: Cc1nn([C@]2(CC#N)C[C@@H](C#N)C2)cc1B1OC(C)(C)C(C)(C)O1]

and (1s,3s)-3-(Cyanomethyl)-3-(3-methyl-4-(4,4,5,5-tetramethyl-1,3,2-dioxaborolan-2-yl)-1H-pyrazol-1-yl)cyclobutane-1-carbonitrile (cis isomer)

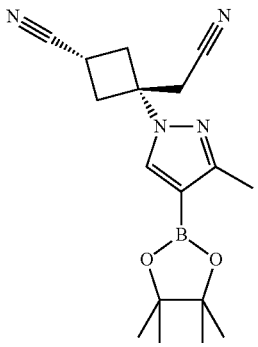 [SMILES: Cc1nn([C@]2(CC#N)C[C@H](C#N)C2)cc1B1OC(C)(C)C(C)(C)O1]

To a solution of 3-methyl-4-(4,4,5,5-tetramethyl-1,3,2-dioxaborolan-2-yl)-1H-pyrazole (600 mg, 2.88 mmol) and 3-(cyanomethylene)cyclobutane-1-carbonitrile (Preparation 27, 341 mg, 2.88 mmol) in MeCN (28.8 mL) was added DBU (439 mg, 2.88 mmol) at about 20° C. After about 18 hrs at about 20° C., the mixture was poured into EtOAc and 10% aq. K$_2$HPO$_4$. The EtOAc was separated and the aqueous phase was extracted twice more with EtOAc. The combined EtOAc extracts were washed with brine, dried (Na$_2$SO$_4$) and concentrated. The residue was purified by column chromatography to afford (1r,3r)-3-(cyanomethyl)-3-(3-methyl-4-(4,4,5,5-tetramethyl-1,3,2-dioxaborolan-2-yl)-1H-pyrazol-1-yl)cyclobutane-1-carbonitrile (trans isomer, 325 mg, 35%) $^1$H NMR (400 MHz, CDCl$_3$) δ: 7.79 (s, 1H), 3.17-3.28 (m, 3H), 3.16 (s, 2H), 2.81-2.89 (m, 2H), 2.39 (s, 3H), 1.32 (s, 12H).
LCMS m/z=327.2 [MH]$^+$
and (1s, 3s)-3-(cyanomethyl)-3-(3-methyl-4-(4,4,5,5-tetramethyl-1,3,2-dioxaborolan-2-yl)-1H-pyrazol-1-yl)cyclobutane-1-carbonitrile (cis isomer, 171 mg, 18%).
$^1$H NMR (400 MHz, CDCl$_3$) δ: 7.75 (s, 1H), 3.18-3.28 (m, 1H), 3.08-3.18 (m, 2H), 3.05 (s, 2H), 2.93-3.02 (m, 2H), 2.39 (s, 3H), 1.32 (s, 12H).
LCMS m/z=327.2 [MH]$^+$

Example 21

(1r,3r)-3-(Cyanomethyl)-3-(3-methyl-4-(6-(1-methyl-1H-pyrazol-4-yl)pyrazolo[1,5-a]pyrazin-4-yl)-1H-pyrazol-1-yl)cyclobutane-1-carbonitrile

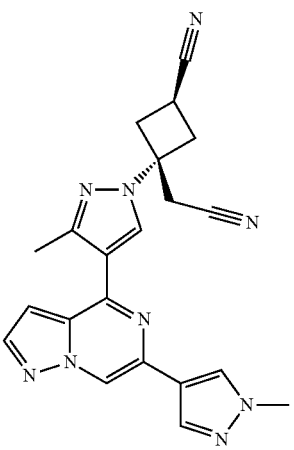 [SMILES: Cc1nn([C@]2(CC#N)C[C@@H](C#N)C2)cc1-c1nc(-c2cnn(C)c2)cn2nccc12]

To a solution of (1r,3r)-3-(cyanomethyl)-3-(3-methyl-4-(4,4,5,5-tetramethyl-1,3,2-dioxaborolan-2-yl)-1H-pyrazol-1-yl)cyclobutane-1-carbonitrile (Preparation 60, trans isomer, 209 mg, 0.64 mmol) in 1,4-dioxane (4.3 mL) was added 4-chloro-6-(1-methyl-1H-pyrazol-4-yl)pyrazolo[1,5-a]pyrazine (Preparation 11, 150 mg, 0.64 mmol) and 2 M aq. K$_3$PO$_4$ (0.96 mL). The mixture was purged with nitrogen for about 5 min, then XPhos Pd G2 (101 mg, 0.13 mmol) was added. The mixture was heated at about 40° C. for about 2 hrs, then concentrated. The residue was dissolved in EtOAc and the EtOAc was washed with water. The aqueous phase was extracted twice more with EtOAc, then once with DCM. The combined EtOAc and DCM extracts were dried (Na$_2$SO$_4$), concentrated, and the residue was purified by chromatography to afford a solid which was recrystallized from MeCN to afford the title compound (120 mg, 47%).
$^1$H NMR (400 MHz, DMSO-d$_6$) δ: 9.00 (s, 1H), 8.74 (s, 1H), 8.26 (s, 1H), 8.18 (s, 1H), 8.08 (s, 1H), 7.32 (s, 1H), 3.91 (s, 3H), 3.55 (quin, 1H), 3.48 (s, 2H), 3.22-3.30 (m, 2H), 2.84-2.93 (m, 2H), 2.63 (s, 3H).
LCMS m/z=398.3 [MH]$^+$

Preparation 61

4-Bromo-1-methyl-3-(((tetrahydro-2H-pyran-2-yl)oxy)methyl)-1H-pyrazole

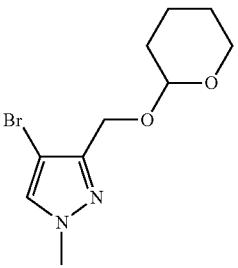

To a solution of 4-bromo-1-methyl-1H-pyrazole-3-methanol (720 mg, 3.77 mmol) in THF (30 mL) was added DHP (951 mg, 11.3 mmol) and PTSA (14 mg, 0.075 mmol). The solution was stirred at about 50° C. for about 16 hrs. The mixture was concentrated and the residue was purified by chromatography to afford the title compound as a colorless oil (1.0 g, 84%).

$^1$H NMR (400 MHz, CDCl$_3$) δ: 7.37 (s, 1H), 4.81 (t, 1H), 4.74 (d, 1H), 4.46 (d, 1H), 3.96-4.03 (m, 1H), 3.88 (s, 3H), 3.56-3.63 (m, 1H), 1.80-1.93 (m, 1H), 1.59-1.78 (m, 3H), 1.48-1.57 (m, 2H).

LCMS m/z=190.7 [MH-THP]$^+$

Preparation 62

(1s,3s)-3-(Cyanomethyl)-3-(4-(6-(1-methyl-3-(((tetrahydro-2H-pyran-2-yl)oxy)methyl)-1H-pyrazol-4-yl)pyrazolo[1,5-a]pyrazin-4-yl)-1H-pyrazol-1-yl)cyclobutane-1-carbonitrile

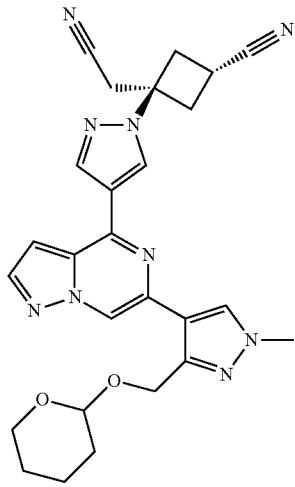 [SMILES: Cn1cc(-c2cn3nccc3c(-c3cnn([C@]4(CC#N)C[C@@H](C#N)C4)c3)n2)c(COC2CCCCO2)n1]

Part 1

To a solution of 4-bromo-1-methyl-3-(((tetrahydro-2H-pyran-2-yl)oxy)methyl)-1H-pyrazole (Preparation 61, 200 mg, 0.73 mmol) in 1,4-dioxane (10 mL) were added KOAc (313 mg, 3.19 mmol), and bis(pinacolato)diboron (405 mg, 1.59 mmol). The mixture was purged with nitrogen for about 5 min before the addition of Pd(dppf)Cl$_2$ (78 mg, 0.11 mmol). The mixture was heated at about 90° C. for about 18 hrs. The mixture was concentrated to afford an impure sample of 1-methyl-3-(((tetrahydro-2H-pyran-2-yl)oxy)methyl)-4-(4,4,5,5-tetramethyl-1,3,2-dioxaborolan-2-yl)-1H-pyrazole as a black oil (234 mg), which was used in Part 2 below without further purification.

Part 2

A mixture of (1r,3r)-3-(4-(6-chloropyrazolo[1,5-a]pyrazin-4-yl)-1H-pyrazol-1-yl)-3-(cyanomethyl)cyclobutane-1-carbonitrile (Preparation 75, 85 mg, 0.25 mmol), 1-methyl-3-(((tetrahydro-2H-pyran-2-yl)oxy)methyl)-4-(4,4,5,5-tetramethyl-1,3,2-dioxaborolan-2-yl)-1H-pyrazole (Part 1, 81 mg, 0.25 mmol), and 2 M aq. K$_3$PO$_4$ (1.0 mL) in 1,4-dioxane (3.0 mL) was purged with argon for about 2 min, after which XPhos Pd G2 (39 mg, 0.050 mmol) was added. The reaction mixture was heated at about 45° C. for about 45 min. The 1,4-dioxane phase was separated from the aqueous phase, which was extracted further with EtOAc (5 mL). The combined 1,4-dioxane and EtOAc extracts were dried (Na$_2$SO$_4$) and concentrated. The residue which was purified by chromatography to afford the title compound (50 mg, 40%).

$^1$H NMR (400 MHz, CDCl$_3$) δ: 8.92 (s, 1H), 8.45 (s, 1H), 8.33 (s, 1H), 8.07-8.10 (m, 1H), 8.00 (s, 1H), 6.96 (d, 1H), 5.02 (d, 1H), 4.87-4.91 (m, 1H), 4.70 (m, 1H), 4.59 (d, 1H), 4.51 (d, 1H), 3.99 (s, 3H), 3.51-3.62 (m, 2H), 3.34-3.44 (m, 1H), 3.29 (s, 2H), 2.99 (m, 2H), 1.80-1.96 (m, 3H), 1.68-1.80 (m, 3H).

LCMS m/z=498.3 [MH]$^+$

Example 22

(1r,3r)-3-(Cyanomethyl)-3-(4-(6-(3-(hydroxymethyl)-1-methyl-1H-pyrazol-4-yl)pyrazolo[1,5-a]pyrazin-4-yl)-1H-pyrazol-1-yl)cyclobutane-1-carbonitrile

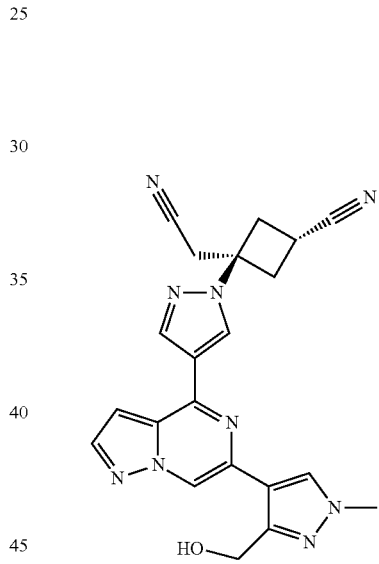

PTSA (10 mg, 0.052 mmol) was added to solution of (1s,3s)-3-(cyanomethyl)-3-(4-(6-(1-methyl-3-(((tetrahydro-2H-pyran-2-yl)oxy)methyl)-1H-pyrazol-4-yl)pyrazolo[1,5-a]pyrazin-4-yl)-1H-pyrazol-1-yl)cyclobutane-1-carbonitrile (Preparation 62, 50 mg, 0.10 mmol) in MeOH (10 mL). The reaction mixture was kept at about 20° C. for about 18 hrs. The precipitated solid was filtered to afford the title compound (20 mg, 48%).

$^1$H NMR (400 MHz, DMSO-d$_6$) δ: 9.00 (s, 1H), 8.91 (s, 1H), 8.48 (s, 1H), 8.35 (s, 1H), 8.22 (d, 1H), 7.47 (d, 1H), 5.41 (br. s., 1H), 4.66 (s, 2H), 3.88 (s, 3H), 3.54-3.62 (m, 1H), 3.52 (s, 2H), 3.28-3.34 (m, 2H), 2.90-2.98 (m, 2H).

LCMS m/z=414.4 [MH]$^+$

Preparation 63

(1r,3r)-3-(Cyanomethyl)-3-(4-(6-(1-methyl-3-nitro-1H-pyrazol-4-yl)pyrazolo[1,5-a]pyrazin-4-yl)-1H-pyrazol-1-yl)cyclobutane-1-carbonitrile

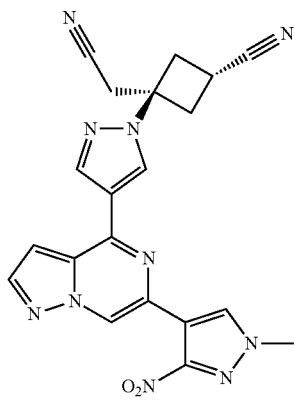 [SMILES: Cn1cc(-c2cn3nccc3c(-c3cnn([C@]4(CC#N)C[C@@H](C#N)C4)c3)n2)c([N+](=O)[O-])n1]

Part 1

To a solution of 4-bromo-1-methyl-3-nitro-1H-pyrazole (200 mg, 0.97 mmol) in 1,4-dioxane (10 mL) were added KOAc (285 mg, 2.90 mmol), and bis(pinacolato)diboron (368 mg, 1.45 mmol). The mixture was purged with nitrogen for about 5 min, after which Pd(dppf)Cl$_2$ (70.8 mg, 0.097 mmol) was added. The mixture was heated at about 90° C. for about 18 h. The mixture was concentrated to afford impure 1-methyl-3-nitro-4-(4,4,5,5-tetramethyl-1,3,2-dioxaborolan-2-yl)-1H-pyrazole as a black oil, which was used without further purification in Part 2.

Part 2

A mixture of (1r,3r)-3-(4-(6-chloropyrazolo[1,5-a]pyrazin-4-yl)-1H-pyrazol-1-yl)-3-(cyanomethyl)cyclobutane-1-carbonitrile (Preparation 75, 130 mg, 0.38 mmol), 1-methyl-3-nitro-4-(4,4,5,5-tetramethyl-1,3,2-dioxaborolan-2-yl)-1H-pyrazole (Part 1, 97 mg, 0.38 mmol), and 2 M aq. K$_3$PO$_4$ (2.0 mL) in 1,4-dioxane (6.0 mL) was purged with argon for about 2 min, after which XPhos Pd G2 (60.6 mg, 0.077 mmol) was added. The mixture was heated at about 45° C. for about 45 min. The 1,4-dioxane phase was separated from the aqueous phase, which was extracted further with EtOAc (10 mL). The combined 1,4-dioxane and EtOAc extracts were dried (Na$_2$SO$_4$) and concentrated. The residue was purified by chromatography to afford the title compound (120 mg, 72%).

$^1$H NMR (400 MHz, DMSO-d$_6$) δ: 9.10 (s, 1H), 8.90 (s, 1H), 8.56 (s, 1H), 8.43 (s, 1H), 8.32 (d, 1H), 7.56 (br. s., 1H), 4.05 (s, 3H), 3.54-3.60 (m, 1H), 3.51 (s, 2H), 3.18-3.29 (m, 2H), 2.88-2.98 (m, 2H).

LCMS m/z=429.4 [MH]$^+$

Example 23

(1r,3r)-3-(4-(6-(3-Amino-1-methyl-1H-pyrazol-4-yl)pyrazolo[1,5-a]pyrazin-4-yl)-1H-pyrazol-1-yl)-3-(cyanomethyl)cyclobutane-1-carbonitrile

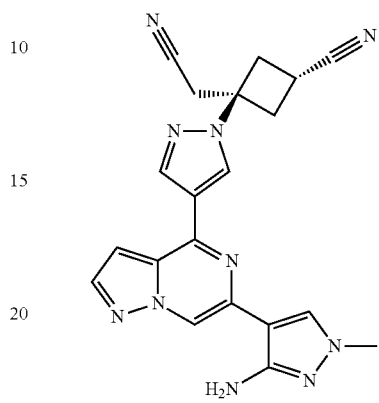

To a solution of (1r,3r)-3-(cyanomethyl)-3-(4-(6-(1-methyl-3-nitro-1H-pyrazol-4-yl)pyrazolo[1,5-a]pyrazin-4-yl)-1H-pyrazol-1-yl)cyclobutane-1-carbonitrile (Preparation 63, 120 mg, 0.28 mmol) in EtOH (3 mL) and water (0.5 mL) were added NH$_4$Cl (90 mg, 1.68 mmol) and iron powder (50 mg, 0.90 mmol). The reaction was stirred at about 60° C. for about 18 hrs, after which additional portions of iron powder and NH4Cl were added. The mixture was heated at about 100° C. for about 3 hrs. The mixture was concentrated and hot EtOH (20 mL) was added. The undissolved solids were removed by filtration. The filtrate was concentrated and the residue was purified by chromatography to afford the title compound as a white solid (10 mg, 9%).

$^1$H NMR (400 MHz, CD$_3$OD) δ: 8.74 (s, 1H), 8.67 (s, 1H), 8.40 (s, 1H), 8.08 (d, 1H), 7.94 (s, 1H), 7.24 (d, 1H), 3.77 (s, 3H), 3.47-3.55 (m, 1H), 3.43 (s, 2H), 3.34-3.41 (m, 2H), 2.98 (dd, 2H).

LCMS m/z=399.4 [MH]$^+$

Preparation 64

3,5-Dibromo-1-methyl-1H-pyrazole

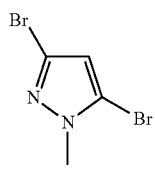

A solution of 3,5-dibromopyrazole (6.5 g, 28.7 mmol) in THF (30 mL) was added dropwise to an ice-cooled suspension of NaH (2.88 g, 60% in mineral oil, 71.9 mmol) in THF (45 mL). The mixture was stirred at about 0° C. for about 1 hrs. Iodomethane (5.37 mL, 86.3 mmol) was added and the mixture was stirred at about 0° C. for about 3 hrs, then stirring was continued at about 15° C. for about 2 hrs. The mixture was poured into saturated aq. NH$_4$Cl (20 mL) and extracted with EtOAc (40 mL). The EtOAc extract was washed with brine (20 mL), dried (Na$_2$SO$_4$), and concentrated. The residue was purified by chromatography to afford the title compound as a colorless oil (5.5 g, 79%).

$^1$H NMR (400 MHz, CDCl$_3$) δ: 6.31 (s, 1H), 3.87 (s, 3H).
LCMS m/z=240.6 [MH]$^+$ ($^{79}$Br, $^{81}$Br isotope)

Preparation 65

3-Bromo-1-methyl-1H-pyrazole-5-carboxylic acid

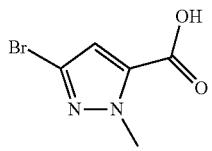

A solution of 3,5-dibromo-1-methyl-1H-pyrazole (Preparation 64, 3.0 g, 12.5 mmol) Era THF (30 mL) was treated dropwise with n-BuLi (2.5 M, 6.25 mL, 15.6 mmol) at about −70° C. After about 30 min at this temperature, a solution of CO$_2$ in THF (30 mL) was added dropwise while maintaining the internal temperature below about −65° C. The mixture was stirred at this temperature for about 1 hrs. The reaction mixture was then poured into 1 M aq. HCl (50 mL) and the mixture was partially concentrated to remove most of the THF. The aqueous layer was extracted with DCM (50 mL). The DCM extract was dried (Na$_2$SO$_4$) and concentrated to afford the title compound as a yellow solid (2.1 g, 81%).

$^1$HNMR (400 MHz, DMSO-d$_6$) δ: 13.70 (br s, 1H), 6.95 (s, 1H), 4.04 (s, 3H).
LCMS m/z=206.9 [MH]$^+$ ($^{81}$Br isotope)

Preparation 66 tert-Butyl (3-bromo-1-methyl-1H-pyrazol-5-yl)carbamate

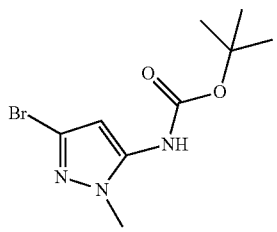

Diphenylphosphoryl azide (18.8 g, 68.5 mmol) was added to a solution of 5-bromo-2-methyl-2H-pyrazole-3-carboxylic acid (Preparation 65, 7.02 g, 34.2 mmol) and DIPEA (11.9 mL, 68.5 mmol) in t-butanol (114 mL). The mixture was stirred at about 45° C. for about 30 min, then heated under reflux for about 5 hrs. The cooled mixture was diluted with EtOAc (60 mL) and washed with saturated aq. NaHCO$_3$ (2×30 mL) and brine (20 mL). The EtOAc extract was concentrated and the residue was purified by chromatography to afford the title compound as a yellow solid (4.80 g, 51%).

$^1$H NMR (400 MHz, DMSO-d$_6$) δ: 6.28 (br s, 1H), 6.18 (s, 1H), 3.73 (s, 3H), 1.50 (s, 9H).
LCMS m/z=221.7 [MH-C$_4$H$_8$]$^+$ ($^{81}$Br isotope)

Preparation 67

3-Bromo-1-methyl-5-(diBoc)-amino-1H-pyrazole

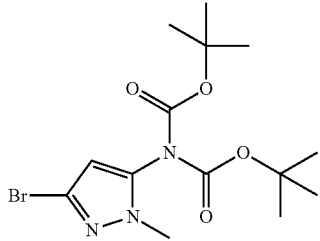 [SMILES: Cn1nc(Br)cc1N(C(=O)OC(C)(C)C)C(=O)OC(C)(C)C]

Di-tert-butyl dicarbonate (1.58 g, 7.24 mmol) was added to a solution of tert-butyl (3-bromo-1-methyl-1H-pyrazol-5-yl)carbamate (Preparation 66, 2.0 g, 7.24 mmol), TEA (4.04 mL, 29.0 mmol), and DMAP (177 mg, 1.45 mmol) in DCM (40 mL). The mixture was stirred at about 20° C. for about 18 hrs. Water (25 mL) was added and the mixture was extracted with DCM (2×30 mL). The combined DCM extracts were concentrated and the residue was purified chromatography to afford the title compound (1.85 g, 67)%.

$^1$H NMR (400 MHz, CDCl$_3$) δ: 6.06-6.20 (m, 1H), 3.64 (s, 3H), 1.44 (s, 18H).
LCMS m/z=378.2 [MH]$^+$ ($^{81}$Br isotope)

Example 24

2-((1r,3s)-1-(4-(6-(5-Amino-1-methyl-1H-pyrazol-3-yl)pyrazolo[1,5-a]pyrazin-4-yl)-1H-pyrazol-1-yl)-3-methoxycyclobutyl)acetonitrile

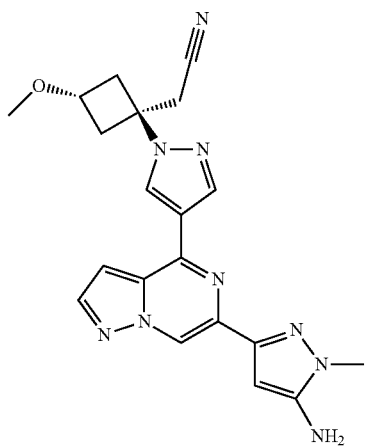

Part 1

A mixture of 3-bromo-1-methyl-5-(diBoc)-amino-1H-pyrazole (Preparation 67, 1200 mg, 3.19 mmol), KOAc (988 mg, 9.57 mmol) and bis(pinacolato)diboron (1210 mg, 4.78 mmol) in 1,4-dioxane (15 mL) was purged with argon for about 5 minutes before XPhos Pd G2 (502 mg, 0.64 mmol) was added. The reaction mixture was heated at about 65° C. for about 3.5 hrs, then 2-((is, 3r)-1-(4-(6-chloropyrazolo[1,5-a]pyrazin-4-yl)-1H-pyrazol-1-yl)-3-methoxycyclo-butyl)acetonitrile (Preparation 100, 1090 mg, 3.19 mmol), 2 M aq. K$_3$PO$_4$ (4.78 mL) and XPhos Pd G2 (502 mg, 0.64 mmol)

were added. The mixture was purged with argon again, then heated at about 80° C. for about 1 hrs. EtOAc was added and the phases were separated. The aqueous phase was extracted twice more with EtOAc and the combined EtOAc extracts were concentrated. The residue was purified by chromatography to afford a mixture of mono- and di-BOC intermediates (710 mg, 36%) which was used in Part 2.

Part 2

TFA (6 mL, 80 mmol) added to a solution of the mono- and di-BOC intermediates of Part 1 (710 mg, 1.18 mmol) in DCM (6 mL) at about 20° C. After about 1 hrs, the mixture was concentrated. DCM was added, followed by sufficient saturated aq. NaHCO$_3$ to render the solution pH basic. The phases were separated and the aqueous phase was extracted twice more with DCM. The combined DCM extracts were dried (Na$_2$SO$_4$) and concentrated. An equivalent reaction using the compound of Part 1 (220 mg, 0.36 mmol) and TFA (2 mL, 30 mmol) in DCM (2 mL) was combined with the material from the reaction above and the combined samples were purified by chromatography to afford the title compound as a clear gum (470 mg, 99%).

$^1$H NMR (400 MHz, DMSO-d$_6$) δ: 8.81 (s, 1H), 8.73 (s, 1H), 8.40 (s, 1H), 8.21 (d, 1H), 7.44 (d, 1H), 5.33 (br. s, 2H), 3.94-4.02 (m, 1H), 3.62 (s, 3H), 3.44 (s, 2H), 3.21 (s, 3H), 3.14-3.20 (m, 2H), 2.39-2.45 (m, 2H).

LCMS m/z=404.5 [MH]$^+$

Preparation 68

Diethyl 4-bromo-1H-pyrazole-3,5-dicarboxylate

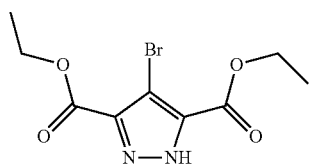 [SMILES: CCOC(=O)c1n[nH]c(C(=O)OCC)c1Br]

A mixture of 1H-pyrazole-3,5-dicarboxylic acid diethyl ester (4.0 g, 18.85 mmol) and N-bromosuccinimide (4.03 g, 22.6 mmol) in a mixture of conc. nitric acid and glacial acetic acid (12.0 mL, 5:95 v/v) was heated by microwave irradiation at about 120° C. for about 20 minutes. A total of total of 13.0 g (61.26 mmol) of 1H-pyrazole-3,5-dicarboxylic acid diethyl ester starting material was processed in this manner in parallel batches. The resulting brown crude reaction mixtures were combined, poured into water (260 mL), and treated with sufficient NaHCO$_3$ to render the solution pH basic. The mixture was extracted with EtOAc (3×300 mL). The combined EtOAc extracts were dried (Na$_2$SO$_4$) and concentrated to afford the title compound as an off-white solid (17.0 g, 95%).

$^1$H NMR (400 MHz, CDCl$_3$) δ: 8.79 (br. s., 1H), 4.44 (q, 4H), 1.42 (t, 6H).

LCMS m/z=290.7 [MH]$^+$ ($^{79}$Br isotope)

Preparation 69

Diethyl 4-bromo-1-(2-(1-methyl-1H-pyrazol-4-yl)-2-oxoethyl)-1H-pyrazole-3,5-dicarboxylate

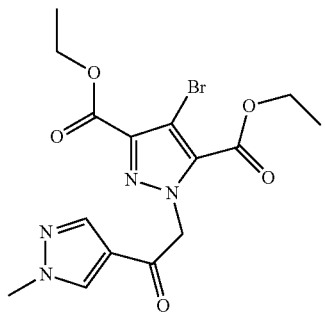 [SMILES: CCOC(=O)c1nn(CC(=O)c2cnn(C)c2)c(C(=O)OCC)c1Br]

A solution of 4-bromo-1H-pyrazole-3,5-dicarboxylic acid diethyl ester (Preparation 68, 9.66 g, 33.18 mmol) and 2-bromo-1-(1-methyl-1H-pyrazol-4-yl)-ethanone (Preparation 6, 6.0 g, 29.55 mmol) in MeCN (140 mL) was treated with K$_2$CO$_3$ (5.31 g, 38.40 mmol) and the reaction mixture was stirred at about 25° C. for about 16 hrs. Water (100 mL) was added and the mixture was extracted with EtOAc (3×100 mL). The combined EtOAc extracts were dried (Na$_2$SO$_4$) and concentrated. The residue was purified by chromatography to afford the title compound as a white solid (10.0 g, 82%).

$^1$HNMR (400 MHz, CDCl$_3$) δ: 7.95 (s, 1H), 7.92 (s, 1H), 5.82 (s, 2H), 4.43 (q, 2H), 4.36 (q, 2H), 3.96 (s, 3H), 1.45 (t, 3H), 1.35 (t, 3H).

LCMS m/z=436.8 [MNa]$^+$ ($^{81}$Br isotope)

Preparation 70

Diethyl 4-methyl-1-(2-(1-methyl-1H-pyrazol-4-yl)-2-oxoethyl)-1H-pyrazole-3,5-dicarboxylate

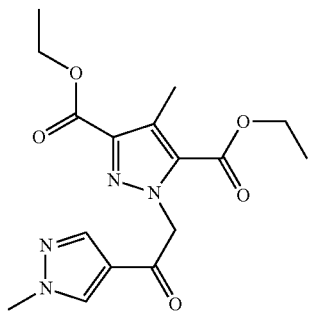 [SMILES: CCOC(=O)c1nn(CC(=O)c2cnn(C)c2)c(C(=O)OCC)c1C]

A mixture of K$_2$CO$_3$ (11.0 g, 79.9 mmol) and 4-bromo-1H-[2-(1-methyl-1H-pyrazol-4-yl)-2-oxo-ethyl]-1H-pyrazole-3,5-dicarboxylic acid diethyl ester (Preparation 69, 11.0 g, 26.62 mmol) in DMF (133.0 mL) was purged with nitrogen at about 25° C., after which Pd(dppf)Cl$_2$ (1950 mg, 2.66 mmol) and trimethylboroxine (10.0 g, 79.9 mmol) were added and the solution was heated at about 110° C. for about 5 hrs. The cooled reaction was diluted with EtOAc (100 mL) and the resulting mixture was washed with brine (2×100 mL), dried (Na$_2$SO$_4$), and concentrated. The residue was purified by chromatography to afford the title compound as a yellow solid (5.45 g, 50%).

$^1$H NMR (400 MHz, CDCl$_3$) δ: 7.92 (s, 1H), 7.90 (s, 1H), 5.78 (s, 2H), 4.41 (q, 2H), 4.28 (q, 2H), 3.95 (s, 3H), 2.58 (s, 3H), 1.39 (t, 3H), 1.31 (t, 3H).

LCMS m/z=348.9 [MH]$^+$

Preparation 71

Ethyl 4-hydroxy-3-methyl-6-(1-methyl-1H-pyrazol-4-yl)pyrazolo[1,5-a]pyrazine-2-carboxylate

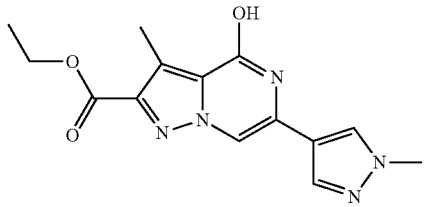 [SMILES: CCOC(=O)c1nn2cc(-c3cnn(C)c3)nc(O)c2c1C]

4-Methyl-[2-(1-methyl-1H-pyrazol-4-yl)-2-oxo-ethyl]-1H-pyrazole-3,5-dicarboxylic acid diethyl ester (Preparation 70, 5.35 g, 15.36 mmol) was mixed with dry EtOH (15 mL) and concentrated. The resulting solid was dissolved in EtOH (40 mL) and NH$_4$OAc (3.55 g, 46.1 mmol) was added. The reaction mixture was heated at about 130° C. in an autoclave for about 8 hrs. After cooling, the mixture was filtered and the precipitate was dried to afford the title compound as an off-white solid (3.40 g, 73%).

$^1$H NMR (400 MHz, DMSO-d$_6$) δ: 11.45 (br. s., 1H), 8.27 (s, 1H), 8.08 (s, 1H), 8.02 (s, 1H), 4.31 (m, 2H), 3.87 (s, 3H), 2.61 (s, 3H), 1.24-1.40 (m, 3H).

LCMS m/z=301.8 [MH]$^+$

Preparation 72

4-Hydroxy-3-methyl-6-(1-methyl-1H-pyrazol-4-yl)-pyrazolo[1,5-a]pyrazine-2-carboxylic acid

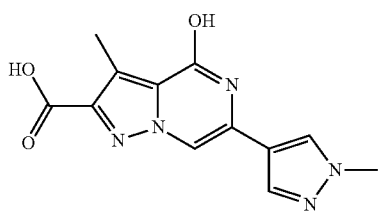 [SMILES: Cc1c(C(=O)O)nn2cc(-c3cnn(C)c3)nc(O)c12]

Lithium hydroxide monohydrate (1.42 g, 33.9 mmol) was added to a suspension of 4-hydroxy-3-methyl-6-(1-methyl-1H-pyrazol-4-yl)-pyrazolo[1,5-a]pyrazine-2-carboxylic acid ethyl ester (Preparation 71, 3.40 g, 11.3 mmol) in THF (50 mL), MeOH (50 mL) and water (25 mL). The mixture was stirred at about 60° C. for about 4 hrs. The cooled mixture was concentrated and water (50 mL) was added. The pH of the mixture was adjusted to about 2 by the addition of 12 M aq. HCl. The resulting precipitate was filtered and washed with water (50 mL), then dried under vacuum to afford the title compound as a solid.

$^1$HNMR (400 MHz, DMSO-d$_6$) δ: 12.90-13.20 (br. s, 1H), 11.40 (s, 1H), 8.30 (s, 1H), 8.02 (m, 2H), 3.90 (s, 3H), 2.60 (s, 3H).

LCMS m/z=301.8 [MH]$^+$, 323.8 [MNa]$^+$

Preparation 73

3-Methyl-6-(1-methyl-1H-pyrazol-4-yl)-pyrazolo[1,5-a]pyrazin-4-ol

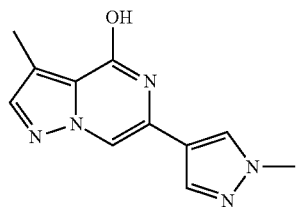

4-Hydroxy-3-methyl-6-(1-methyl-1H-pyrazol-4-yl)-pyrazolo[1,5-a]pyrazine-2-carboxylic acid (Preparation 72, 2.58 g, 9.44 mmol) was added in portions to preheated sulfolane (18.9 mL) at about 280° C. Once the addition was complete, the mixture was stirred for an additional 1 hrs at about 280° C. The cooled mixture was purified directly by chromatography on silica gel (eluting with petroleum ether: EtOAc (100:0 to 50:50), then DCM:MeOH (91:9)) to afford the title compound as a yellow solid (1.50 g, 69%).

$^1$HNMR (400 MHz, DMSO-d$_6$) δ: 11.20 (s, 1H), 8.38 (s, 1H), 8.02 (s, 1H), 7.96 (s, 1H), 7.70 (s, 1H), 3.85 (s, 3H), 2.40 (s, 3H).

Preparation 74

4-Chloro-3-methyl-6-(1-methyl-1H-pyrazol-4-yl)-pyrazolo[1,5-a]pyrazine

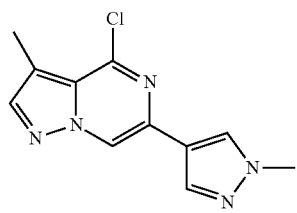 [SMILES: Cc1cnn2cc(-c3cnn(C)c3)nc(Cl)c12]

To a suspension of 3-methyl-6-(1-methyl-1H-pyrazol-4-yl)-pyrazolo[1,5-a]pyrazin-4-ol (Preparation 73, 1.40 g, 6.11 mmol) in MeCN (60.0 mL) was added POCl$_3$ (4.68 g, 30.5 mmol). The reaction mixture was heated at about 80° C. for about 16 hrs. After cooling, the mixture was poured into water (200 mL) at about 25° C. The mixture was adjusted to about pH 9 by the addition of saturated aq. NaHCO$_3$ (200 mL), then extracted with EtOAc (5×100 mL). The combined EtOAc extracts were dried (Na$_2$SO$_4$) and concentrated. The residue was purified by chromatography, then further purified by HPLC to afford the title compound as a white solid (163 mg, 11%).

$^1$H NMR (400 MHz, CDCl$_3$) δ: 8.37 (s, 1H), 7.89 (s, 1H), 7.85 (s, 1H), 7.80 (s, 1H), 3.96 (s, 3H), 2.57 (s, 3H). LCMS m/z=247.7 [MH]$^+$ (Cl$^{35}$ isotope)

Example 25

(1r,3r)-3-(Cyanomethyl)-3-(4-(3-methyl-6-(1-methyl-1H-pyrazol-4-yl)pyrazolo[1,5-a]pyrazin-4-yl)-1H-pyrazol-1-yl)cyclobutane-1-carbonitrile

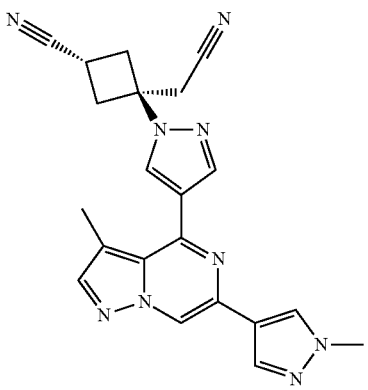 [SMILES: Cc1cnn2cc(-c3cnn(C)c3)nc(-c3cnn([C@]4(CC#N)C[C@@H](C#N)C4)c3)c12]

To a solution of 4-chloro-3-methyl-6-(1-methyl-1H-pyrazol-4-yl)-pyrazolo[1,5-a]pyrazine (Preparation 74, 98 mg, 0.40 mmol) and (1r,3r)-3-(cyanomethyl)-3-(4-(4,4,5,5-tetramethyl-1,3,2-dioxaborolan-2-yl)-1H-pyrazol-1-yl)cyclobutane-1-carbonitrile (Preparation 91, 247 mg, 0.79 mmol) in 1,4-dioxane (9 mL) was added 2 M aq. K$_3$PO$_4$ (0.59 mL) at about 25° C. and the mixture was purged with nitrogen for about 2 min before XPhos Pd G2 (62.3 mg, 0.079 mmol) was added. The mixture was purged with nitrogen for about 3 min, then heated at about 80° C. for about 16 hrs. The mixture was filtered and concentrated. The residue was purified by chromatography, then further purified by HPLC to afford the title compound as a light yellow solid (56 mg, 36%).

$^1$H NMR (400 MHz, DMSO-d$_6$): δ: 8.98 (s, 1H), 8.94 (s, 1H), 8.60 (s, 1H), 8.27 (s, 1H), 8.22 (s, 1H), 8.10 (s, 1H), 7.98 (s, 1H), 3.90 (s, 3H), 3.52-3.57 (m, 3H), 3.19-3.26 (m, 2H), 2.91-2.97 (m, 2H), 3.06 (s, 3H).
LCMS m/z=398.0 [MH]$^+$

Preparation 75

(1r,3r)-3-(4-(6-Chloropyrazolo[1,5-a]pyrazin-4-yl)-1H-pyrazol-1-yl)-3-(cyanomethyl)cyclobutane-1-carbonitrile

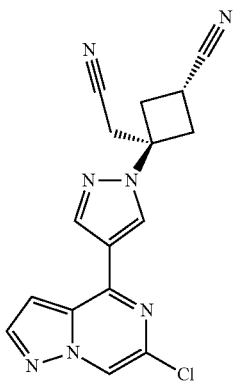 [SMILES: N#CC[C@]1(n2cc(-c3nc(Cl)cn4nccc34)cn2)C[C@H](C#N)C1]

A mixture of 4,6-dichloropyrazolo[1,5-a]pyrazine (Preparation 4, 350 mg, 1.86 mmol), (1r,3r)-3-(cyanomethyl)-3-(4-(4,4,5,5-tetramethyl-1,3,2-dioxaborolan-2-yl)-1H-pyrazol-1-yl)cyclobutane-1-carbonitrile, (Preparation 91, trans isomer, 581 mg, 1.86 mmol), and 2 M aq. K$_3$PO$_4$ (2.79 mL) in 1,4-dioxane (10 mL) was purged with argon for about 5 min, after which bis(tri-t-butylphosphine)palladium(0) (48.0 mg, 0.093 mmol) was added. The mixture was kept at about 25° C. for about 2 hrs then filtered. The precipitate was washed with Et$_2$O and dried. The filtrate was concentrated, triturated with Et$_2$O, filtered, washed with Et$_2$O and dried. The two precipitates were combined to afford the title compound as a white solid (605 mg, 96%).

$^1$H NMR (400 MHz, DMSO-d$_6$) δ: 9.05 (d, 1H), 8.93 (s, 1H), 8.46 (s, 1H), 8.32 (d, 1H), 7.61 (d, 1H), 3.55-3.62 (m, 1H), 3.54 (s, 2H), 3.24-3.32 (m, 2H), 2.89-3.00 (m, 2H).
LCMS m/z=338.2 [MH]$^+$

Example 26

(1r,3r)-3-(Cyanomethyl)-3-(4-(6-(5-methyl-1H-pyrazol-3-yl)pyrazolo[1,5-a]pyrazin-4-yl)-1H-pyrazol-1-yl)cyclobutane-1-carbonitrile

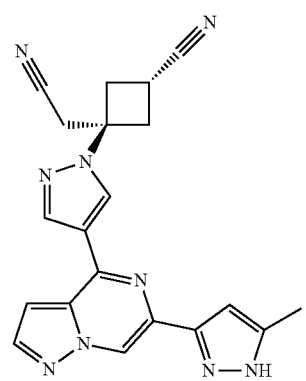 [SMILES: Cc1cc(-c2cn3nccc3c(-c3cnn([C@]4(CC#N)C[C@@H](C#N)C4)c3)n2)n[nH]1]

Part 1

A mixture of (1r,3r)-3-(4-(6-chloropyrazolo[1,5-a]pyrazin-4-yl)-1H-pyrazol-1-yl)-3-(cyanomethyl)cyclobutane-1-carbonitrile (Preparation 75, 85 mg, 0.25 mmol), 3-methyl-1-(tetrahydro-2H-pyran-2-yl)-5-(4,4,5,5-tetramethyl-1,3,2-dioxaborolan-2-yl)-1H-pyrazole (Preparation 93, 73 mg, 0.25 mmol), and 2 M aq. K$_3$PO$_4$ (1.0 mL) in 1,4-dioxane (3.0 mL) was purged with argon for about 2 min, after which XPhos Pd G2 (39.6 mg, 0.050 mmol) was added. The mixture was heated at about 45° C. for about 45 min before being cooled and concentrated. The residue was purified by chromatography to afford (1r,3r)-3-(cyanomethyl)-3-(4-(6-(5-methyl-1-(tetrahydro-2H-pyran-2-yl)-1H-pyrazol-3-yl)pyrazolo[1,5-a]pyrazin-4-yl)-1H-pyrazol-1-yl)cyclobutane-1-carbonitrile (26 mg, 22%), which was used directly in Part 2.
LCMS m/z=384.3 [MH-THP]$^+$ Part 2

TFA (1 mL) was added to a solution of (1r,3r)-3-(cyanomethyl)-3-(4-(6-(5-methyl-1-(tetrahydro-2H-pyran-2-yl)-1H-pyrazol-3-yl)pyrazolo[1,5-a]pyrazin-4-yl)-1H-pyrazol-1-yl)cyclobutane-1-carbonitrile (26 mg, 0.055 mmol) in DCM (2 mL). The reaction mixture was heated to about 50° C. for about 1 hrs. The mixture was concentrated and the residue was concentrated twice with toluene (5 mL each time). The residue was then purified by chromatography to afford a solid, which was further triturated with ether to afford the title compound (8 mg, 38%).

¹H NMR (400 MHz, CD₃CN) δ: 8.87 (s, 1H), 8.66 (s, 1H), 8.48 (s, 1H), 8.15 (d, 1H), 7.23 (s, 1H), 6.73 (s, 1H), 3.46 (dd, 1H), 3.36 (s, 2H), 3.32-3.41 (m, 2H), 2.98 (dd, 2H), 2.37 (s, 3H). LCMS m/z=384.4 [MH]⁺

Example 27

2-((1s,3r)-1-(4-(6-(5-(Hydroxymethyl)-1H-pyrazol-3-yl)pyrazolo[1,5-a]pyrazin-4-yl)-1H-pyrazol-1-yl)-3-methoxycyclobutyl)acetonitrile A solution of 2-((1s,3r)-1-(4-(6-chloropyrazolo[1,5-a]pyrazin-4-yl)-1H-pyrazol-1-yl)-3-methoxycyclobutyl)acetonitrile (Preparation 82, 100 mg, 0.29 mmol), and (3-(tributylstannyl)-1H-pyrazol-5-yl)methanol (Preparation 32, 113 mg, 0.29 mmol) in 1,4-dioxane (2 mL) was purged with argon for 5 min, followed by the addition of XPhos Pd G2 (45.9 mg, 0.058 mmol). The mixture was heated at about 80° C. for about 18 hrs. The resulting precipitate was filtered, washed with 1,4-dioxane and Et₂O, and dried to afford the title compound as a white solid (62 mg, 53%).

¹H NMR (400 MHz, CD₃CN) δ: 8.86 (s, 1H), 8.58 (s, 1H), 8.44 (s, 1H), 8.13 (d, 1H), 7.21 (d, 1H), 6.85 (s, 1H), 4.65 (d, 2H), 4.05 (quin, 1H), 3.27 (s, 3H), 3.21 (s, 2H), 2.90-2.99 (m, 2H), 2.67-2.76 (m, 2H).

LCMS m/z=405.3 [MH]⁺

Example 28

2-((1r,3s)-1-(4-(6-(5-(Hydroxymethyl)-1H-pyrazol-3-yl)pyrazolo[1,5-a]pyrazin-4-yl)-1H-pyrazol-1-yl)-3-methoxycyclobutyl)acetonitrile

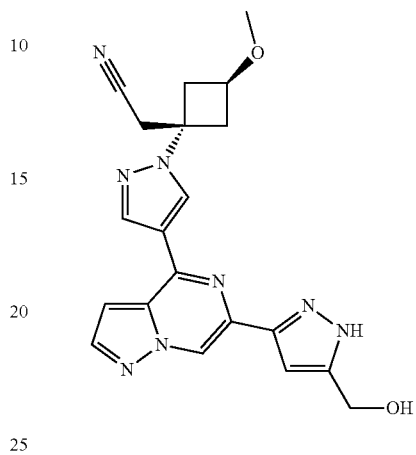

A solution of 2-((1r,3s)-1-(4-(6-chloropyrazolo[1,5-a]pyrazin-4-yl)-1H-pyrazol-1-yl)-3-methoxycyclobutyl)acetonitrile (Preparation 39; 1000 mg, 2.92 mmol) and (3-(tributylstannyl)-1H-pyrazol-5-yl)methanol (Preparation 32, 1130 mg, 2.92 mmol) in 1,4-dioxane (2 mL) was purged with argon for 5 min, followed by the addition of XPhos Pd G2 (45.9 mg, 0.058 mmol). The mixture was heated at about 80° C. for about 18 hrs. The precipitate was filtered and then purified by chromatography to afford an off white solid. The solid was heated in sufficient boiling EtOH until it was entirely dissolved, and then stirred for about 18 hrs at about 20° C. The precipitate was filtered and dried under vacuum to afford the title compound as a crystalline solid (507 mg, 43%).

¹H NMR (400 MHz, CD₃CN) δ: 11.48 (br. s.), 8.89 (s), 8.65 (s), 8.46 (s), 8.15 (d), 7.23 (s), 6.87 (s), 4.67 (d), 4.08 (quin), 3.31 (s), 3.30 (s), 3.15-3.25 (m), 2.53 (dd).

LCMS m/z=405.3 [MH]⁺

Preparation 76

Ethyl 5-(tributylstannyl)isoxazole-3-carboxylate

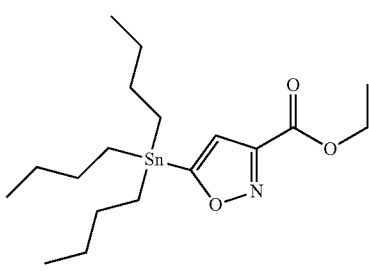 [SMILES: CCC[CH2][Sn]([CH2]CCC)([CH2]CCC)[c]1cc(C(=O)OCC)no1]

TEA (0.69 mL, 4.95 mmol) was added dropwise to an ice-cold solution of ethyl 2-chloro-2-(hydroxyimino)acetate (500 mg, 3.30 mmol) and ethynyltributylstannane (1040 mg, 3.30 mmol) in Et₂O (10 mL). The reaction mixture was warmed to about 20° C. and kept for about 18 hrs. The mixture was concentrated and the residue was purified by chromatography to afford the title compound as a colorless oil (810 mg, 57%).

$^1$H NMR (400 MHz, CDCl$_3$) δ: 6.80 (s, 1H), 6.77-6.84 (m, 1H), 4.45 (q, 2H), 1.51-1.63 (m, 6H), 1.43 (t, 3H), 1.34 (dq, 6H), 1.15-1.26 (m, 6H), 0.90 (t, 9H).

LCMS m/z=454.2 [MNa]$^+$ ($^{120}$Sn isotope)

Preparation 77

Ethyl 5-(4-(1-((1r,3r)-3-cyano-1-(cyanomethyl)cyclobutyl)-1H-pyrazol-4-yl)pyrazolo[1,5-a]pyrazin-6-yl)isoxazole-3-carboxylate

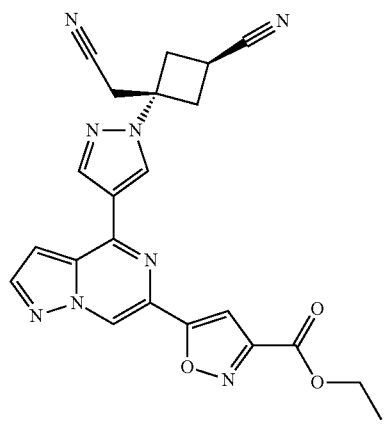 [SMILES: CCOC(=O)c1cc(-c2cn3nccc3c(-c3cnn([C@]4(CC#N)C[C@@H](C#N)C4)c3)n2)on1]

A solution of (1r,3r)-3-(4-(6-chloropyrazolo[1,5-a]pyrazin-4-yl)-1H-pyrazol-1-yl)-3-(cyanomethyl)cyclobutane-1-carbonitrile (Preparation 75, 110 mg, 0.33 mmol) and ethyl 5-(tributylstannyl)isoxazole-3-carboxylate (Preparation 76, 140 mg, 0.33 mmol) in 1,4-dioxane (3 mL) was purged with argon for about 5 min, followed by the addition of XPhos Pd G2 (51.2 mg, 0.065 mmol). The mixture was heated at about 100° C. for about 5 hrs. The mixture was concentrated and the residue was purified by chromatography to afford the title compound as a light yellow solid (66 mg, 45%).

$^1$H NMR (400 MHz, DMSO-d$_6$) δ: 9.44 (s, 1H), 9.02 (s, 1H), 8.60 (s, 1H), 8.42 (d, 1H), 7.65 (d, 1H), 7.62 (s, 1H), 4.44 (q, 2H), 3.54-3.63 (m, 1H), 3.53 (s, 2H), 3.26-3.36 (m, 2H), 2.90-2.98 (m, 2H), 1.37 (t, 3H).

LCMS m/z=443.3 [MH]$^+$

Example 29

5-(4-(1-((1r,3r)-3-Cyano-1-(cyanomethyl)cyclobutyl)-1H-pyrazol-4-yl)pyrazolo[1,5-a]pyrazin-6-yl)isoxazole-3-carboxamide

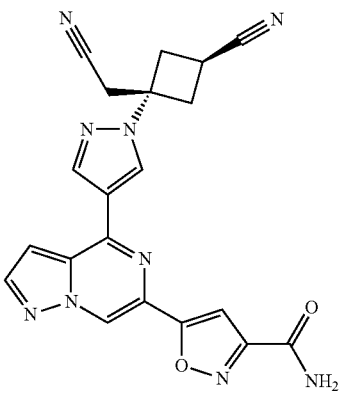 [SMILES: N#CC[C@]1(n2cc(-c3nc(-c4cc(C(N)=O)no4)cn4nccc34)cn2)C[C@H](C#N)C1]

A solution of ethyl 5-(4-(1-((1r,3r)-3-cyano-1-(cyanomethyl)cyclobutyl)-1H-pyrazol-4-yl)pyrazolo[1,5-a]pyrazin-6-yl)isoxazole-3-carboxylate (Preparation 77, 54 mg, 0.12 mmol) in methanol (3 mL) was treated with a 7 M solution of ammonia gas in methanol (2 mL, 14 mmol). The reaction vessel was tightly sealed and the mixture was heated at about 95° C. for about 18 hrs. After cooling, the precipitate was filtered, washed with EtOAc followed by Et$_2$O, and dried to afford the title compound as a white solid (45 mg, 89%).

$^1$H NMR (400 MHz, DMSO-d$_6$) δ: 9.36 (s, 1H), 9.01 (s, 1H), 8.58 (s, 1H), 8.41 (d, 1H), 8.21 (br. s, 1H), 7.91 (br. s, 1H), 7.64 (d, 1H), 7.50 (s, 1H), 3.55-3.62 (m, 1H), 3.53 (s, 2H), 3.26-3.35 (m, 2H), 2.90-2.98 (m, 2H).

LCMS m/z=414.3 [MH]$^+$

Preparation 78

2-((1r,3s)-1-(4-(6-(5-(DiBoc)-amino-1-(tetrahydro-2H-pyran-2-yl)-pyrazol-3-yl)pyrazolo[1,5-a]pyrazin-4-yl)-1H-pyrazol-1-yl)-3-methoxycyclobutyl)acetonitrile

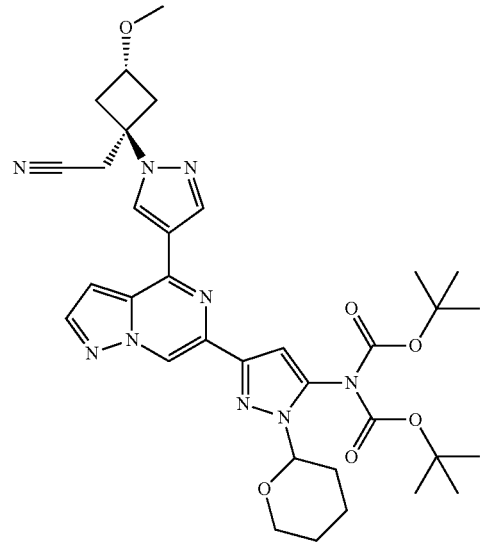 [SMILES: CO[C@H]1C[C@](CC#N)(n2cc(-c3nc(-c4cc(N(C(=O)OC(C)(C)C)C(=O)OC(C)(C)C)n(C5CCCCO5)n4)cn4nccc34)cn2)C1]

A mixture of 3-bromo-1-(tetrahydro-2H-pyran-2-yl)-5-(diBoc)-amino-1H-pyrazole (Preparation 43, 233 mg, 0.52 mmol), KOAc (162 mg, 1.57 mmol), and bis(pinacolato)diboron (199 mg, 0.78 mmol) in 1,4-dioxane (4 mL) was purged with argon for about 5 min, after which XPhos Pd G2 (82.1 mg, 0.10 mmol) was added. The mixture was heated at about 65° C. for about 3.5 hrs.

After cooling to about 20° C., 2-((1r,3s)-1-(4-(6-chloropyrazolo[1,5-a]pyrazin-4-yl)-1H-pyrazol-1-yl)-3-methoxy-cyclo-butyl)aceto-nitrile (Preparation 39, 125 mg, 0.36 mmol), 2 M aq. K$_3$PO$_4$ (0.783 mL) and XPhos Pd G2 (82.1 mg, 0.10 mmol) were added. The mixture was again purged with argon, then heated at about 80° C. for about 1 hrs. After cooling, the mixture was diluted with EtOAc and the phases were separated. The aqueous phase was extracted twice with EtOAc and the combined EtOAc extracts were concentrated. The residue was purified by chromatography to afford the title compound as a clear oil (220 mg, 62%).

$^1$H NMR (400 MHz, CDCl$_3$) δ: 9.08 (s, 1H), 8.39 (s, 1H), 8.33 (s, 1H), 8.09 (d, 1H), 6.97 (d, 1H), 6.90 (s, 1H), 5.26 (dd, 1H), 4.03-4.11 (m, 2H), 3.64 (t, 1H), 3.34 (s, 3H), 3.25 (s, 2H), 3.11-3.19 (m, 2H), 2.55-2.63 (m, 2H), 2.21 (m, 1H), 1.93 (dd, 1H), 1.59-1.84 (m, 4H), 1.45 (s, 18H).

LCMS m/z=674.5 [MH]$^+$

Example 30

2-((1r,3s)-1-(4-(6-(3-Amino-1H-pyrazol-5-yl)pyrazolo[1,5-a]pyrazin-4-yl)-1H-pyrazol-1-yl)-3-methoxycyclobutyl)acetonitrile

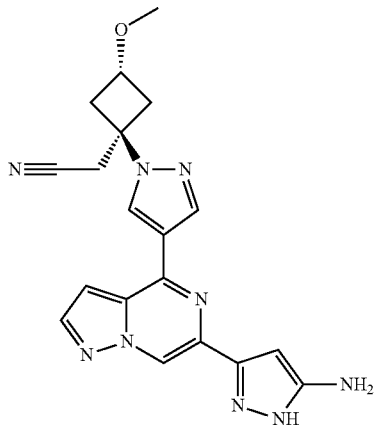 [SMILES: CO[C@H]1C[C@](CC#N)(n2cc(-c3nc(-c4cc(N)[nH]n4)cn4nccc34)cn2)C1]

TFA (3 mL) was added to a solution of 2-((1r,3s)-1-(4-(6-(5-(diBoc)-amino-1-(tetrahydro-2H-pyran-2-yl)-pyrazol-3-yl)pyrazolo[1,5-a]pyrazin-4-yl)-1H-pyrazol-1-yl)-3-methoxycyclobutyl)acetonitrile (Preparation 78, 220 mg, 0.33 mmol) in DCM (2 mL) at about 20° C. After about 1 hrs at this temperature, the mixture was concentrated and the residue was dissolved in DCM and saturated aq. NaHCO$_3$, ensuring that the pH was basic. The DCM was separated and the aqueous phase was extracted twice with DCM. The combined DCM extracts were dried (Na$_2$SO$_4$), concentrated, and the residue was purified by chromatography followed by HPLC to afford the title compound as a white solid (17 mg, 13%).

$^1$H NMR (400 MHz, CD$_3$OD) δ: 8.89 (s, 1H), 8.84 (s, 1H), 8.54 (s, 1H), 8.17-8.18 (m, 1H), 7.34 (s, 1H), 6.22 (s, 1H), 4.09-4.12 (m, 1H), 3.39 (s, 3H), 3.22-3.27 (m, 2H), 2.56-2.60 (m, 2H).

LCMS m/z=390.3 [MH]$^+$

Preparation 79

(4-Bromo-1-methyl-1H-pyrazol-3-yl)methanol

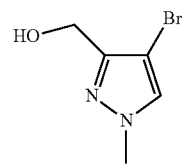

Sodium borohydride (3.4 g, 90 mmol) was added to a solution of ethyl 4-bromo-1-methyl-1H-pyrazole-3-carboxylate (4.2 g, 18 mmol) in anhydrous EtOH (150 mL) at about 5° C. The mixture was then heated at about 50° C. for about 16 h, after which EtOAc (100 mL) and water (100 mL) were added. The EtOAc was separated, dried (Na$_2$SO$_4$), and concentrated. The residue was purified by chromatography to afford the title compound as a white solid (1.05 g, 31%).

$^1$H NMR (400 MHz, DMSO-d$_6$) δ: 7.84 (s, 1H), 5.01 (td, 1H), 4.33 (d, 2H), 3.77 (s, 3H).

LCMS m/z=192.7 [MH]$^+$ ($^{81}$Br isotope)

Preparation 80

4-Bromo-1-methyl-3-(((tetrahydro-2H-pyran-2-yl)oxy)methyl)-1H-pyrazole

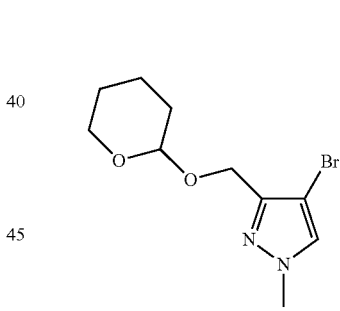

To a solution of (4-bromo-1-methyl-1H-pyrazol-3-yl)methanol (Preparation 79, 1.00 mg, 5.23 mmol) in THF (30 mL) were added DHP (1.32 g, 15.7 mmol) and PTSA (19.9 mg, 0.10 mmol). The solution was heated at about 50° C. for about 16 hrs. The mixture was concentrated and the residue was purified by chromatography to afford the title compound as a colorless oil (1.02 g, 71%).

$^1$H NMR (400 MHz, CDCl$_3$) δ: 7.36 (s, 1H), 4.80 (t, 1H), 4.73 (d, 1H), 4.45 (d, 1H), 3.95-4.03 (m, 1H), 3.87 (s, 3H), 3.53-3.64 (m, 1H), 1.78-1.93 (m, 1H), 1.60-1.77 (m, 3H), 1.45-1.60 (m, 2H).

LCMS m/z=174.6 [MH-THP]$^+$

Preparation 81

1-Methyl-3-(((tetrahydro-2H-pyran-2-yl)oxy)methyl)-4-(4,4,5,5-tetramethyl-1,3,2-dioxaborolan-2-yl)-1H-pyrazole

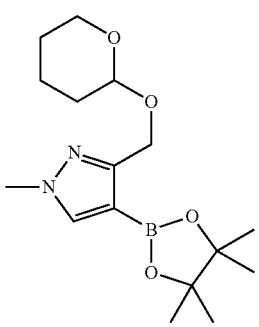

To a solution of 4-bromo-1-methyl-3-(((tetrahydro-2H-pyran-2-yl)oxy)methyl)-1H-pyrazole (Preparation 80, 330 mg, 1.20 mmol) in DMF (12 mL) were added bis(pinacolato)diboron (457 mg, 1.8 mmol) and KOAc (353 mg, 3.6 mmol). The mixture was purged with nitrogen for about 2 min, after which Pd(dppf)Cl$_2$ (87.8 mg, 0.12 mmol) was added. The mixture was heated at about 90° C. for about 16 hrs. The cooled mixture was filtered through a pad of Celite® and the filter was washed with methanol (15 mL). The filtrate was concentrated to afford the impure title compound as dark gum (1.17 g), which was used in Example 31 next step without further purification.

$^1$H NMR (400 MHz, CDCl$_3$) δ: 7.61 (s, 1H), 4.75-4.77 (m, 1H), 4.50-4.57 (m, 2H), 4.03-4.10 (m, 1H), 3.91-3.98 (m, 1H), 3.89 (s, 3H), 1.81-1.90 (m, 1H), 1.61-1.76 (m, 3H), 1.49-1.56 (m, 2H), 1.30 (s, 12H).

LCMS m/z=239.1 [MH-THP]$^+$

Example 31

2-((1r,3s)-1-(4-(6-(3-(Hydroxymethyl)-1-methyl-1H-pyrazol-4-yl)pyrazolo[1,5-a]pyrazin-4-yl)-1H-pyrazol-1-yl)-3-methoxycyclobutyl)acetonitrile

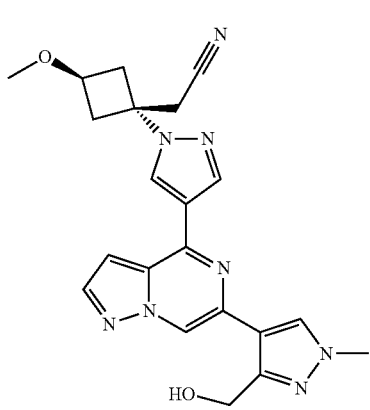

Part 1

A mixture of 2-((1r,3s)-1-(4-(6-chloropyrazolo[1,5-a]pyrazin-4-yl)-1H-pyrazol-1-yl)-3-methoxy-cyclobutyl)acetonitrile (Preparation 39, 80 mg, 0.23 mmol), 1-methyl-3-(((tetrahydro-2H-pyran-2-yl)oxy)methyl)-4-(4,4,5,5-tetramethyl-1,3,2-dioxaborolan-2-yl)-1H-pyrazole (Preparation 81, 376 mg, 1.17 mmol), and 2 M aq. K$_3$PO$_4$ (0.35 mL) in 1,4-dioxane (2.5 mL) was treated with XPhos Pd G2 (18.4 mg, 0.023 mmol) and the mixture was purged with nitrogen. The mixture was heated at about 60° C. for about 20 hrs. The mixture was concentrated and the residue was purified by chromatography to afford the title compound as a yellow gum. This sample was combined with the product from an equivalent reaction conducted using 2-((1r,3s)-1-(4-(6-chloropyrazolo[1,5-a]pyrazin-4-yl)-1H-pyrazol-1-yl)-3-methoxycyclobutyl)acetonitrile (Preparation 39, 120 mg, 0.35 mmol), 1-methyl-3-(((tetrahydro-2H-pyran-2-yl)oxy)methyl)-4-(4,4,5,5-tetramethyl-1,3,2-dioxaborolan-2-yl)-1H-pyrazole (Preparation 81, 564 mg, 1.75 mmol), 2 M aq. K$_3$PO$_4$ (0.525 mL), and XPhos Pd G2 (13.8 mg, 0.023 mmol) in 1,4-dioxane (3.5 mL) to afford 2-((1r,3s)-3-methoxy-1-(4-(6-(1-methyl-3-(((tetrahydro-2H-pyran-2-yl)oxy)methyl)-1H-pyrazol-4-yl)pyrazolo[1,5-a]pyrazin-4-yl)-1H-pyrazol-1-yl)cyclobutyl)acetonitrile in a total yield of 150 mg (51%), which was used in Part 2 without further purification.

Part 2

TFA (1 mL) was added to an ice-cooled solution of 24(1r,3s)-3-methoxy-1-(4-(6-(1-methyl-3-(((tetrahydro-2H-pyran-2-yl)oxy)methyl)-1H-pyrazol-4-yl)pyrazolo[1,5-a]pyrazin-4-yl)-1H-pyrazol-1-yl)cyclobutyl)acetonitrile (Part 1, 150 mg, 0.30 mmol) in DCM (3 mL). The mixture was stirred with cooling in ice for about 2 hrs, then concentrated. The residue was purified by HPLC to afford the title compound as a light yellow solid (53 mg, 38%).

$^1$H NMR (400 MHz, CD$_3$OD) δ: 8.87 (s, 1H), 8.69 (s, 1H), 8.40 (s, 1H), 8.21 (s, 1H), 8.13 (d, 1H), 7.28 (d, 1H), 4.83 (s, 2H), 4.05-4.14 (m, 1H), 3.96 (s, 3H), 3.37 (s, 2H), 3.34 (s, 3H), 3.18-3.27 (m, 2H), 2.53-2.62 (m, 2H).

LCMS m/z=419.1 [MH]$^+$

Preparation 82

2-((1s,3r)-1-(4-(6-Chloropyrazolo[1,5-a]pyrazin-4-yl)-1H-pyrazol-1-yl)-3-methoxycyclobutyl)acetonitrile

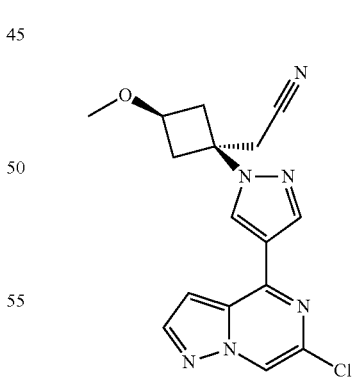

Part 1

To a solution of 2-((1s,3r)-1-(4-bromo-1H-pyrazol-1-yl)-3-methoxycyclobutyl)acetonitrile (Preparation 37, cis isomer, 400 mg, 1.48 mmol) in toluene (9 mL) were added bis(pinacolato)diboron (564 mg, 2.22 mmol) and KOAc (436 mg, 4.44 mmol). The mixture was purged with nitrogen for about 3 min, after which Pd(dppf)Cl$_2$ (108 mg, 0.15 mmol) was added. The mixture was again purged with nitrogen for about 3 min, then heated at about 110° C. for about 16 hrs. The cooled mixture was concentrated and the residue was purified by chromatography to afford impure 2-((1s,3r)-3-m ethoxy-1-(4-(4,4,5,5-tetramethyl-1,3,2-dioxaborolan-2-yl)-1H-pyrazol-1-yl)cyclobutyl)acetonitrile as light-yellow oil (500 mg), which was used in Part 2.

Part 2

A solution of 2-((1s,3r)-3-methoxy-1-(4-(4,4,5,5-tetramethyl-1,3,2-dioxaborolan-2-yl)-1H-pyrazol-1-yl)cyclobutyl) acetonitrile (Part 1, 470 mg, 1.48 mmol) and 4,6-dichloropyrazolo[1,5-a]pyrazine (Preparation 4, 279 mg, 1.48 mmol), and 2 M aq. $K_2CO_3$ (2.22 mL) in 1,4-dioxane (10 mL) was purged with nitrogen for about 2 min, after which $Pd(dppf)Cl_2$ (108 mg, 0.15 mmol) was added. The mixture was again purged with nitrogen for about 3 min, then heated at about 90° C. for about 16 hrs. The cooled mixture was concentrated and the residue was purified by chromatography to afford the title compound as a yellow solid (130 mg, 26%).

$^1$H NMR (400 MHz, $CDCl_3$) δ: 8.40 (s, 1H), 8.35 (s, 1H), 8.27 (s, 1H), 8.08 (d, 1H), 7.00 (s, 1H), 4.05 (quin, 1H), 3.30 (s, 3H), 3.10 (s, 2H), 3.00 (m, 2H), 2.75 (m, 2H).

LCMS m/z=343.2 $[MH]^+$ ($Cl^{35}$ isotope)

Preparation 83

Ethyl 5-(4-(1-((1s,3r)-1-(cyanomethyl)-3-methoxycyclobutyl)-1H-pyrazol-4-yl)pyrazolo[1,5-a]pyrazin-6-yl)-1H-pyrazole-3-carboxylate

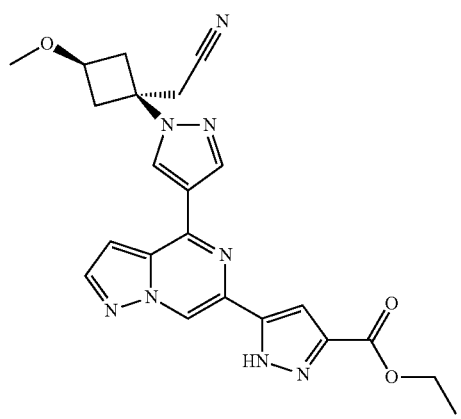 [SMILES: CCOC(=O)c1cc(-c2cn3nccc3c(-c3cnn([C@]4(CC#N)C[C@H](OC)C4)c3)n2)[nH]n1]

A solution of 2-((1s,3r)-1-(4-(6-chloropyrazolo[1,5-a]pyrazin-4-yl)-1H-pyrazol-1-yl)-3-methoxycyclobutyl)acetonitrile (Preparation 82, 120 mg, 0.35 mmol) and ethyl 5-(tributylstannyl)-1H-pyrazole-3-carboxylate (Preparation 31, 150 mg, 0.35 mmol) in 1,4-dioxane (5 mL) was treated with XPhos Pd G2 (13.8 mg, 0.017 mmol) and the mixture was purged with nitrogen for about 2 min. The mixture was heated at about 110° C. for about 2 hrs. The cooled mixture was concentrated and the residue was purified by chromatography to afford the title compound as a yellow solid (180 mg).

$^1$H NMR (400 MHz, $CDCl_3$) δ: 9.05 (br. s., 1H), 8.39 (s, 1H), 8.32 (s, 1H), 8.14 (s, 1H), 7.65 (s, 1H), 7.02 (s, 1H), 6.88 (s, 1H), 4.44-4.50 (m, 2H), 4.08 (t, 1H), 3.80 (s, 3H), 3.13 (s, 2H), 3.00-3.08 (m, 2H), 2.75-2.83 (m, 2H), 1.46 (t, 3H).

LCMS m/z=447.1 $[MH]^+$

Example 32

5-(4-(14(1s,3r)-1-(Cyanomethyl)-3-methoxycyclobutyl)-1H-pyrazol-4-yl)pyrazolo[1,5-a]pyrazin-6-yl)-1H-pyrazole-3-carboxamide

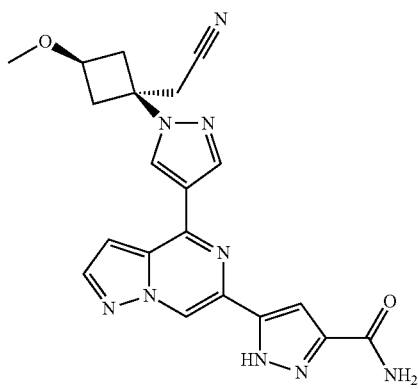 [SMILES: CO[C@H]1C[C@@](CC#N)(n2cc(-c3nc(-c4cc(C(N)=O)n[nH]4)cn4nccc34)cn2)C1]

A solution of ethyl 5-(4-(1-((1s,3r)-1-(cyanomethyl)-3-methoxycyclobutyl)-1H-pyrazol-4-yl)pyrazolo[1,5-a] pyrazin-6-yl)-1H-pyrazole-3-carboxylate (Preparation 83, 100 mg, 0.22 mmol) in MeOH (2 mL) was treated with a 4 M solution of ammonia gas in methanol (1 mL). The reaction vessel was tightly sealed and the mixture was heated at about 60° C. for about 16 hrs. The mixture was concentrated and the residue was purified by HPLC to afford the title compound (23 mg, 25%).

$^1$H NMR (400 MHz, DMSO-$d_6$) δ: 13.79 (br. s., 1H), 9.31 (br. s., 1H), 9.00 (br. s., 1H), 8.67 (br. s., 1H), 8.28 (d, 1H), 7.56 (br. s., 2H), 7.39 (br. s., 1H), 7.25-7.35 (m, 1H), 4.08 (quin, 1H), 3.44 (s, 2H), 3.21 (s, 3H), 2.79-2.90 (m, 2H), 2.63-2.73 (m, 3H).

LCMS m/z=440.1 $[MNa]^+$

Preparation 84

2-(Tetrahydro-2H-pyran-2-yl)-2H-1,2,3-triazole

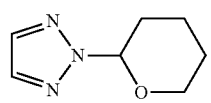

To a mixture of 1H-1,2,3-triazole (15 g, 220 mmol) in DCM (724 mL) were added DHP (21.9 g, 261 mmol) and PTSA (0.374 g, 2.17 mmol). The mixture was kept at about 25° C. for about 18 hrs, after which NaOH (96 mg, 2.39 mmol) was added. The mixture was stirred at about 25° C. for about 1 hrs then filtered. The filtrate was concentrated and the residue was purified by chromatography to afford the title compound as a colorless oil (18 g, 54%).

$^1$H NMR (400 MHz, $CDCl_3$) δ: 7.68 (s, 2H), 5.74 (dd, 1H), 4.00-4.08 (m, 1H), 3.69-3.81 (m, 1H), 2.36-2.51 (m, 1H), 2.02-2.20 (m, 2H), 1.61-1.81 (m, 3H).

Preparation 85

2-(Tetrahydro-2H-pyran-2-yl)-4-(4,4,5,5-tetramethyl-1,3,2-dioxaborolan-2-yl)-2H-1,2,3-triazole

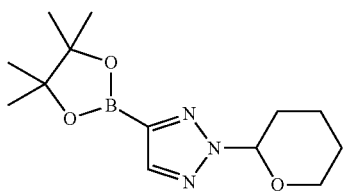 [SMILES: CC1(C)OB(c2cnn(C3CCCCO3)n2)OC1(C)C]

To a solution of 4,4,5,5-tetramethyl-1,3,2-dioxaborolane (24 g, 129 mmol) in pentane (200 mL) were added 4,4'-di-tert-butyl-2,2'-bipyridine (0.315 g, 1.18 mmol) and (1,5-cyclooctadiene)(methoxy)iridium(I) dimer (234 mg, 0.35 mmol). The solution rapidly became a red color and gas evolution was observed. After about 15 min, 2-(tetrahydro-2H-pyran-2-yl)-2H-1,2,3-triazole (Preparation 84, 18 g, 117 mmol) was added. The mixture was stirred at about 25° C. for about 6 h. The mixture was concentrated and the residue was purified by chromatography to afford the title compound as a colorless solid (26 g, 79%).

$^1$H NMR (400 MHz, CDCl$_3$) δ: 7.99 (s, 1H), 5.81 (dd, 1H), 4.07 (d, 1H), 3.67-3.78 (m, 1H), 2.41-2.55 (m, 1H), 2.02-2.16 (m, 2H), 1.60-1.80 (m, 3H), 1.37 (s, 12H).

LCMS m/z=113.9 [MH-C$_2$H$_2$N]$^+$

Preparation 86

(1r,3r)-3-(Cyanomethyl)-3-(4-(6-(2-(tetrahydro-2H-pyran-2-yl)-2H-1,2,3-triazol-4-yl)pyrazolo[1,5-a]pyrazin-4-yl)-1H-pyrazol-1-yl)cyclobutane-1-carbonitrile

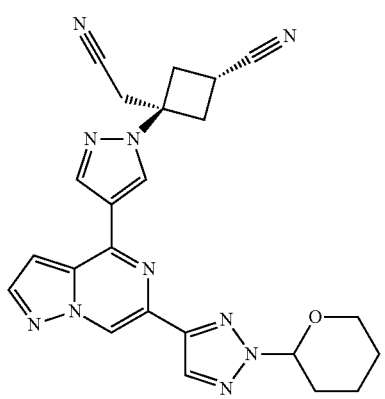 [SMILES: N#CC[C@]1(n2cc(-c3nc(-c4cnn(C5CCCCO5)n4)cn4nccc34)cn2)C[C@H](C#N)C1]

A mixture of (1r,3r)-3-(4-(6-chloropyrazolo[1,5-a]pyrazin-4-yl)-1H-pyrazol-1-yl)-3-(cyanomethyl)cyclobutane-1-carbonitrile (Preparation 75, 300 mg, 0.89 mmol), 2-(tetrahydro-2H-pyran-2-yl)-4-(4,4,5,5-tetramethyl-1,3,2-dioxaborolan-2-yl)-2H-1,2,3-triazole (Preparation 85, 248 mg, 0.89 mmol), and 2 M aq. K$_3$PO$_4$ (1 mL) in 1,4-dioxane (4 mL) was purged with argon for about 5 min, after which XPhos Pd G2 (140 mg, 0.18 mmol) was added. The mixture was heated at about 50° C. for about 1 hrs, then cooled and diluted with EtOAc. The phases were separated and the aqueous phase was extracted twice with DCM. The combined EtOAc and DCM extracts were dried (Na$_2$SO$_4$) and concentrated. The residue was purified by chromatography to afford the title compound as a clear gum (384 mg, 95%).

$^1$H NMR (400 MHz, CDCl$_3$) δ: 9.02 (s, 1H), 8.41 (s, 1H), 8.35 (s, 1H), 8.28 (s, 1H), 8.13 (d, 1H), 7.00 (d, 1H), 5.81 (dd, 1H), 4.06-4.12 (m, 1H), 3.77-3.87 (m, 1H), 3.35-3.47 (m, 3H), 3.30 (s, 2H), 2.95-3.04 (m, 2H), 2.45-2.59 (m, 1H), 2.12-2.24 (m, 2H), 1.69-1.87 (m, 3H)

LCMS m/z=455.3 [MH]$^+$

Preparation 87

(1r,3r)-3-(4-(6-(2H-1,2,3-Triazol-4-yl)pyrazolo[1,5-a]pyrazin-4-yl)-1H-pyrazol-1-yl)-3-(cyanomethyl)cyclobutane-1-carbonitrile

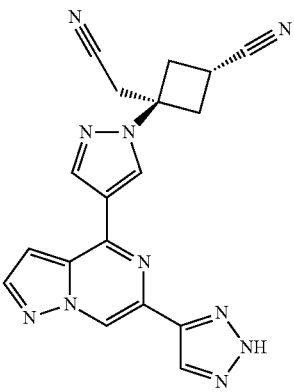 [SMILES: N#CC[C@]1(n2cc(-c3nc(-c4cn[nH]n4)cn4nccc34)cn2)C[C@H](C#N)C1]

A suspension of (1r,3r)-3-(cyanomethyl)-3-(4-(6-(2-(tetrahydro-2H-pyran-2-yl)-2H-1,2,3-triazol-4-yl)pyrazolo[1,5-a]pyrazin-4-yl)-1H-pyrazol-1-yl)cyclobutane-1-carbonitrile (Preparation 86, 384 mg, 0.84 mmol) in MeOH (5 mL) was treated with PTSA (16.1 mg, 0.084 mmol). The mixture was heated at about 60° C. for about 3.5 h. The solids dissolved to form a homogeneous solution, after which a white solid precipitated. Heating was continued for about 1 hrs further. The mixture was cooled to about 0° C. for about 30 min and filtered. The precipitate was washed with MeOH and dried under vacuum to afford the title compound as a white solid (204 mg, 65%).

$^1$H NMR (400 MHz, DMSO-d$_6$) δ: 9.05 (s, 1H), 8.97 (s, 1H), 8.72 (br. s., 1H), 8.57 (s, 1H), 8.46 (s, 1H), 8.30 (s, 1H), 7.56 (s, 1H), 3.55-3.62 (m, 1H), 3.53 (s, 2H), 3.22-3.30 (m, 2H), 2.89-3.00 (m, 2H).

LCMS m/z=371.3 [MH]$^+$

Example 33

(1r,3r)-3-(Cyanomethyl)-3-(4-(6-(1-methyl-1H-1,2,3-triazol-4-yl)pyrazolo[1,5-a]pyrazin-4-yl)-1H-pyrazol-1-yl)cyclobutane-1-carbonitrile

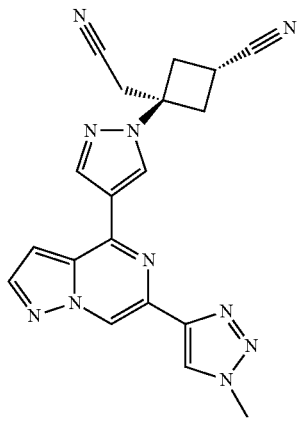 [SMILES: Cn1cc(-c2cn3nccc3c(-c3cnn([C@]4(CC#N)C[C@@H](C#N)C4)c3)n2)nn1]

To a mixture of (1r,3r)-3-(4-(6-(2H-1,2,3-triazol-4-yl)pyrazolo[1,5-a]pyrazin-4-yl)-1H-pyrazol-1-yl)-3-(cyanomethyl)cyclobutane-1-carbonitrile (Preparation 87, 100 mg, 0.27 mmol) and K$_2$CO$_3$ (75 mg, 0.54 mmol) in DMF (1 mL) was added iodomethane (0.034 mL, 0.540 mmol). The mixture was stirred for about 2 hrs at about 25° C. The mixture was filtered and the filter cake was washed twice with DCM. The filtrate was concentrated and the residue was purified by chromatography followed by HPLC to afford the title compound as a white solid (40 mg, 39%).

$^1$H NMR (400 MHz, CDCl$_3$) δ: 9.19 (s, 1H), 8.51 (s, 1H), 8.33 (s, 1H), 8.30 (s, 1H), 8.15 (d, 1H), 7.03 (s, 1H), 4.22 (s, 3H), 3.35-3.46 (m, 3H), 3.30 (s, 2H), 2.99 (d, 2H).

LCMS m/z=385.4 [MH]$^+$

Example 34

(1s,3s)-3-(Cyanomethyl)-1-methyl-3-(4-(6-(1-methyl-1H-pyrazol-4-yl)pyrazolo[1,5-a]pyrazin-4-yl)-1H-pyrazol-1-yl)cyclobutane-1-carbonitrile

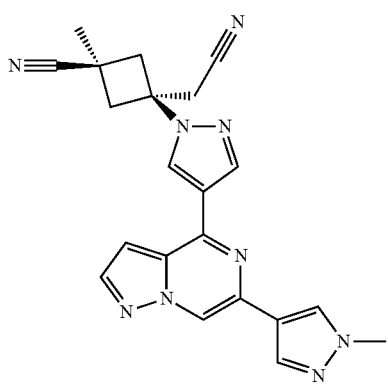 [SMILES: Cn1cc(-c2cn3nccc3c(-c3cnn([C@]4(CC#N)C[C@](C)(C#N)C4)c3)n2)cn1]

and

Example 35

(1r,3r)-3-(Cyanomethyl)-1-methyl-3-(4-(6-(1-methyl-1H-pyrazol-4-yl)pyrazolo[1,5-a]pyrazin-4-yl)-1H-pyrazol-1-yl)cyclobutane-1-carbonitrile

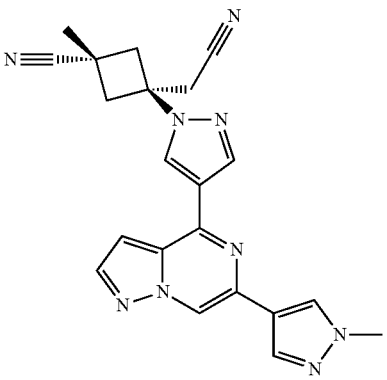 [SMILES: Cn1cc(-c2cn3nccc3c(-c3cnn([C@]4(CC#N)C[C@@](C)(C#N)C4)c3)n2)cn1]

DBU (327 mg, 2.15 mmol) was added to a solution of 6-(1-methyl-1H-pyrazol-4-yl)-4-(1H-pyrazol-4-yl)pyrazolo[1,5-a]pyrazine (Preparation 53, 190 mg, 0.72 mmol) and 3-(cyanomethylene)-1-methylcyclobutane-1-carbonitrile (Preparation 89, 142 mg, 1.07 mmol) in MeCN (15 mL) and the mixture was stirred at about 50° C. for about 4 hrs. The mixture was concentrated and the residue was purified by chromatography to afford a residue which was further purified by TLC to afford a mixture of the two title compounds (200 mg, 70%) as a brown solid. The mixture of isomers was separated by HPLC to afford (1r,3r)-3-(cyanomethyl)-1-methyl-3-(4-(6-(1-methyl-1H-pyrazol-4-yl)pyrazolo[1,5-a]pyrazin-4-yl)-1H-pyrazol-1-yl)cyclobutane-1-carbonitrile as a light pink solid (trans isomer, 24 mg 8%)

$^1$H NMR (400 MHz, CD$_3$CN) δ: 8.36 (s, 1H), 8.28 (s, 1H), 8.26-8.31 (m, 1H), 8.14 (s, 1H), 7.86 (s, 1H), 7.79 (d, 1H), 7.73 (s, 1H), 6.87 (d, 1H), 3.66 (s, 3H), 3.10 (s, 2H), 2.80-2.92 (m, 4H), 1.25 (s, 3H).

LCMS m/z=398.0 [MH]$^+$ and 420.0 [MNa]$^+$ and (1s, 3s)-3-(cyanomethyl)-1-methyl-3-(4-(6-(1-methyl-1H-pyrazol-4-yl)pyrazolo[1,5-a]pyrazin-4-yl)-1H-pyrazol-1-yl)cyclobutane-1-carbonitrile (cis isomer, 24 mg, 8%).

$^1$H NMR (400 MHz, CD$_3$CN) δ: 8.68 (s, 1H), 8.63 (s, 1H), 8.44 (s, 1H), 8.14 (s, 1H), 8.05 (d, 1H), 8.00 (s, 1H), 7.15 (d, 1H), 3.92 (s, 3H), 3.47-3.55 (m, 2H), 3.19 (s, 2H), 2.74-2.82 (m, 2H), 1.63 (s, 3H).

LCMS m/z=398.0 [MH]$^+$ and 419.9 [MNa]$^+$

Preparation 88

1-Methyl-3-oxocyclobutane-1-carbonitrile

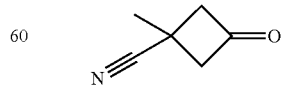

Part 1

To a solution of diisopropylamine (1.30 g, 12.9 mmol) in THF (30 mL) was added 2.5 M n-BuLi (5.15 mL) at about 0° C. The solution was stirred for about 30 min at about 0°

C. before being cooled to about −78° C. 3-Methylenecyclobutane-1-carbonitrile (1.00 g, 10.74 mmol) was added and the solution was stirred for about 1 h at about −78° C. Iodomethane (1.98 g, 14.0 mmol) was added to the solution at about −78° C., then the mixture was allowed to warm to about 20° C. and was kept at this temperature for about 0.5 hrs. Saturated aq. NH₄Cl (30 mL) was added and the mixture was extracted with EtOAc (3×30 mL). The combined EtOAc extracts were concentrated to afford 1-methyl-3-methylenecyclobutane-1-carbonitrile as a pale yellow oil (1.1 g, 96%).

¹H NMR (400 MHz, CDCl₃) δ: 4.90-4.98 (m, 2H), 3.23-3.35 (m, 2H), 2.64-2.75 (m, 2H), 1.55 (s, 3H).

Part 2

To a mixture of 1-methyl-3-methylenecyclobutane-1-carbonitrile (1.10 g, 10.3 mmol) and RuCl₃ hydrate (50.9 mg, 0.23 mmol) in a mixture of DCM (20 mL), MeCN (20 mL) and water (40 mL) was added NaIO₄ (8.78 g, 41.1 mmol) in small portions at about 5° C. The mixture was then stirred at about 25° C. for about 17 hrs. The aqueous phase was separated and extracted with DCM (2×50 mL). The DCM extracts were combined with the DCM-MeCN phase and dried (Na₂SO₄), then filtered through about 10 g of silica gel. The silica gel was washed with DCM (50 mL). The filtrate was concentrated to afford the title compound as a brown oil (0.80 g, 71%).

¹H NMR (400 MHz, CDCl₃) δ: 3.71 (m, 2H), 3.14 (m, 2H), 1.71 (s, 3H).

Preparation 89

3-(Cyanomethylene)-1-methylcyclobutane-1-carbonitrile

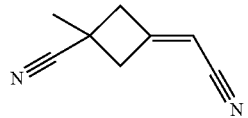

A mixture of 1-methyl-3-oxocyclobutane-1-carbonitrile (Preparation 88, 0.80 g, 7.0 mmol), (EtO)₂P(O)CH₂CN (1.43 g, 8.06 mmol), LiBr (0.955 g, 11.0 mmol) and TEA (1.48 g, 14.7 mmol) in THF (20 mL) was stirred at about 25° C. for about 16 hrs. Water (30 mL) was added and the mixture was extracted with EtOAc (3×50 mL). The combined EtOAc extracts were dried (Na₂SO₄) and concentrated. The residue was purified by chromatography to afford the title compound as a colorless oil (0.65 g, 70%).

¹H NMR (400 MHz, CDCl₃) δ: 5.34 (m, 1H), 3.47 (m, 2H), 2.98 (m, 2H), 1.60 (s, 3H). GCMS m/z=131 [M−H]⁺

Preparation 90

2-(3-Methoxycyclobutylidene)acetonitrile

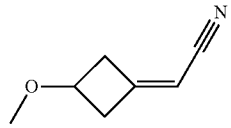

Part 1

Twelve Identical reactions were carried out in parallel as follows:

For each reaction, a 100 mL sealed tube was charged with methoxyethene (37 g, 637 mmol), DIPEA (9.88 g, 76.4 mmol), and acetyl chloride (5 g, 60 mmol) at about −30° C. The mixture was then heated at about 70° C. for about 5 hrs. The twelve reactions were combined and washed with 1 M aq. HCl (2×100 mL), saturated aq. NaHCO₃ (2×100 mL), dried (Na₂SO₄) and concentrated to afford a crude specimen of 3-methoxycyclobutan-1-one as a black oil (27 g, 37%). This material was about 50% pure as judged by ¹H NMR and was used without further purification in Part 2.

Part 2

Two identical reactions were carried out in parallel.

To a mixture of LiBr (13.4 g, 154 mmol) and TEA (39 mL, 280 mmol) in THF (200 mL) was added (EtO)₂P(O)CH₂CN (26 g, 147 mmol) at about 0° C. Stirring was continued at about 25° C. for about 2 hrs. To this mixture was added a solution of the crude 3-methoxycyclobutan-1-one prepared in Part 1 (13 g, about 70 mmol) in THF (40 mL) at about 0° C. The mixture was then stirred at about 25° C. for about 16 hrs. The two reaction mixtures were combined and concentrated. The residue was purified by chromatography to afford the title compound as a light yellow oil (9.2 g, 56%).

¹H NMR (400 MHz, CDCl₃) δ: 5.25 (m, 1H), 4.05 (m, 1H), 3.30 (s, 3H), 3.25 (m, 1H), 3.10 (m, 1H), 2.85 (m, 2H). LCMS m/z=124.08 [MH]⁺

Preparation 91

(1r,3r)-3-(Cyanomethyl)-3-(4-(4,4,5,5-tetramethyl-1,3,2-dioxaborolan-2-yl)-1H-pyrazol-1-yl)cyclobutane-1-carbonitrile (trans isomer)

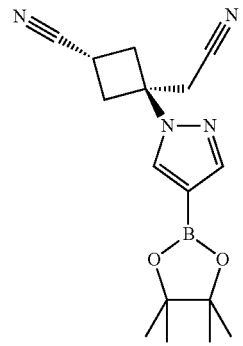 [SMILES: CC1(C)OB(c2cnn([C@]3(CC#N)C[C@@H](C#N)C3)c2)OC1(C)C]

and (1s,3S)-3-(cyanomethyl)-3-(4-(4,4,5,5-tetramethyl-1,3,2-dioxaborolan-2-yl)-1H-pyrazol-1-yl)cyclobutane-1-carbonitrile (cis isomer)

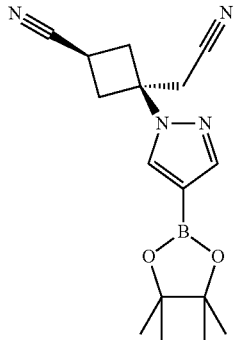 [SMILES: CC1(C)OB(c2cnn([C@]3(CC#N)C[C@H](C#N)C3)c2)OC1(C)C]

To a solution of 4-(4,4,5,5,-tetramethyl-1,3,2-dioxaborolan-2-yl)-1H-pyrazole (1.3 kg, 6.67 mol) in MeCN (43 L) were added 3-cyanomethylene)cyclobutane-1-carbonitrile (Preparation 27, 953 g, 8 mol) and DBU (3.06 kg, 20.1 mol) at about 20° C. Stirring was continued at about 20° C. for about 16 hrs. The mixture was poured into 1 M aq. KH₂PO4 (10 L) and extracted with EtOAc (5×5 L). The combined EtOAc extracts were concentrated and the residue was purified by chromatography to afford (1r,3r)-3-(cyanomethyl)-3-(4-(4,4,5,5-tetramethyl-1,3,2-dioxaborolan-2-yl)-1H-pyrazol-1-yl)cyclobutane-1-carbonitrile as a white solid (trans isomer, 610 g, 30%) melting point 137-140° C.

$^1$H NMR (400 MHz, CDCl$_3$) δ: 7.90 (s, 1H), 7.88 (s, 1H), 3.21-3.28 (m, 3H), 3.19 (s, 2H), 2.86-2.94 (m, 2H), 1.33 (s, 12H).

$^{13}$C NMR (101 MHz, CD$_3$OD) δ: 147.54, 136.49, 122.49, 117.11, 84.96, 61.93, 37.52, 30.47, 25.28, 25.18, 17.21.

LCMS m/z=313.1 [MH]$^+$ and (1s, 3s)-3-(cyanomethyl)-3-(4-(4,4,5,5-tetramethyl-1,3,2-dioxaborolan-2-yl)-1H-pyrazol-1-yl)cyclobutane-1-carbonitrile as an off-white solid (cis isomer, 250 g, 12%).

melting point 95-98° C.

$^1$H NMR (400 MHz, CDCl$_3$) δ: 7.86 (s, 2H), 3.24-3.31 (m, 1H), 3.13-3.21 (m, 2H), 3.07 (s, 2H), 2.96-3.04 (m, 2H), 1.34 (s, 12H).

$^{13}$C NMR (101 MHz, CD$_3$OD) δ: 147.43, 135.94, 121.94, 117.37, 84.98, 75.96, 60.10, 37.95, 28.42, 25.29, 16.16.

LCMS m/z=313.1 [MH]$^+$

Preparation 92

5-Methyl-1-(tetrahydro-2H-pyran-2-yl)-1H-pyrazole

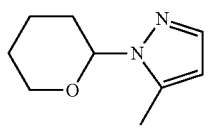

and

3-Methyl-1-(tetrahydro-2H-pyran-2-yl)-1H-pyrazole

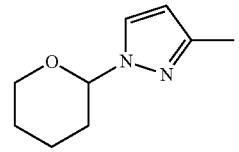

A mixture of 3-methylpyrazole (1.00 g, 12.18 mmol), DHP (1.54 g, 18.3 mmol) and TFA (0.007 mL, 0.089 mmol) was heated at about 85° C. for about 4 hrs. The mixture was cooled to about 20° C. and NaH (60% in oil, 20 mg, 0.5 mmol) was added. Stirring at about 20° C. was continued for about 18 hrs. The mixture was concentrated the residue was purified by chromatography to afford 5-methyl-1-(tetrahydro-2H-pyran-2-yl)-1H-pyrazole as an oil (400 mg, 20%)

$^1$H NMR (400 MHz, CDCl$_3$) δ: 7.45 (d, 1H), 6.05 (d, 1H), 5.24-5.30 (m, 1H), 4.00-4.08 (m, 1H), 3.61-3.70 (m, 1H), 2.41-2.55 (m, 1H), 2.35 (s, 3H), 2.08-2.18 (m, 1H), 1.93-2.02 (m, 1H), 1.65-1.77 (m, 2H), 1.55-1.64 (m, 1H).

GCMS m/z=166.1 [M]$^+$ and 3-methyl-1-(tetrahydro-2H-pyran-2-yl)-1H-pyrazole as an oil (352 mg, 15%).

$^1$H NMR (400 MHz, CDCl$_3$) δ: 7.48 (d, 1H), 6.08 (d, 1H), 5.29 (dd, 1H), 4.08 (dt, 1H), 3.64-3.74 (m, 1H), 2.30 (s, 3H), 2.07-2.18 (m, 1H), 1.98-2.07 (m, 2H), 1.64-1.77 (m, 3H).

GCMS m/z=166.1 [M]$^+$

Preparation 93

3-Methyl-1-(tetrahydro-2H-pyran-2-yl)-5-(4,4,5,5-tetramethyl-1,3,2-dioxaborolan-2-yl)-1H-pyrazole

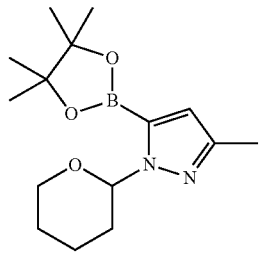

A 2.5 M solution of n-BuLi in hexane (0.44 mL, 1.10 mmol) was added to a solution of 3-methyl-1-(tetrahydro-2H-pyran-2-yl)-1H-pyrazole (Preparation 92, 200 mg, 1.10 mmol) in THF (2 mL) at about −70° C. The mixture was stirred at this temperature for about 10 min before 2-isopropoxy-4,4,5,5-tetramethyl-1,3,2-dioxaborolane (214 mg, 1.15 mmol) was added. The mixture was kept at about −70° C. for about 1 hrs longer, then warmed to about 20° C. and concentrated to afford the title compound admixed with about 65% unreacted 3-methyl-1-(tetrahydro-2H-pyran-2-yl)-1H-pyrazole. This mixture was used without further purification.

$^1$H NMR (400 MHz, CDCl$_3$) δ: 6.51 (s, 1H), 5.76 (dd, 1H), 4.01-4.12 (m, 1H), 3.59-3.74 (m, 1H), 2.37-2.51 (m, 2H), 2.29 (s, 3H), 1.97-2.18 (m, 1H), 1.62-1.76 (m, 2H), 1.47-1.62 (m, 1H), 1.33 (s, 12H).

GCMS m/z=292.2 [M]$^+$

Preparation 94

3-(Benzyloxy)-N-methoxy-N-methylcyclobutanecarboxamide

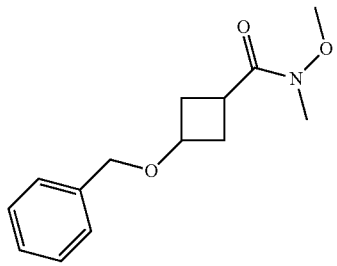 [SMILES: CON(C)C(=O)C1CC(OCc2ccccc2)C1]

To a solution of 3-(benzyloxy)cyclobutanecarboxylic acid (324 g, 1.57 mol) in DCM (1.5 L) was added CDI (280 g, 1.73 mol) in portions. The mixture was heated at reflux for about 2 hrs, after which N,O-dimethylhydroxylamine hydrochloride (183.7 g, 1.88 mol) and TEA (261 mL, 1.88 mol) were added. The mixture was heated at reflux for about 3 hrs further, then stirred at about 25° C. for about 16 hrs. The DCM was washed with saturated aq. $K_2CO_3$, dried ($K_2CO_3$), and concentrated. The residue was purified by chromatography to afford the title compound (298 g, 76%).

$^1$H NMR (400 MHz, DMSO-$d_6$) δ: 7.24-7.38 (m, 5H), 4.37 (s, 2H), 4.06-4.15 (m, 1H), 3.61 (s, 3H), 3.09 (s, 3H), 2.96 (s, 1H), 2.30-2.40 (m, 2H), 2.09-2.22 (m, 1H), 1.95-2.07 (m, 1H).

Preparation 95

1-[3-(Benzyloxy)cyclobutyl]ethanone

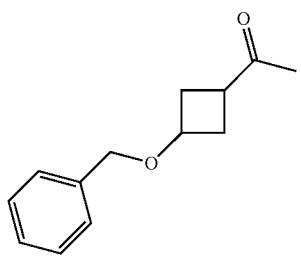

To a solution of 3-(benzyloxy)-N-methoxy-N-methylcyclobutanecarboxamide (Preparation 94, 298 g, 1.2 mol) in THF (1.5 L) was added dropwise a solution of methylmagnesium bromide (1.3 mol) at about 20° C. After the addition of methylmagnesium bromide was completed, the cooling bath was removed and the mixture was allowed to warm to about 25° C. Then 0.5 M aq. HCl (2.5 L) was added, and the mixture was extracted with $Et_2O$ (1 L+500 mL). The combined $Et_2O$ extracts were washed with water, dried ($Na_2SO_4$), and concentrated. The residue was purified by chromatography to afford the title compound (194 g, 79%).

$^1$H NMR (400 MHz, DMSO-$d_6$) δ: 7.24-7.38 (m, 5H), 4.35 (s, 2H), 3.90-3.99 (m, 0.5H), 3.16-3.24 (m, 0.5H), 2.75-2.87 (m, 1H), 2.31-2.40 (m, 2H), 2.06-2.15 (m, 1H), 2.04 (s, 1.5H), 1.99 (s, 1.5H), 1.87-1.97 (m, 1H).

Preparation 96

1-[3-(Benzyloxy)cyclobutyl]-3-(dimethylamino)prop-2-en-1-one

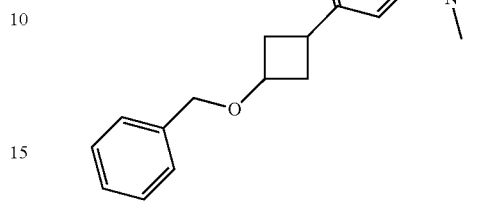

To a solution of 1-[3-(benzyloxy)cyclobutyl]ethanone (Preparation 95,194 g, 0.95 mol) in DMF (500 mL) was added dimethylformamide dimethyl acetal (285 g, 2.4 mol). The mixture was heated at about 110° C. for about 12 hrs. The mixture was concentrated to afford the title compound (258 g), which was used without purification or further characterization.

Preparation 97

5-[3-(Benzyloxy)cyclobutyl]-1H-pyrazole

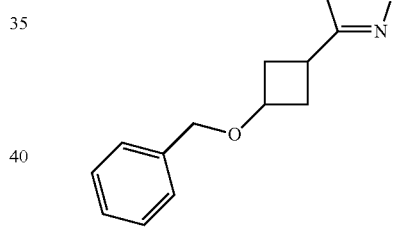

To a solution of 1-[3-(benzyloxy)cyclobutyl]-3-(dimethylamino)prop-2-en-1-one (Preparation 96, 110 g, 0.42 mol) in MeOH (500 mL) was added hydrazine hydrate (30 g, 0.6 mol). The mixture was heated at reflux for about 12 hrs, then concentrated. The residue was purified by chromatography to afford the title compound (79 g, 82%), which was used without purification or further characterization.

Preparation 98

3-(1H-Pyrazol-5-yl)cyclobutanol

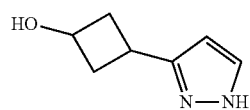

To a solution of 5-[3-(benzyloxy)cyclobutyl]-1H-pyrazole (Preparation 97, 79 g, 0.35 mol) in methanol (800 mL) in a 2 L hydrogenation flask was added palladium on carbon (10% Pd, 16 g). The mixture was pressurized under hydrogen (30 psi) and the mixture was shaken at about 60° C. for about 12 hrs. Additional palladium on carbon (10% Pd, 16 g) was added, and the hydrogenation was continued for about 10 hrs. The mixture was filtered and the filtrate was concentrated. The residue was purified by chromatography to afford the title compound (46 g, 96%), which was used without purification or further characterization.

Preparation 99

3-(1H-pyrazol-5-yl)cyclobutane-1-one

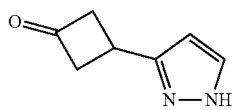

To a solution of oxalyl chloride (7.8 mL, 0.09 mol) in DCM (50 mL) at about −78° C. was added dropwise a solution of DMSO (12.7 mL, 0.18 mol) in DCM (50 mL). The mixture was stirred for about 30 min, then 3-(1H-pyrazol-5-yl)cyclobutanol (Preparation 98, 13.7 g, 0.09 mol) was added dropwise at this temperature. The resulting mixture was kept for about 30 min, after which TEA (25 mL, 0.18 mol) was added dropwise. The cooling bath was removed and the mixture was allowed to warm to about 25° C. and was kept at that temperature for about 3 hrs. Then an aqueous solution of $K_2CO_3$ (100 mL) was added. The DCM was separated, and the aqueous phase was extracted with DCM. The combined DCM extracts were washed with water, dried ($Na_2SO_4$), and concentrated. The residue was purified by chromatography to afford the title compound (7.4 g, 55%) as a white solid.

$^1$H NMR (400 MHz, DMSO-$d_6$) δ: 12.56 (s, 1H), 7.61 (s, 1H), 6.21 (d, 1H), 3.46-3.68 (m, 1H), 3.37-3.46 (m, 2H), 3.15-3.25 (m, 2H).

LCMS m/z=137.1 [MH]$^+$

Preparation 100

2-((1r,3s)-1-(4-(6-chloropyrazolo[1,5-a]pyrazin-4-yl)-1H-pyrazol-1-yl)-3-methoxycyclobutyl)acetonitrile (trans isomer)

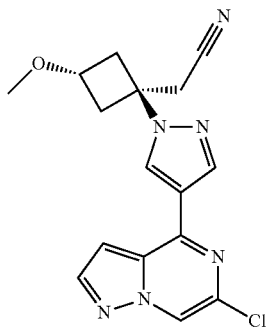 [SMILES: CO[C@H]1C[C@](CC#N)(n2cc(-c3nc(Cl)cn4nccc34)cn2)C1]

Part 1

To a solution of 2-((1r,3s)-1-(4-bromo-1H-pyrazol-1-yl)-3-methoxycyclobutyl)acetonitrile (Preparation 37, trans isomer, 3399 mg, 12.58 mmol) in 1,4-dioxane (33 mL) were added bis(pinacolato)diboron (3510 mg, 13.8 mmol) and KOAc (3700 mg, 37.7 mmol). The mixture was purged with argon for about 5 min, after which XPhos Pd G2 (1980 mg, 2.52 mmol) was added. The mixture was heated at about 65° C. for about 4 hrs. The cooled mixture was concentrated and the residue was purified by chromatography. The product was stirred with EtOAc (10 mL) at about 25° C., then heptane (40 mL) was added and crystallization was allowed to occur for about 30 min. The precipitate was filtered and dried to afford 2-((1r,3s)-3-methoxy-1-(4-(4,4,5,5-tetramethyl-1,3,2-dioxaborolan-2-yl)-1H-pyrazol-1-yl)cyclobutyl)acetonitrile as a white solid (1950 mg, 49%).

$^1$H NMR (400 MHz, CDCl$_3$) δ: 7.91 (s, 1H), 7.87 (s, 1H), 3.98 (tt, 1H), 3.29 (s, 3H), 3.17 (s, 2H), 2.97-3.07 (m, 2H), 2.44-2.53 (m, 2H), 1.33 (s, 12H).

LCMS m/z=318.0 [MH]$^+$

Part 2

A solution of 2-((1r,3s)-3-methoxy-1-(4-(4,4,5,5-tetramethyl-1,3,2-dioxaborolan-2-yl)-1H-pyrazol-1-yl)cyclobutyl)acetonitrile (Part 1, 1950 mg, 6.15 mmol) and 4,6-dichloropyrazolo[1,5-a]pyrazine (Preparation 4, 1160 mg, 6.15 mmol), and 2 M aq. $K_3PO_4$ (9.22 mL) in 1,4-dioxane (25 mL) was purged with argon for about 5 min, after which bis(tri-t-butylphosphine)palladium(0) (157 mg, 0.31 mmol) was added. The mixture was stirred at about 25° C. for about 2 hrs. The cooled mixture was diluted with EtOAc and the phases were separated. The aqueous phase was extracted twice with DCM. The combined EtOAc and DCM extracts were dried ($Na_2SO_4$) and concentrated. The residue was dissolved in DCM (20 mL) and heated at about 40° C. until all was dissolved, then heptane (10 mL) was added and crystallization was allowed to occur for about 30 min. The precipitate was filtered and dried to afford the title compound as an off white solid (1120 mg, 53%). The filtrate was concentrated and the residue was purified by chromatography to afford additional title compound (640 mg, 30%).

$^1$H NMR (500 MHz, CDCl$_3$) δ: 8.39 (d, 1H), 8.38 (s, 1H), 8.28 (s, 1H), 8.08 (d, 1H), 7.03 (dd, 1H), 4.03-4.10 (m, 1H), 3.34 (s, 3H), 3.25 (s, 2H), 3.08-3.16 (m, 2H), 2.53-2.60 (m, 2H).

LCMS m/z=343.3 [MH]$^+$ (Cl$^{35}$ isotope)

Preparation 101

Ethyl 5-methyl-1-(2-(1-methyl-1H-pyrazol-4-yl)-2-oxoethyl)-1H-pyrazole-3-carboxylate

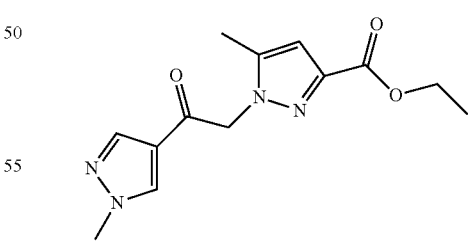

Ethyl 3-methyl-1H-pyrazole-5-carboxylate (92 mg, 0.6 mmol), 2-bromo-1-(1-methyl-1H-pyrazol-4-yl)ethan-1-one (Preparation 6, 134 mg, 0.66 mmol) and $K_2CO_3$ (104 mg, 0.75 mmol). were combined in MeCN (2 mL) and the suspension was stirred at about 40° C. for about 16 hrs. The solids were filtered and the filtrate was concentrated. The residue was purified by chromatography to afford the title compound as a yellow oil (125 mg, 5.5%).

¹H NMR (400 MHz, CDCl₃) δ: 7.86 (s, 2H), 6.73 (s, 1H), 5.65 (s, 2H), 4.26 (q, 2H), 3.95 (s, 3H), 2.32 (s, 3H), 1.31 (t, 3H).

LCMS m/z=277.1 [MH]⁺

Preparation 102

2-Methyl-6-(1-methyl-1H-pyrazol-4-yl)pyrazolo[1,5-a]pyrazin-4-ol

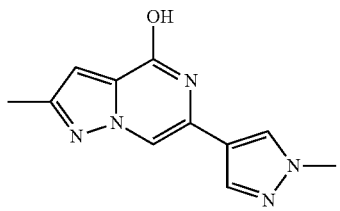

To a solution of ethyl 5-methyl-1-(2-(1-methyl-1H-pyrazol-4-yl)-2-oxoethyl)-1H-pyrazole-3-carboxylate (Preparation 101, 125 mg, 0.45 mmol) in EtOH (5 mL) was added NH₄OAc (105 mg, 1.06 mmol). The mixture was heated under microwave irradiation at about 105° C. for about 4 hrs. The mixture was concentrated and the residue was dissolved in EtOH and concentrated again to afford the title compound (110 mg, 85%).

¹H NMR (400 MHz, DMSO-d₆) δ: 8.25 (s, 1H), 8.01 (s, 1H), 7.97 (s, 1H), 6.76 (s, 1H), 3.87 (s, 3H), 2.34 (s, 3H).

LCMS m/z=230.0 [MH]⁺

Preparation 103

4-Chloro-2-methyl-6-(1-methyl-1H-pyrazol-4-yl)pyrazolo[1,5-a]pyrazine

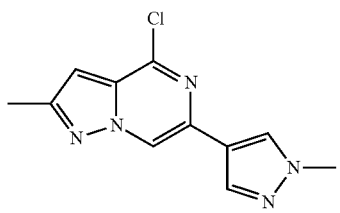

2-Methyl-6-(1-methyl-1H-pyrazol-4-yl)pyrazolo[1,5-a]pyrazin-4-ol (Preparation 102) was suspended in POCl₃ and heated at about 120° C. for about 6 hrs. The solution was concentrated afford an impure sample of the title compound which was used in the next step without further purification.

LCMS m/z=248.0 [MH]⁺ (Cl³⁵ isotope)

Example 36

(1r,3r)-3-(Cyanomethyl)-3-(4-(2-methyl-6-(1-methyl-1H-pyrazol-4-yl)pyrazolo[1,5-a]pyrazin-4-yl)-1H-pyrazol-1-yl)cyclobutane-1-carbonitrile (trans isomer)

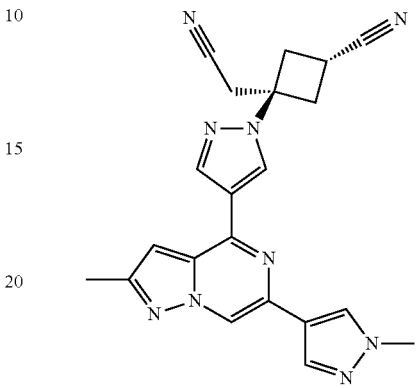

A mixture of crude 4-chloro-2-methyl-6-(1-methyl-1H-pyrazol-4-yl)pyrazolo[1,5-a]pyrazine (Preparation 103, 100 mg, 0.40 mmol), (1r,3r)-3-(cyanomethyl)-3-(4-(4,4,5,5-tetramethyl-1,3,2-dioxaborolan-2-yl)-1H-pyrazol-1-yl)cyclobutane-1-carbonitrile (Preparation 91, 132 mg, 0.42 mmol), Pd(dppf)Cl₂ DCM (16.5 mg, 0.02 mmol), and K₂CO₃ (167 mg, 1.21 mmol) were combined in a mixture of 1,4-dioxane (2.5 mL) and water (0.5 mL). The mixture was purged with nitrogen for about 5 min, then heated at about 90° C. for about 3 hrs. The mixture was concentrated and the residue was purified by chromatography and HPLC to afford the title compound (5.6 mg, 3% over two steps).

¹H NMR (400 MHz, CDCl₃) δ: 8.37 (s, 1H), 8.33 (s, 1H), 8.30 (s, 1H), 7.92 (s, 1H), 7.90 (s, 1H), 6.68 (s, 1H), 3.99 (s, 3H), 3.32-3.42 (m, 3H), 3.27 (s, 2H), 2.93-3.02 (m, 2H), 2.56 (s, 3H)

LCMS m/z=398.0 [MH]⁺

Preparation 104

3-((4-Methoxybenzyl)oxy)-1-methyl-1H-pyrazole

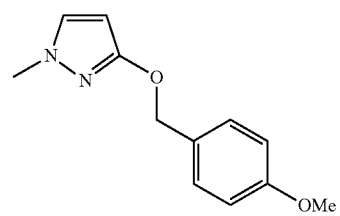 [SMILES: COc1ccc(COc2ccn(C)n2)cc1]

To a 100 mL round bottom flask were added 1-methyl-1H-pyrazol-3-ol (1.40 g, 14.3 mmol), DMF (30 mL), and K₂CO₃ (3.94 g, 28.5 mmol). Lastly 4-methoxybenzyl chloride (2.32 mL, 17.1 mmol) was added to the mixture. The mixture was heated at about 60° C. for about 8 hours. The mixture was then diluted with water (80 mL) and extracted with EtOAc (60 mL×3). The combined EtOAc extracts were washed with brine (60 mL×2), dried (Na₂SO₄) and concentrated. The residue was purified by chromatography to afford the title compound as a colorless oil (2.6 g, 83%).

$^1$H NMR (400 MHz, CDCl$_3$) δ: 7.38 (d, 2H), 7.13 (d, 1H), 6.91 (d, 2H), 5.64 (d, 1H), 5.11 (s, 2H), 3.82 (s, 3H), 3.76 (s, 3H).

LCMS m/z=218.9 [MH]$^+$

Preparation 105

4-Iodo-34(4-methoxybenzyl)oxy)-1-methyl-1H-pyrazole

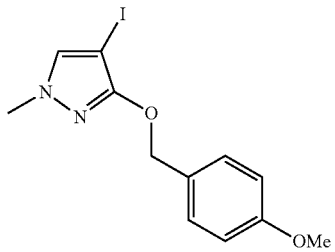 [SMILES: COc1ccc(COc2nn(C)cc2I)cc1]

To a 100 mL round bottom flask were added 3-((4-methoxybenzyl)oxy)-1-methyl-1H-pyrazole (Preparation 104, 1.0 g, 4.58 mmol) and MeCN (20 mL), after which ceric ammonium nitrate (1.51 g, 2.75 mmol) and iodine (698 mg, 2.75 mmol) were added to the mixture. The brown mixture was stirred at about 20° C. for about 1 h. The mixture was quenched with 5% aqueous sodium bisulfite (50 mL) and extracted with EtOAc (40 mL×3). The combined EtOAc extracts were dried (Na$_2$SO$_4$) and concentrated. The residue was purified by chromatography to afford the title compound as a green oil (800 mg, 51%).

$^1$H NMR (400 MHz, CDCl$_3$) δ: 7.40 (d, 2H), 7.19 (s, 1H), 6.91 (d, 2H), 5.18 (s, 2H), 3.82 (s, 3H), 3.77 (s, 3H).

Preparation 106

3-((4-Methoxybenzyl)oxy)-1-methyl-4-(4,4,5,5-tetramethyl-1,3,2-dioxaborolan-2-yl)-1H-pyrazole

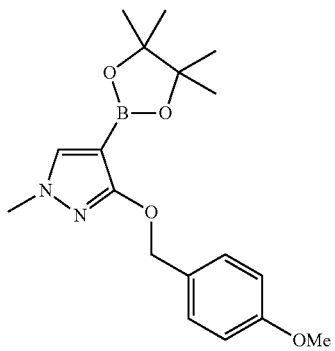 [SMILES: COc1ccc(COc2nn(C)cc2B2OC(C)(C)C(C)(C)O2)cc1]

To a 100 mL round bottom flask were added 4-iodo-3-((4-methoxybenzyl)oxy)-1-methyl-1H-pyrazole (Preparation 105, 800 mg, 2.32 mmol) and THF (16 mL). followed by the dropwise addition of isopropylmagnesium chloride (1.3 M in THF, 2.15 mL, 2.79 mmol) to the mixture at about −10° C. The mixture was stirred at a temperature between about −18° C. and 10° C. for about 45 min. 2-Isopropoxy-4,4,5,5-tetramethyl-1,3,2-dioxaborolane (649 mg, 3.49 mmol) was added to the mixture at about −10° C. and the mixture was allowed to warm to about 15° C. for about 1.5 h. Additional isopropylmagnesium chloride (1.3 M in THF, 0.72 mL, 0.93 mmol) and 2-isopropoxy-4,4,5,5-tetramethyl-1,3,2-dioxaborolane (216 mg, 1.16 mmol) were added to the mixture at about −15° C. The mixture was allowed to warm to about 15° C. for about 1 h. The mixture was diluted with EtOAc (40 mL) and washed with saturated aqueous NH$_4$Cl (30 mL), brine (30 mL), dried (Na$_2$SO$_4$), and concentrated. The residue was purified by chromatography to afford the title compound as a white solid (600 mg, 75%).

$^1$H NMR (400 MHz, CDCl$_3$) δ: 7.40-7.45 (m, 3H), 6.88 (d, 2H), 5.24 (s, 2H), 3.81 (s, 3H), 3.73 (s, 3H), 1.31 (s, 12H).

LCMS m/z=345.1 [MH]$^+$

Preparation 107

(1r,3r)-3-(Cyanomethyl)-3-(4-(6-(34(4-methoxybenzyl)oxy)-1-methyl-1H-pyrazol-4-yl)pyrazolo[1,5-a]pyrazin-4-yl)-1H-pyrazol-1-yl)cyclobutane-1-carbonitrile

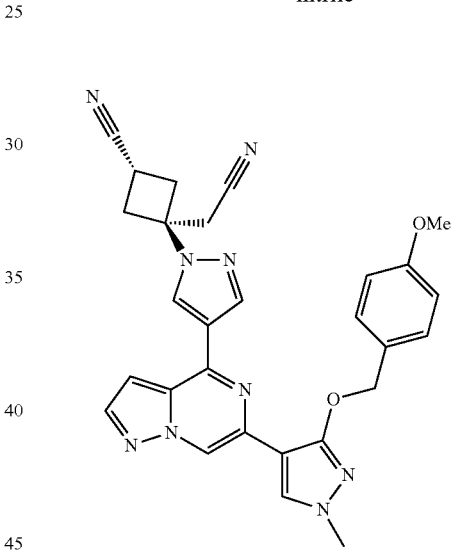

To a 25 ml round bottom flask were added (1r,3r)-3-(4-(6-chloropyrazolo[1,5-a]pyrazin-4-yl)-1H-pyrazol-1-yl)-3-(cyanomethyl)cyclobutane-1-carbonitrile (Preparation 75, 300 mg, 0.88 mmol), 3-((4-methoxybenzyl)oxy)-1-methyl-4-(4,4,5,5-tetramethyl-1,3,2-dioxaborolan-2-yl)-1H-pyrazole (Preparation 106, 367 mg, 1.07 mmol), dioxane (16 mL), XPhos Pd G2 (140 mg, 0.178 mmol) and 2 M aq. K$_3$PO$_4$ (3.55 mL, 7.11 mmol). The mixture was placed under nitrogen, then heated at about 60° C. for about 4 h. The mixture was diluted with water (70 mL) and extracted with EtOAc (50 mL×3). The combined EtOAc extracts were dried (Na$_2$SO$_4$) and concentrated. The residue was purified by chromatography to afford the title compound as a yellow solid (450 mg, 98%).

$^1$H NMR (400 MHz, DMSO-d$_6$) δ: 8.92 (s, 1H), 8.57 (s, 1H), 8.52 (s, 1H), 8.31 (s, 1H), 8.16 (d, 1H), 7.50 (d, 2H), 7.45 (s, 1H), 7.00 (d, 2H), 5.29 (s, 2H), 3.95 (s, 3H), 3.82 (s, 3H), 3.55-3.59 (m, 1H), 3.52 (s, 2H), 3.25-3.32 (m, 2H), 2.94 (dd, 2H).

LCMS m/z=542.1 [MNa]$^+$

Example 37

(1r,3r)-3-(Cyanomethyl)-3-(4-(6-(1-methyl-3-oxo-2,3-dihydro-1H-pyrazol-4-yl)pyrazolo[1,5-a]pyrazin-4-yl)-1H-pyrazol-1-yl)cyclobutane-1-carbonitrile (trans isomer)

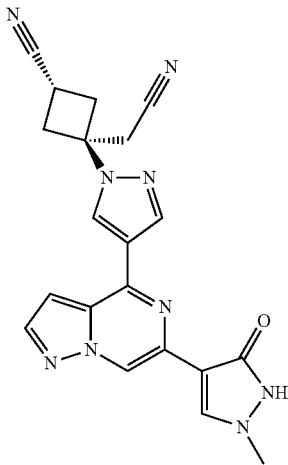 [SMILES: Cn1cc(-c2cn3nccc3c(-c3cnn([C@]4(CC#N)C[C@@H](C#N)C4)c3)n2)c(=O)[nH]1]

(1r,3r)-3-(Cyanomethyl)-3-(4-(6-(3(4(4-methoxybenzyl)oxy)-1-methyl-1H-pyrazol-4-yl)pyrazolo[1,5-a]pyrazin-4-yl)-1H-pyrazol-1-yl)cyclobutane-1-carbonitrile (Preparation 107, 450 mg, 0.86 mmol) and TFA (13 mL) were stirred at about 10° C. for about 4 h. The mixture was concentrated and the residue was diluted with DCM (40 mL) and MeOH (40 mL) and neutralized with solid NaHCO3. The mixture was filtered. The filtrate was concentrated and the residue was purified by HPLC to afford the title compound as a yellow solid (54 mg, 16%).

$^1$H NMR (400 MHz, DMSO-d$_6$) δ: 10.76 (br. s., 1H), 8.92 (s, 1H), 8.71 (s, 1H), 8.51 (s, 1H), 8.18 (d, 1H), 8.16 (s, 1H), 7.45 (d, 1H), 3.73 (s, 3H), 3.55-3.62 (m, 1H), 3.53 (s, 2H), 3.25-3.33 (m, 2H), 2.90-2.99 (m, 2H).

LCMS m/z=400.1 [MH]$^+$

Biological Evaluation

Compounds of the invention were evaluated by in vitro methods to determine their respective ability to inhibit the JAK kinases (TYK2, JAK1, JAK2, JAK3).

Assay Format

The human JAK inhibitory activity was determined by using a microfluidic assay to monitor phosphorylation of a synthetic peptide by the recombinant human kinase domain of each of the four members of the JAK family, JAK1, JAK2, JAK3 and TYK2. Reaction mixtures contained 1 μM of a fluorescently labeled synthetic peptide, a concentration less than the apparent K$_m$, and 1 mM ATP. Each assay condition was optimized for enzyme concentration and room temperature incubation time to obtain a conversion rate of 20% to 30% phosphorylated peptide product. Reactions were terminated by the addition of stop buffer containing EDTA. Utilizing the LabChip 3000 mobility shift technology (Caliper Life Science), each assay reaction was sampled to determine the level of phosphorylation. This technology is separation-based, allowing direct detection of fluorescently labeled substrates and products. Separations are controlled by a combination of vacuum pressure and electric field strength optimized for each peptide substrate.

Assay Protocol

JAK Caliper Enzyme Assay at 1 mM ATP

Compounds were added to a 384-well plate. Reaction mixtures contained 10 mM HEPES, pH 7.4, 10 mM MgCl$_2$, 0.01% BSA, 0.0005% Tween 20, 1 mM ATP and 1 μM peptide substrate. The JAK1 and TYK2 assays contained 1 μM of the IRStide peptide (5FAM-KKSRGDYMTMQID) and the JAK2 and JAK3 assays contained 1 μM of the JAKtide peptide (FITC-KGGEEEEYFELVKK). The assays were initiated by the addition of 20 nM JAK1, 1 nM JAK2, 1 nM JAK or 1 nM TYK2 enzyme and were incubated at room temperature for three hours for JAK1, 60 minutes for JAK2, 75 minutes for JAK3 or 135 minutes for TYK2. Enzyme concentrations and incubation times were optimized for each new enzyme preps and were modified slightly over time to ensure 20% to 30% phosphorylation. The assays were stopped with 15 μL of 180 mM HEPES, pH 7.4, 20 mM EDTA, and 0.2% Coating Reagent 3. The assay plates were placed on a Caliper Life Science LC3000 instrument, and each well was sampled using appropriate separation conditions to measure the unphosphorylated and phosphorylated peptide.

Data Analysis

The data was collected using the HTS Well Analyzer software from Caliper Life Sciences. The data output for data analysis is the percent product converted calculated on peak height (Equation 1).

$$\% \text{ product converted}=100*((\text{product})/(\text{product+substrate})) \quad \text{Equation 1:}$$

The percent effect at each compound concentration was calculated based on the positive and negative control well contained within each assay plate (Equation 2). The positive control wells contained a saturating concentration of a control compound that produced a level of phosphorylation comparable to background (i.e., completely inhibited JAK1, JAK2, JAK3 or TYK2). The negative control wells contained DMSO alone (at the same concentration as the compound wells) that was used to set the baseline activity in the assay (i.e., uninhibited JAK1, JAK2, JAK3 or TYK2).

$$\% \text{ effect}=100*((\text{sample well}-\text{negative control})/(\text{positive control-negative control})) \quad \text{Equation 2:}$$

The percent effect was plotted against the compound concentration compound. An unconstrained sigmoid curve was fitted using a 4 parameter logistic model and the compound concentration required for 50% inhibition (IC$_{50}$) was determined (Equation 3).

$$y=((\text{max}-\text{min})/(1+((x/IC_{50})\hat{}s)))+\text{min} \quad \text{Equation 3:}$$

Where max is the maximum asymptote (complete inhibition), min is the minimum asymptote (no inhibition) and s is the slope factor. IC$_{50}$ values are reported in nM for each compound:

TABLE I

| | JAK Caliper Data | | | |
|---|---|---|---|---|
| Example No. | TYK2 IC50 (nM) | JAK1 IC50 (nM) | JAK2 IC50 (nM) | JAK3 IC50 (nM) |
| 1 | 18 | 291 | 40 | >9788 |
| 2 | 62 | 1057 | 299 | >10000 |
| 3 | 64 | 2292 | 487 | >10000 |
| 4 | 55 | 1338 | 141 | >10000 |

TABLE I-continued

JAK Caliper Data

| Example No. | TYK2 IC50 (nM) | JAK1 IC50 (nM) | JAK2 IC50 (nM) | JAK3 IC50 (nM) |
|---|---|---|---|---|
| 5 | 35 | 1917 | 472 | >10000 |
| 6 | 21 | 5720 | 500 | >10000 |
| 7 | 7 | 250 | 37 | 6682 |
| 8 | 11 | 265 | 42 | >9282 |
| 9 | 8 | 185 | 49 | >10000 |
| 10 | 580 | 5709 | 1601 | >10000 |
| 11 | 8 | 273 | 38 | >6170 |
| 12 | 24 | 764 | 159 | >10000 |
| 13 | 149 | 3228 | 487 | >10000 |
| 14 | 81 | 1061 | 367 | >10000 |
| 15 | 22 | 1495 | 228 | >9121 |
| 16 | 16 | 664 | 99 | 10000 |
| 17 | 35 | 1728 | 205 | 10000 |
| 18 | 47 | 1079 | 206 | 10000 |
| 19 | 6 | 21 | 8 | 1051 |
| 20 | 16 | 383 | 74 | >10000 |
| 21 | 34 | 1288 | 109 | >10000 |
| 22 | 30 | 2544 | 127 | >10000 |
| 23 | 9 | 431 | 26 | 9410 |
| 24 | 25 | 3550 | 432 | >10000 |
| 25 | 23 | 319 | 99 | >10000 |
| 26 | 21 | 713 | 158 | >10000 |
| 27 | 24 | 737 | 171 | >10000 |
| 28 | 27 | 1362 | 249 | >10000 |
| 29 | 352 | 3932 | 3041 | >10000 |
| 30 | 7 | 174 | 71 | >10000 |
| 31 | 38 | >9857 | 324 | >10000 |
| 32 | 17 | 2254 | 339 | >10000 |
| 33 | 52 | 8717 | 444 | >10000 |
| 34 | 11 | 96 | 19 | 3263 |
| 35 | 136 | 1915 | 268 | >10000 |
| 36 | 1605 | 3521 | 755 | >10000 |
| 37 | 32 | 3489 | 166 | >10000 |

Selected compounds were assessed for their ability to inhibit IL-12 signaling in a human whole blood flow cytometry assay. IL-12 signals through TYK2 and JAK2.

Human Whole Blood IL-12 Induced STAT4 Phosphorylation Assay

Test articles were prepared as 30 mM stocks in DMSO. An 11-point 2.5 dilution series was created in DMSO with a top concentration of 10 mM. Further dilution was done by adding 4 µL of the above test article solutions into 96 µL of PBS with a top concentration of 400 µM. Human whole blood was collected from healthy donors via vein puncture into Vacutainer collection tubes containing sodium heparin (Catalog No. 366480; Becton Dickinson, Franklin Lakes, N.J.). Blood was warmed to 37° C. prior to use. Human whole blood was aliquoted (90 mL/well) in 96-well, deep-well, V-bottom plates and treated with compounds at 11 different concentrations (0.2% DMSO final) at 37° C. for 60 minutes. This was followed by a challenge with IL-12 (5 mL/well; final, 5 ng/mL) for 15 minutes. Samples were treated with warm 1× Lyse/Fix buffer (700 mL/well) to terminate activation and further incubated at 37° C. for 20 minutes to lyse red blood cells. Plates were centrifuged at 300×g for 5 minutes, supernatant was aspirated, and cells were washed with 800 mL per well of staining buffer (PBS containing 0.5% fetal bovine serum and 0.01% sodium azide). The washed cell pellets were resuspended with 350 mL/well of pre-chilled 90% methanol, and incubated at 4° C. for 30 minutes. Plates were centrifuged at 300×g for 5 minutes, supernatant containing 90% methanol was aspirated, and cells were washed with 800 mL/well of staining buffer. Cell pellets were resuspended in staining buffer containing anti-pSTAT4-AlexaFluor647 (1 to 150 dilution, 150 mL/well), and incubated at room temperature in the dark overnight.

Samples were transferred to 96-well U-bottom plates and flow cytometric analysis was performed on a FACSCalibur or LSRFortessa equipped with a HTS plate loader (BD Biosciences). The lymphocyte population was gated for histogram analysis of pSTAT4. Background fluorescence was defined using unstimulated cells and a gate was placed at the foot of the peak to include ~0.5% gated population. The histogram statistical analysis was performed using CellQuestÒ Pro version 5.2.1 (BD Biosciences) or FACSDiva version 6.2 (BD Biosciences) software. Relative fluorescence unit (RFU), which measures the level of phospho STAT4, was calculated by multiplying the percent positive population and its mean fluorescence. Data from 11 compound concentrations (singlicate at each concentration) was normalized as a percentage of control based on the formula:

% of Control=100×(A−B)/(C−B)

where A is the RFU from wells containing compound and IL-12, B is the RFU from wells without IL-12 and compound (minimum fluorescence) and C is the RFU from wells containing only IL-12 (maximum fluorescence). Inhibition curves and $IC_{50}$ values were determined using the Prism version 5 software (GraphPad, La Jolla, Calif.).

TABLE II

Human whole blood IL-12 Data.

| Example Number | HWB IL-12 $IC_{50}$ (nM) |
|---|---|
| 1 | 162 |
| 3 | 203 |
| 7 | 41 |
| 19 | 28 |
| 20 | 50 |
| 23 | 34 |
| 25 | 59 |
| 27 | 86 |
| 30 | 46 |
| 32 | 130 |

What is claimed is:
1. A compound having the structure (I):

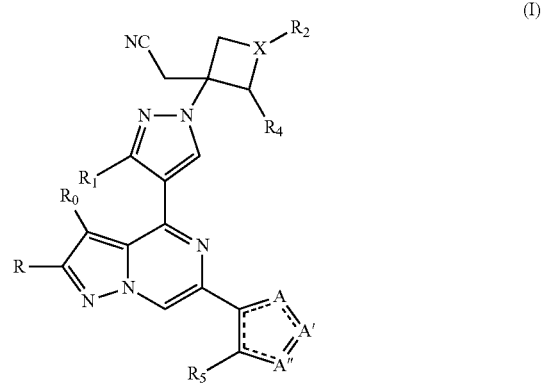

(I)

or a pharmaceutically acceptable salt thereof, or a pharmaceutically acceptable solvate of said compound or pharmaceutically acceptable salt, wherein:

A, A' and A" are independently O, C=O, C—R' or N—R", where R' and R" may independently be H, amino, —NR$_7$COR$_6$, COR$_6$, —CONR$_7$R$_8$, C$_1$-C$_6$ alkyl, or hydroxy(C$_1$-C$_6$ alkyl)-, and R" may be present or absent, and is present where the rules of valency permit, and where not more than one of A, A' and A" is O or C=O;

R$_0$ and R are independently H, Br, Cl, F, or C$_1$-C$_6$ alkyl;

R$_1$ is H, C$_1$-C$_6$ alkyl, or hydroxy(C$_1$-C$_6$ alkyl)-;

R$_2$ is selected from the group consisting of H, C$_1$-C$_6$ alkyl-, C$_1$-C$_6$ alkoxy-, hydroxy(C$_1$-C$_6$ phenyl(C$_1$-C$_6$ formyl, heteroaryl, heterocyclic, —COR$_6$, —OCOR$_6$, —COOR$_6$, —NR$_7$COR$_6$, CONR$_7$R$_8$, and —(CH$_2$)$_n$—W, where W is cyano, hydroxy, C$_3$-C$_8$ cycloalkyl, —SO$_2$NR$_7$R$_8$, and —SO$_2$—R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl;

X is C—R$_3$ or N, where R$_3$ may be H, C$_1$-C$_6$ alkyl, amino, cyano, or C$_1$-C$_6$ alkoxy;

R$_4$ and R$_5$ are independently H, amino, C$_1$-C$_6$ alkyl, or hydroxy(C$_1$-C$_6$ alkyl)-;

R$_6$, R$_7$ and R$_8$ are each independently H, C$_1$-C$_6$ alkyl, C$_1$-C$_4$ alkoxy(C$_1$-C$_6$ alkyl) or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl;

and, n is 0, 1, 2 or 3.

2. The compound of claim 1 having the structure (Ia):

(Ia)

or a pharmaceutically acceptable salt thereof, or a pharmaceutically acceptable solvate of said compound or pharmaceutically acceptable salt, wherein:

A, A' and A" are independently O, C=O, C—R' or N—R", where R' and R" may independently be H, amino, —NR$_7$COR$_6$, COR$_6$, —CONR$_7$R$_8$, C$_1$-C$_6$ alkyl, or hydroxy(C$_1$-C$_6$ alkyl), and R" may be present or absent, and is present where the rules of valency permit, and where not more than one of A, A' and A" is O or C=O;

R$_0$ and R are independently H, Br, Cl, F, or C$_1$-C$_6$ alkyl;

R$_1$ is H, C$_1$-C$_6$ alkyl, or hydroxy(C$_1$-C$_6$ alkyl);

R$_2$ is selected from the group consisting of H, C$_1$-C$_6$ alkyl-, C$_1$-C$_6$ alkoxy-, hydroxy(C$_1$-C$_6$ phenyl(C$_1$-C$_6$ formyl, heteroaryl, heterocyclic, —COR$_6$, —OCOR$_6$, —COOR$_6$, —NR$_7$COR$_6$, —CONR$_7$R$_8$, and —(CH$_2$)$_n$—W, where W is cyano, hydroxy, C$_3$-C$_8$ cycloalkyl, —SO$_2$NR$_7$R$_8$, and —SO$_2$—R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl;

R$_3$ may be H, C$_1$-C$_6$ alkyl, amino, cyano, or C$_1$-C$_6$ alkoxy;

R$_4$ and R$_5$ are independently H, amino, C$_1$-C$_6$ alkyl, or hydroxy(C$_1$-C$_6$ alkyl)-;

R$_6$, R$_7$ and R$_8$ are each independently H, C$_1$-C$_6$ alkyl, C$_1$-C$_4$ alkoxy(C$_1$-C$_6$ alkyl)-, or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl;

and, n is 0, 1, 2 or 3.

3. The compound of claim 1 having the structure (Ib):

(Ib)

or a pharmaceutically acceptable salt thereof, or a pharmaceutically acceptable solvate of said compound or pharmaceutically acceptable salt, wherein:

R" is H, —COR$_6$, —CONR$_7$R$_8$, C$_1$-C$_6$ alkyl, or hydroxy (C$_1$-C$_6$ alkyl)-;

R$_0$ and R are independently H, Br, Cl, F, or C$_1$-C$_6$ alkyl;

R$_1$ is H, C$_1$-C$_6$ alkyl, or hydroxy(C$_1$-C$_6$ alkyl);

R$_2$ is selected from the group consisting of H, C$_1$-C$_6$ alkyl, C$_1$-C$_6$ alkoxy, hydroxy(C$_1$-C$_6$ alkyl), phenyl(C$_1$-C$_6$ alkyl), formyl, heteroaryl, heterocyclic, —COR$_6$, —OCOR$_6$, —COOR$_6$, —NR$_7$COR$_6$, —CONR$_7$R$_8$, and —(CH$_2$)$_n$—W, where W is cyano, hydroxy, C$_3$-C$_8$ cycloalkyl, —SO$_2$NR$_7$R$_8$, and —SO$_2$—R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl;

R$_3$ may be H, C$_1$-C$_6$ alkyl, amino, cyano, or C$_1$-C$_6$ alkoxy;

R$_5$ is independently H, amino, C$_1$-C$_6$ alkyl, or hydroxy (C$_1$-C$_6$ alkyl);

R$_6$, R$_7$ and R$_8$ are each independently H, C$_1$-C$_6$ alkyl, C$_1$-C$_4$ alkoxy(C$_1$-C$_6$ alkyl), or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl;

and, n is 0, 1, 2 or 3.

4. The compound of claim 3 wherein R" is C$_1$-C$_6$ alkyl and R$_5$ is H.

5. The compound of claim 1 having the structure (Ic):

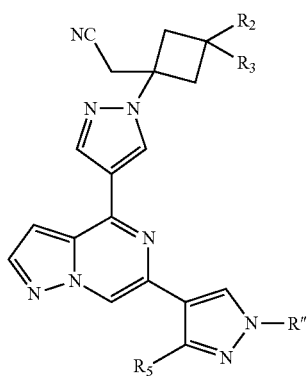

(Ic)

or a pharmaceutically acceptable salt thereof, or a pharmaceutically acceptable solvate of said compound or pharmaceutically acceptable salt, wherein:

R" is H, —$COR_6$, —$CONR_7R_8$, $C_1$-$C_6$ alkyl-, or hydroxy ($C_1$-$C_6$ alkyl)-;

$R_2$ is selected from the group consisting of H, $C_1$-$C_6$ alkyl, $C_1$-$C_6$ alkoxy-, hydroxy($C_1$-$C_6$ alkyl)-, phenyl($C_1$-$C_6$ alkyl-), formyl, heteroaryl, heterocyclic, —$COR_6$, —$OCOR_6$, —$COOR_6$, —$NR_7COR_6$, —$CONR_7R_8$, and —$(CH_2)_n$—W, where W is cyano, hydroxy, $C_3$-$C_8$ cycloalkyl, —$SO_2NR_7R_8$, and —$SO_2$—$R_9$, where $R_9$ is $C_1$-$C_6$ alkyl, $C_3$-$C_8$ cycloalkyl, heteroaryl, or heterocyclic; wherein each of said alkyl, cycloalkyl, heterocyclic, or heteroaryl may be unsubstituted or substituted by halo, cyano, hydroxy, or $C_1$-$C_6$ alkyl;

$R_3$ is H, $C_1$-$C_6$ alkyl, amino, cyano, or $C_1$-$C_6$ alkoxy-;

$R_5$ is H, amino, $C_1$-$C_6$ alkyl, or hydroxy($C_1$-$C_6$ alkyl)-;

$R_6$, $R_7$ and $R_8$ are each are each independently H, $C_1$-$C_6$ alkyl, $C_1$-$C_4$ alkoxy($C_1$-$C_6$ alkyl)-, or $C_3$-$C_8$ cycloalkyl, said $C_1$-$C_6$ alkyl is optionally substituted by halo, CN or hydroxy; or, $R_7$ and $R_8$ together with the atom bonded thereto form a 5- or 6-membered ring, said ring being optionally substituted by halo, hydroxy, CN, or $C_1$-$C_6$ alkyl;

and, n is 0, 1, 2 or 3.

6. The compound of claim 5 wherein R" is $C_1$-$C_6$ alkyl and $R_5$ is H.

7. The compound of claim 1 having the structure (Id):

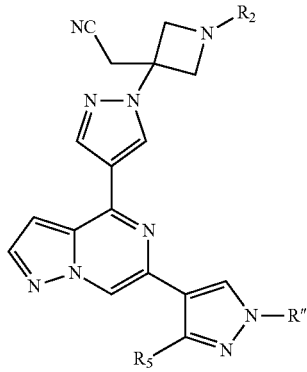

(Id)

or a pharmaceutically acceptable salt thereof, or a pharmaceutically acceptable solvate of said compound or pharmaceutically acceptable salt, wherein:

R" is H, —$COR_6$, —$CONR_7R_8$, $C_1$-$C_6$ alkyl, or hydroxy ($C_1$-$C_6$ alkyl)-;

$R_2$ is selected from the group consisting of H, $C_1$-$C_6$ alkyl, $C_1$-$C_6$ alkoxy-, hydroxy($C_1$-$C_6$ alkyl)-, phenyl($C_1$-$C_6$ alkyl)-, formyl, heteroaryl, heterocyclic, —$COR_6$, —$OCOR_6$, —$COOR_6$, —$CONR_7R_8$, and —$(CH_2)_n$—W, where W is cyano, hydroxy, $C_3$-$C_8$ cycloalkyl-, —$SO_2NR_7R_8$, and —$SO_2$—$R_9$, where $R_9$ is $C_1$-$C_6$ alkyl, $C_3$-$C_8$ cycloalkyl, heteroaryl, or heterocyclic; wherein each of said alkyl, cycloalkyl, heterocyclic, or heteroaryl may be unsubstituted or substituted by halo, cyano, hydroxy, or $C_1$-$C_6$ alkyl;

$R_5$ is H, amino, $C_1$-$C_6$ alkyl-, or hydroxy($C_1$-$C_6$ alkyl)-;

$R_6$, $R_7$ and $R_8$ are each are each independently H, $C_1$-$C_6$ alkyl, $C_1$-$C_4$ alkoxy($C_1$-$C_6$ alkyl), or $C_3$-$C_8$ cycloalkyl, said $C_1$-$C_6$ alkyl is optionally substituted by halo, CN or hydroxy; or, $R_7$ and $R_8$ together with the atom bonded thereto form a 5- or 6-membered ring, said ring being optionally substituted by halo, hydroxy, CN, or $C_1$-$C_6$ alkyl;

and, n is 0, 1, 2 or 3.

8. The compound of claim 7 wherein R" is $C_1$-$C_6$ alkyl and $R_5$ is H.

9. The compound of claim 1 having the structure (Ie):

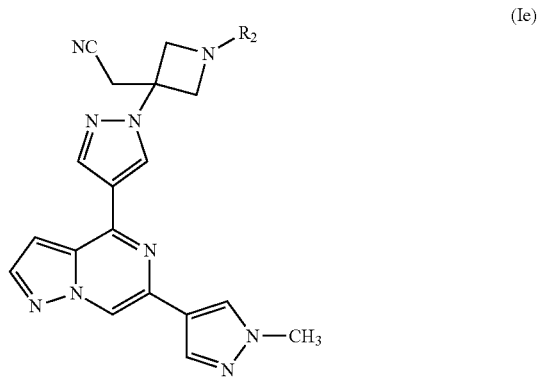

(Ie)

or a pharmaceutically acceptable salt thereof, or a pharmaceutically acceptable solvate of said compound or pharmaceutically acceptable salt, wherein:

$R_2$ is selected from the group consisting of H, $C_1$-$C_6$ alkyl, $C_1$-$C_6$ alkoxy-, hydroxy($C_1$-$C_6$ alkyl)-, phenyl($C_1$-$C_6$ alkyl)-, formyl, heteroaryl, heterocyclic —$COR_6$, —$OCOR_6$, —$COOR_6$, —$CONR_7R_8$, and —$(CH_2)_n$—W, where W is cyano, hydroxy, $C_3$-$C_8$ cycloalkyl, —$SO_2NR_7R_8$, and $SO_2$—$R_9$, where $R_9$, where $R^9$ is $C_1$-$C_6$ alkyl, $C_3$-$C_8$ cycloalkyl, heteroaryl, or heterocyclic; wherein each of said alkyl, cycloalkyl, heterocyclic, or heteroaryl may be unsubstituted or substituted by halo, cyano, hydroxy, or $C_1$-$C_6$ alkyl;

$R_6$, $R_7$ and $R_8$ are each are each independently H, $C_1$-$C_6$ alkyl, $C_1$-$C_4$ alkoxy($C_1$-$C_6$ alkyl), or $C_3$-$C_8$ cycloalkyl, said $C_1$-$C_6$ alkyl is optionally substituted by halo, CN or hydroxy; or, $R_7$ and $R_8$ together with the atom bonded thereto form a 5- or 6-membered ring, said ring being optionally substituted by halo, hydroxy, CN, or $C_1$-$C_6$ alkyl;

and, n is 0, 1, 2 or 3.

10. The compound of claim 9 wherein R₂ is —(CH₂)ₙ—W, where W is cyano and n is 1, 2 or 3.

11. The compound of claim 1 having the structure (If):

(If)

[Chemical structure diagram showing a cyclobutane with NC-CH₂ and CN/H substituents, connected to a pyrazole-pyrazolo[1,5-a]pyrazine-pyrazole system with R" and R₅ substituents]

or a pharmaceutically acceptable salt thereof, or a pharmaceutically acceptable solvate of said compound or pharmaceutically acceptable salt, wherein:
R" is H, C₁-C₆ alkyl, or hydroxy(C₁-C₆ alkyl)-; and,
R₅ is H, amino, C₁-C₆ alkyl, or hydroxy(C₁-C₆ alkyl)-.

12. The compound of claim 11 wherein R" is C₁-C₆ alkyl and R₅ is H.

13. The compound of claim 1 selected from the group consisting of:
- (1r,3r)-3-(4-(6-(3-amino-1-methyl-1H-pyrazol-4-yl)pyrazolo[1,5-a]pyrazin-4-yl)-1H-pyrazol-1-yl)-3-(cyanomethyl)cyclobutane-1-carbonitrile;
- 2,2'-(3-(4-(6-(1-methyl-1H-pyrazol-4-yl)pyrazolo[1,5-a]pyrazin-4-yl)-1H-pyrazol-1-yl)azetidine-1,3-diyl)diacetonitrile;
- 2-((1s,3r)-1-(4-(6-(5-(hydroxymethyl)-1H-pyrazol-3-yl)pyrazolo[1,5-a]pyrazin-4-yl)-1H-pyrazol-1-yl)-3-methoxycyclobutyl)acetonitrile;
- 5-(4-(1-((1s,3r)-1-(cyanomethyl)-3-methoxycyclobutyl)-1H-pyrazol-4-yl)pyrazolo[1,5-a]pyrazin-6-yl)-1H-pyrazole-3-carboxamide;
- (1s,3s)-3-(cyanomethyl)-3-(4-(6-(5-(hydroxymethyl)isoxazol-3-yl)pyrazolo[1,5-a]pyrazin-4-yl)-1H-pyrazol-1-yl)cyclobutane-1-carbonitrile;
- (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile;
- (1s,3s)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile;
- (1r,3r)-3-(cyanomethyl)-3-(4-(3-methyl-6-(1-methyl-1H-pyrazol-4-yl)pyrazolo[1,5-a]pyrazin-4-yl)-1H-pyrazol-1-yl)cyclobutane-1-carbonitrile;
- 2-((1r,3s)-1-(4-(6-(3-amino-1H-pyrazol-5-yl)pyrazolo[1,5-a]pyrazin-4-yl)-1H-pyrazol-1-yl)-3-methoxycyclobutyl)acetonitrile;
- 2-(1-ethyl-3-(4-(6-(5-(hydroxymethyl)-1H-pyrazol-3-yl)pyrazolo[1,5-a]pyrazin-4-yl)-1H-pyrazol-1-yl)azetidin-3-yl)acetonitrile;
- (1r,3r)-3-(Cyanomethyl)-3-(4-(6-(1-methyl-3-oxo-2,3-dihydro-1H-pyrazol-4-yl)pyrazolo[1,5-a]pyrazin-4-yl)-1H-pyrazol-1-yl)cyclobutane-1-carbonitrile (trans isomer);
- (1r,3r)-3-(cyanomethyl)-3-(4-(6-(1-(hydroxymethyl)-1H-pyrazol-4-yl)pyrazolo[1,5-a]pyrazin-4-yl)-1H-pyrazol-1-yl)cyclobutane-1-carbonitrile; and, or, a pharmaceutically acceptable salt thereof.

14. The compound of claim 1 wherein the compound is (1r,3r)-3-(4-(6-(3-amino-1-methyl-1H-pyrazol-4-yl)pyrazolo[1,5-a]pyrazin-4-yl)-1H-pyrazol-1-yl)-3-(cyanomethyl)cyclobutane-1-carbonitrile, or a pharmaceutically acceptable salt thereof.

15. The compound of claim 1 wherein the compound is 2,2'-(3-(4-(6-(1-methyl-1H-pyrazol-4-yl)pyrazolo[1,5-a]pyrazin-4-yl)-1H-pyrazol-1-yl)azetidine-1,3-diyl)diacetonitrile, or a pharmaceutically acceptable salt thereof.

16. The compound of claim 1 wherein the compound is 2-((1s,3r)-1-(4-(6-(5-(hydroxymethyl)-1H-pyrazol-3-yl)pyrazolo[1,5-a]pyrazin-4-yl)-1H-pyrazol-1-yl)-3-methoxycyclobutyl)acetonitrile, or a pharmaceutically acceptable salt thereof.

17. The compound of claim 1 wherein the compound is 5-(4-(14(1s,30-1-(cyanomethyl)-3-methoxycyclobutyl)-1H-pyrazol-4-yl)pyrazolo[1,5-a]pyrazin-6-yl)-1H-pyrazole-3-carboxamide, or a pharmaceutically acceptable salt thereof.

18. (1s,3s)-3-(Cyanomethyl)-3-(4-(6-(5-(hydroxymethyl)isoxazol-3-yl)pyrazolo[1,5-a]pyrazin-4-yl)-1H-pyrazol-1-yl)cyclobutane-1-carbonitrile, or, a pharmaceutically acceptable salt thereof.

19. (1r,3r)-3-(Cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, or a pharmaceutically acceptable salt thereof.

20. The compound of claim 1 wherein the compound is (1s,3s)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, or a pharmaceutically acceptable salt thereof.

21. The compound of claim 1 wherein the compound is (1r,3r)-3-(cyanomethyl)-3-(4-(3-methyl-6-(1-methyl-1H-pyrazol-4-yl)pyrazolo[1,5-a]pyrazin-4-yl)-1H-pyrazol-1-yl)cyclobutane-1-carbonitrile, or a pharmaceutically acceptable salt thereof.

22. The compound of claim 1 wherein the compound is 2-((1r,3s)-1-(4-(6-(3-amino-1H-pyrazol-5-yl)pyrazolo[1,5-a]pyrazin-4-yl)-1H-pyrazol-1-yl)-3-methoxycyclobutyl)acetonitrile, or a pharmaceutically acceptable salt thereof.

23. The compound of claim 1 wherein the compound is 2-(1-ethyl-3-(4-(6-(5-(hydroxymethyl)-1H-pyrazol-3-yl)pyrazolo[1,5-a]pyrazin-4-yl)-1H-pyrazol-1-yl)azetidin-3-yl)acetonitrile, or, a pharmaceutically acceptable salt thereof.

24. A pharmaceutical composition comprising a compound of claim 1, or a pharmaceutically acceptable salt thereof, or a pharmaceutically acceptable solvate of said compound or salt, and a pharmaceutically acceptable excipient.

* * * * *